United States Patent
Crawford et al.

(10) Patent No.: US 9,915,649 B2
(45) Date of Patent: *Mar. 13, 2018

(54) METHODS OF DETERMINING THE PRESENCE, IDENTITY, AND/OR SEVERITY OF MUCOPOLYSACCHARIDOSIS (MPS) VI AND IVA

(71) Applicant: BIOMARIN PHARMACEUTICALS INC., Novato, CA (US)

(72) Inventors: Brett E. Crawford, Poway, CA (US); Jillian R. Brown, Poway, CA (US); Charles A. Glass, Novato, CA (US); Jim R. Beitel, Novato, CA (US); Robin M. Jackman, San Diego, CA (US)

(73) Assignee: BIOMARIN PHARMACEUTICALS INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/097,218

(22) Filed: Apr. 12, 2016

(65) Prior Publication Data

US 2016/0327548 A1 Nov. 10, 2016

Related U.S. Application Data

(63) Continuation of application No. 14/462,285, filed on Aug. 18, 2014, now Pat. No. 9,340,822, which is a continuation of application No. 13/629,321, filed on Sep. 27, 2012, now Pat. No. 8,809,009, and a continuation-in-part of application No. 13/550,106, filed on Jul. 16, 2012, now Pat. No. 8,771,974, which is a continuation of application No. 12/649,110, filed on Dec. 29, 2009, now Pat. No. 8,232,073.

(60) Provisional application No. 61/561,698, filed on Nov. 18, 2011, provisional application No. 61/142,291, filed on Jan. 2, 2009, provisional application No. 61/164,365, filed on Mar. 27, 2009, provisional application No. 61/238,079, filed on Aug. 28, 2009.

(51) Int. Cl.
| | |
|---|---|
| C12Q 1/42 | (2006.01) |
| G01N 33/53 | (2006.01) |
| C12Q 1/34 | (2006.01) |
| C12Q 1/40 | (2006.01) |
| C12Q 1/527 | (2006.01) |
| G01N 33/68 | (2006.01) |

(52) U.S. Cl.
CPC .......... *G01N 33/5308* (2013.01); *C12Q 1/34* (2013.01); *C12Q 1/40* (2013.01); *C12Q 1/42* (2013.01); *C12Q 1/527* (2013.01); *G01N 33/6893* (2013.01); *G01N 2333/924* (2013.01); *G01N 2333/988* (2013.01); *G01N 2400/00* (2013.01); *G01N 2400/10* (2013.01); *G01N 2800/04* (2013.01); *G01N 2800/042* (2013.01); *G01N 2800/044* (2013.01); *G01N 2800/28* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 5,185,245 A | 2/1993 | Heimer | |
| 6,117,647 A | 9/2000 | Romisch et al. | |
| 6,143,730 A | 11/2000 | Parish et al. | |
| 6,653,285 B1 | 11/2003 | Takashima et al. | |
| 6,852,696 B2 | 2/2005 | Takashima et al. | |
| 6,923,965 B2 | 8/2005 | Takashima et al. | |
| 6,936,424 B1 | 8/2005 | Watkins et al. | |
| 7,651,847 B2 | 1/2010 | Lebrilla et al. | |
| 8,183,003 B2 | 5/2012 | Crawford et al. | |
| 8,232,073 B2 * | 7/2012 | Crawford | C12Q 1/40 435/15 |
| 8,592,140 B2 | 11/2013 | Crawford et al. | |
| 8,771,974 B2 * | 7/2014 | Crawford | C12Q 1/40 435/15 |
| 8,809,009 B2 * | 8/2014 | Crawford | C12Q 1/42 435/15 |
| 9,222,120 B2 * | 12/2015 | Crawford | C12Q 1/40 |
| 9,340,822 B2 * | 5/2016 | Crawford | C12Q 1/42 |
| 2002/0102737 A1 | 8/2002 | Millington et al. | |
| 2003/0024012 A1 | 1/2003 | Abdennebi-Najar et al. | |
| 2003/0054991 A1 | 3/2003 | Takashima et al. | |
| 2003/0228259 A1 | 12/2003 | Hellerstein | |
| 2004/0138105 A1 | 7/2004 | Takashima et al. | |
| 2005/0159343 A1 | 7/2005 | Takashima et al. | |
| 2005/0238536 A1 | 10/2005 | Striepeke et al. | |

(Continued)

FOREIGN PATENT DOCUMENTS

| | | |
|---|---|---|
| GB | 2468386 A | 9/2010 |
| WO | 01/31045 A1 | 5/2001 |

(Continued)

OTHER PUBLICATIONS

An et al., "Glucose tetrasaccharide as a biomarker for monitoring the therapeutic response to enzyme replacement therapy for Pompe disease," Mol. Genet. Metab. 85(4):247-254 (2005).

An et al., "Profiling of glycans in serum for the discovery of potential biomarkers for ovarian cancer," J. Proteome Res. 5(7):1626-1635 (2006).

Byers et al., "Glycosaminoglycan accumulation and excretion in the mucopolysaccharidoses: Characterization and basis of a diagnostic test for MPS," Molecular Genetics and Metabolism, 65(4):282-290 (1998).

Calabro et al., "Adaptation of FACE methodology for microanalysis of total hyaluronan and chondroitin sulfate composition from cartilage," Glycobiology 10(3):283-293 (2000).

Calabro et al., "Microanalysis of enzyme digests of hyaluronan and chondroitin/dermatan sulfate by fluorophore-assisted carbohydrate electrophoresis (FACE)," Glycobiology 10(3):273-281 (2000).

(Continued)

*Primary Examiner* — Ralph J Gitomer
(74) *Attorney, Agent, or Firm* — Jones Day

(57) ABSTRACT

Provided herein are methods of diagnosing or monitoring the treatment of abnormal glycan accumulation or a disorder associated with abnormal glycan accumulation.

34 Claims, 16 Drawing Sheets

(56) References Cited

U.S. PATENT DOCUMENTS

| | | |
|---|---|---|
| 2006/0079483 A1 | 4/2006 | Hung et al. |
| 2006/0269974 A1 | 11/2006 | Dwek et al. |
| 2006/0286034 A1 | 12/2006 | Meikle et al. |
| 2007/0161074 A1 | 7/2007 | Tomatsu et al. |
| 2008/0071148 A1 | 3/2008 | Bosques et al. |
| 2008/0153752 A1 | 6/2008 | Takashima et al. |
| 2010/0048638 A1 | 2/2010 | Crawford et al. |
| 2010/0173337 A1 | 7/2010 | Crawford et al. |
| 2010/0184013 A1 | 7/2010 | Crawford et al. |
| 2010/0248365 A1 | 9/2010 | Crawford et al. |
| 2011/0311988 A1 | 12/2011 | Crawford et al. |
| 2012/0009616 A1 | 1/2012 | Crawford et al. |
| 2012/0100609 A1 | 4/2012 | Crawford et al. |
| 2012/0289415 A1 | 11/2012 | Bosques et al. |
| 2012/0295890 A1 | 11/2012 | Crawford et al. |
| 2013/0149729 A1 | 6/2013 | Crawford et al. |
| 2013/0217056 A1 | 8/2013 | Crawford et al. |
| 2016/0153024 A1* | 6/2016 | Crawford ............... C12Q 1/40 435/7.92 |

FOREIGN PATENT DOCUMENTS

| | | |
|---|---|---|
| WO | 01/36977 A2 | 5/2001 |
| WO | 01/94941 A2 | 12/2001 |
| WO | 01/94941 A3 | 8/2003 |
| WO | 03/092601 A2 | 11/2003 |
| WO | 03/106997 A1 | 12/2003 |
| WO | 2004/019040 A1 | 3/2004 |
| WO | 03/092601 A3 | 9/2004 |
| WO | 2007/010089 A2 | 1/2007 |
| WO | 2007/010089 A3 | 5/2007 |
| WO | 2007/138263 A1 | 12/2007 |
| WO | 2010/078511 A2 | 7/2010 |
| WO | 2010/078514 A2 | 7/2010 |
| WO | 2010/078511 A3 | 10/2010 |

OTHER PUBLICATIONS

Daud et al., "Synthetic heparin pentasaccharide depolymerization by heparinase 1: Molecular and biological implications," Clin. Appl. Thromb. Hemost. 7(1):58-64 (2001).

Deakin and Lyon, "A simplified and sensitive fluorescent method for disaccharide analysis of both heparin sulfate and chondroitin-dermatan sulfates from biological samples," Glycobiology 18(6):483-491 (2008).

Deegan et al., "Clinical evaluation of chemokine and enzymatic biomarkers of Gaucher disease," Blood Cells Mol. Dis. 35(2):259-267 (2005).

Delaney et al., "A high-performance liquid chromatography approach for isolation and sequencing of chondroitin sulfate oligosaccharides," Anal. Biochem. 108(1):25-34 (1980).

Ferro et al., "Evidence of conformational equilibrium of the sulfated L-iduronate residue in heparin and in synthetic heparin mono- and oligosaccharides: NMR and force-field studies," J. Am. Chem. Soc. 108:6778-6784 (1986).

Freeman and Hopwood, "Human α-L-iduronidase. Catalytic properties and an integrated role in the lysosomal degradation of heparan sulphate," Biochem. J. 282( Pt 3):899-908 (1992).

Fuller et al., "Glycosaminoglycan degradation fragments in mucopolysaccharidosis I," Glycobiology 14(5):443-450 (2004).

Hansen et al., "HPLC glycosaminoglycan analysis in patients with Graves' disease," Clin. Sci. (Lond) 92(5):511-517 (1997).

Hitchcock et al., "Comparative glycomics of connective tissue glycosaminoglycans," Proteomics 8(7):1384-1397 (2008).

Honda et al., "High-performance capillary electrophoresis of unsaturated oligosaccharides derived from glycosaminoglycans by digestion with chondroitinase ABC as 1-phenyl-3 methyl-5-pyrazolone derivatives," J. Chromatogr. 608(1-2)289-295 (1992).

Hopwood and Elliott, "Urinary excretion of sulphated N-acetylhexosamines in patients with various mucopolysaccharidoses," Biochem. J. 229(3):579-586 (1985).

Imanari et al., "High performance liquid chromatographic analysis of glycosaminoglycan-derived oligosaccharides," J. Chromatogr. A. 720(1-2):275-293 (1996).

International Search Report and Written Opinion for PCT/US2009/069946 dated Sep. 9, 2012.

International Search Report for PCT/US2009/069941 mailed Aug. 27, 2010.

International Search Report for PCT/US2009/069944 mailed Aug. 31, 2010.

International Search Report for PCT/US2013/061914 mailed Dec. 17, 2013.

Jacquinet et al., "Synthesis of heparin fragments. A chemical synthesis of the trisaccharideO-(2-deoxy-2-sulfamido-3,6-di-O-sulfo-α-d-glucopyranosyl)-(1→4)-O-(2-O-sulfo-α-I-idopyranosyluronic acid)-(1→4)-2-deoxy-2-sulfamido-6-O-sulfo-d-glucopyranose heptasodium salt," Carbohydr. Res. 130:221-241 (1984).

Kimura et al., "Chemical structure of urinary dermatan sulfate excreted by a patient with the Hunter syndrome," Tohoku J. Exp. Med. 131(3):241-247 (1980).

Kimura et al., "Fractionation and characterization of urinary heparan sulfate excreted by patients with Sanfilippo syndrome," Tohoku J. Exp. Med. 144(3):227-236 (1984).

Kirmiz et al., "A serum glycomics approach to breast cancer biomarkers," Mol. Cell. Proteomics 6(1):43-55 (2007).

Kodama et al., "High-performance liquid chromatography of pyridylamino derivatives of unsaturated disaccharides produced from chondroitin sulfate isomers by chondroitinases," J. Biochem. 96(4):1283-1287 (1984).

Kodama et al., "Liquid-chromatographic determination of urinary glycosaminoglycans for differential diagnosis of genetic mucopolysaccharidoses," Clin. Chem. 31(1 Pt 1):30-34 (1986).

Lawrence et al., "Evolutionary differences in glycosaminoglycan fine structure detected by quantitative glycan reductive isotope labeling," J. Biol. Chem. 283(48):33674-33684 (2008).

MacCari et al., "Anomolous structure of urinary glycosaminoglycans in patients with pseudoxanthoma elasticum," Clin. Chem. 49(3):380-388 (2003).

Mahuran, "Biochemical consequences of mutations causing the GM2 gangliosidoses," Biochim. Biophys. Acta 1455 (2-3)105-138 (1999).

Mao et al., "Capillary electrophoresis for the analysis of glycosaminoglycans and glycosaminoglycan-derived oligosaccharides," Biomed. Chromatogr. 16(2):77-94 (2002).

Mason et al., "Characterization of sulfated oligosaccharides in mucopolysaccharidosis type IIIA by electrospray ionization mass spectrometry," Anal. Chem. 78(13):4534-4542 (2006).

Matzner et al., "Enzyme replacement improves nervous system pathology and function in a mouse model for metachromatic leukodystrophy," Hum. Mol. Genet 14(9):1139-1152 (2005) (Epub Mar. 16, 2005).

Minamisawa et al., "Microscale preparation of even- and odd-numbered N-acetylheparosan oligosaccharides," Carbohydr. Res. 341(2):230-237 (2006).

Minamisawa et al., "Systematic identification of N-acetylheparosan oligosaccharides by tandem mass spectrometric fragmentation," Rapid Commun. Mass Spectrom. 20:267-274 (2006).

Nader et al., "Chemistry of heparitin sulfate and heparin from normal tissues and from patients with Hunter syndrome," Biochim Biophys Acta. 582(1):33-43 (1979).

Nomenclature Committee Consortium for Functional Glycomics "Symbol and Text Nomenclature for Representation of Glycan Structure" (May 2012) accessed on internet on Sep. 12, 2012 at http://www.functionalglycomics.org/static/consortium/Nomenclature.shtml.

Plaas et al., "Glycosaminoglycan sulfation in human osteoarthritis: Disease-related alterations at the non-reducing termini of chondroitin and dermatan sulfate," J. Biol. Chem. 273(20):12642-12649 (1998).

Pol-Fachin and Verli, "Depiction of the forces participating in the 2-O-sulfo-α-L-iduronic acid conformational preference in heparin sequences in aqueous solutions," Carbohydr. Res. 343:1435-1445 (2008).

(56) References Cited

OTHER PUBLICATIONS

Rhomberg et al., "Mass spectrometric evidence for the enzymatic mechanism of the depolymerization of heparin-like glycosaminoglycans by heparinase II," Proc. Natl. Acad. U.S.A. 95(21):12232-12237 (1998).

Rong et al., "Substrate specificity of the heparin sulfate hexuronic acid 2-O-sulfotransferase," Biochemistry 40 (18):5548-5555 (2001).

Smeds et al. "Target selection of heparan sulfate hexuronic acid 2-O-sulfotransferase," Glycobiology 20 (10):1274-1282 (2010).

Thanawiroon et al., "Liquid chromatography/mass spectrometry sequencing approach for highly sulfated heparin-derived oligosaccharides," J. Biol. Chem. 279(4):2608-2615 (2004).

Thompson et al., "Oligosaccharide substrates for heparin sulfamidase," Anal. Chem. 152:412-422 (1986).

Toma et al., "Differences in the non-reducing ends of heparan sulfates excreted by patients with mucopolysaccharidoses revealed by bacterial heparitinases: A new tool for structural studies and differential diagnosis of Sanfilippo's and Hunter's syndromes," Lab. Invest. 75(6): 771-781 (1996).

Volpi and MacCari, "Glycosaminoglycan composition of the large freshwater mollusc bivalve Anodonta anodonta," Biomacromolecules 6(6):3174-3180 (2005).

Volpi et al., "Mass spectrometry for the characterization of unsulfated chondroitin oligosaccharides from 2-mers to 16-mers. Comparison with hyaluronic acid oligomers," Rapid Commun. Mass Spectrom. 22(22):3526-3530 (2008).

Yamada et al., "Structural studies on the tri- and tetrasaccharides isolated from porcine intestinal heparin and characterization of heparinase/heparitinases using them as substrates," Glycobiology 4(1):69-78 (1994).

Yan et al., "Prediction and simulation on interaction between HIV-1 envelope protein gp120 and heparin," Chem. J. Chinese U. 25(3):522-525 (2004). (in Chinese with English abstract).

Yosizawa et al., "A simple method for the quantitation of glycuronic acid-containing glycosaminoglycans with mucopolysaccharidases," Anal. Biochem. 128(1):250-256 (1983).

Brown et al., "Diagnosis and Monitoring of Mucopolysaccharidoses Using Disease-Specific Non-Reducing End Carbohydrate Biomarkers", 105(2):S23 abstract (2012).

Faid et al., "A rapid mass spectrometric strategy for the characterization of N- and O-glycan chains in the diagnosis of defects in glycan biosynthesis", Proteomics, 7(11):1800-1813 (2007).

Royle et al., "HPLC-based analysis of serum N-glycans on a 96-well plate platform with dedicated database software", Anal Biochem., 376(1):1-.12 (2008).

Van Boeckel et al., "Conformational analysis of synthetic heparin-like oligosaccharides containing alpha-L-idopyranosyluronic acid" Recl Tray Chim Phays-Bas, 106:19-29 (1987).

Murata et al., "High-performance liquid chromatographic identification of eight constitutional disaccharides from heparan sulfate isomers digested with heparinases", J Chromatogr B Biomed Appl., 670(1):3-10 (1995).

Saad et al., "Compositional analysis and quantification of heparin and heparan sulfate by electrospray ionization ion trap mass spectrometry", Anal Chem., 75(13):2985-2995 (2003).

Zaia, "On-line separations combined with MS for analysis of glycosaminoglycans", Mass Spectrom Rev., 28 (2):254-272 (2009).

Zaia, "Principles of Mass Spectrometry of Glycosaminoglycans", Journal of Biomacromolecular Mass Spectrometry, 1(1):1-36 (2005).

\* cited by examiner

METHODS OF DETERMINING THE PRESENCE, IDENTITY, AND/OR SEVERITY OF MUCOPOLYSACCHARIDOSIS (MPS) VI AND IVA

CROSS-REFERENCE

This application is a continuation application of U.S. application Ser. No. 14/462,285 filed Aug. 18, 2014, now U.S. Pat. No. 9,340,822, which is a continuation of U.S. application Ser. No. 13/629,321 filed Sep. 27, 2012, now U.S. Pat. No. 8,809,009, which claims the benefit of U.S. Provisional Application No. 61/561,698, filed Nov. 18, 2011, and is a continuation-in-part of U.S. application Ser. No. 13/550,106, filed Jul. 16, 2012, now U.S. Pat. No. 8,771,974, which is a continuation of U.S. application Ser. No. 12/649,110, filed Dec. 29, 2009, now U.S. Pat. No. 8,232,073, which claims the benefit of U.S. Provisional Application No. 61/142,291, filed Jan. 2, 2009, U.S. Provisional Application No. 61/164,365, filed Mar. 27, 2009, and U.S. Provisional Application No. 61/238,079, filed Aug. 28, 2009; each of which are incorporated herein by reference in their entirety.

BACKGROUND OF THE INVENTION

Many human diseases are caused by or correlated with changes in glycosylation. In order to use these changes as biomarkers of disease, analytical methods are used to quantify the changes. The published methods use antibodies, chromatography and/or mass spectrometry techniques to resolve and quantify the intact or partially intact glycans. These methods are challenging due to the complexity and number of possible glycan structures present in biological samples. In a single disease state there can be thousands of different novel glycan structures that are present; however, each on their own is a weak marker of disease.

SUMMARY OF THE INVENTION

Described herein are populations of glycans that are transformed into populations of biomarkers using glycan degradation enzymes. In some embodiments, described herein are populations of glycosaminoglycans that are transformed into populations of oligosaccharides using glycosaminoglycan lyases. Further described herein are the use of analytical instruments to characterize the population of biomarkers (i.e., non-reducing end glycan residual compounds, such as monosaccharides) in order to provide relevant information about the population of biomarkers, the population of biomarkers and the biological sample that provided the population of biomarkers. In some embodiments, described herein are the use of analytical instruments to characterize the population of oligosaccharides in order to provide relevant information about the population of oligosaccharides, the population of glycosaminoglycans and the biological sample that provided the population of glycosaminoglycans.

Provided in certain embodiments herein are methods of detecting glycan accumulation and/or abnormal glycan biosynthesis and/or degradation in a biological sample, the method comprising:
  a. transforming a glycan of a biological sample with a glycan degradation enzyme to liberate a glycan residual compound from the non-reducing end of the glycan;
  b. measuring the amount of the glycan residual compound liberated by the functioning glycan degradation enzyme with an analytical device.

In some embodiments, a method described herein comprises a method of diagnosing an individual as having a disease or condition associated with abnormal glycan biosynthesis, degradation, or accumulation, the method comprising:
  a. generating a biomarker comprising of one or more non-reducing end glycan residual compound, wherein the biomarker is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition, and
  b. using an analytical instrument to detect the presence of and/or measure the amount of the biomarker produced and displaying or recording the presence of or a measure of a population of the biomarker.

In some embodiments, the presence of and/or measure the amount of the biomarker is utilized to determine the presence, identity, and/or severity of the disease or condition.

Provided in certain embodiments herein is a method of diagnosing an individual as having a disease or condition associated with abnormal glycan biosynthesis, degradation, or accumulation, the method comprising:
  a. transforming a glycan of a biological sample with a glycan degradation enzyme to liberate a glycan residual compound from the non-reducing end of the glycan;
  b. measuring the amount of the glycan residual compound liberated by the functioning glycan degradation enzyme with an analytical device; and
  c. determining whether the amount of liberated glycan residue is abnormal.

In some embodiments, provided herein is a method of monitoring the treatment of a disorder associated with the abnormal degradation, biosynthesis and/or accumulation of glycans, the method comprising:
  a. following administration of an agent for treating a disorder associated with the abnormal degradation, biosynthesis and/or accumulation of glycans to an individual in need thereof, using an analytical instrument to measure the amount of a population of a biomarker comprising a non-reducing end glycan residual compounds present in a transformed biological sample, the biomarker being generated by treating a population of glycans, in or isolated from a biological sample from the individual, with at least one digesting glycan enzyme(s), wherein prior to enzyme treatment, the biomarker is not present in abundance in samples from individuals with the disease or condition relative to individuals without the disease or condition, and
  b. determining whether or not the amount of biomarker has decreased or increased at a slower rate compared to the amount or rate of increase prior to administration of the agent for treating a disorder associated with the abnormal degradation, biosynthesis and/or accumulation of glycans.

In some embodiments, the disorder associated with the abnormal degradation, biosynthesis and/or accumulation of glycans is a lysosomal storage disease, a cancerous disease, an inflammatory disease, an infectious disease, a central nervous system disease, or a cardiovascular disease. In some embodiments, the normally functioning glycan degradation enzyme is a glycosidase, sulfatase, phosphorylase, deacetylase, or a combination thereof. In some embodiments, the normally functioning glycan degradation enzyme is a glycosidaseis selected from an exo-glycosidase and an endo-glycosidase. In some embodiments, the glycan residual compound is a monosaccharide, sulfate, phosphate, acetate, or a combination thereof.

In some embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof. In some embodiments, prior to measuring the amount of a population of non-reducing end glycan residual compounds, the non-reducing end glycan residual compounds are labeled with a detectable label. In some embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

Provided in certain embodiments herein is a method of diagnosing an individual as having a disease or condition associated with abnormal glycan biosynthesis, degradation, or accumulation, the method comprising:
a. generating a biomarker comprising of one or more non-reducing end glycan residual compound, wherein the biomarker is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition, and
b. using an analytical instrument to detect the presence of and/or measure the amount of the biomarker produced and displaying or recording the presence of or a measure of a population of the biomarker;

wherein the presence of and/or measure the amount of the biomarker is utilized to determine the presence, identity, and/or severity of the disease or condition.

In some embodiments, the disease or disorder is caused by an abnormally functioning glycan degradation enzyme and wherein the abnormally functioning glycan degradation enzyme and the normally functioning glycan degradation enzyme are of the same type. In some embodiments, the abnormally functioning glycan degradation enzyme functions abnormally as a result of being present in an abnormally low amount, functioning improperly, or a combination thereof. In some embodiments, the abnormal glycan accumulation comprises the accumulation of abnormal amounts of glycans. In some embodiments, the abnormal glycan accumulation comprises the accumulation of abnormal amounts of normal glycans. In some embodiments, the abnormal glycan accumulation comprises the accumulation of abnormal amounts of abnormal glycans.

In some embodiments, the normally functioning glycan degradation enzyme is a glycosidase, sulfatase, phosphorylase, deacetylase, or a combination thereof. In some embodiments, the normally functioning glycan degradation enzyme is a glycosidase selected from an exo-glycosidase and an endo-glycosidase. In some embodiments, the glycosidase is an exo-glycosidase selected from the group consisting of a galactosidase, and a glucuronidase.

In some embodiments, the glycan residual compound is a monosaccharide. In some embodiments, the glycan residual compound is sulfate, phosphate, acetate, or a combination thereof. In some embodiments, a biological sample is purified prior to transforming a glycan thereof. In some embodiments, the process of purifying a biological sample comprises removing monosaccharides therefrom, removing sulfates therefrom, removing phosphates therefrom, removing acetate therefrom, or a combination thereof. In some embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof.

In some embodiments, the disorder associated with an abnormal glycan accumulation is MPS I, MPS II, MPS IIIA, MPS IVA, MPSVI, or Fabry Disease. In some embodiments, determining whether the amount of liberated glycan residue is abnormal comprises labeling the glycan residue with a detectable label and measuring the amount of labeled glycan residue with an analytical instrument. In some embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

Provided herein, in certain embodiments, is a method of diagnosing an individual as having a disease or condition (e.g., associated with abnormal glycan biosynthesis, degradation, or accumulation), the method comprising:
a. generating a first biomarker comprising a glycan residual compound, wherein the first biomarker is generated by treating a population of glycans, in or isolated from a biological sample from the individual, with at least one digesting glycan enzyme, wherein prior to enzyme treatment, the first biomarker is not present in abundance in samples from individuals with the disease or condition relative to individuals without the disease or condition,
b. generating a second biomarker comprising a glycan residual compound, wherein the second biomarker is generated by treating a population of glycans, in or isolated from a biological sample from the individual, with at least one digesting glycan enzyme in the same or different digestion step as provided in step (a), wherein prior to enzyme treatment, the second biomarker is not present in abundance in samples from individuals with the disease or condition relative to individuals without the disease or condition,
c. using an analytical instrument to detect the presence of and/or measure the amount of the first and second biomarker produced and displaying or recording the presence of or a measure of a population of the first and second biomarkers, and
d. monitoring and/or comparing the amounts of the first and second biomarkers in a biological sample;

wherein the presence of and/or measure of the amounts of the first and second biomarkers are utilized to determine the presence, identity, and/or severity of the disease or condition.

In some embodiments, the first biomarker is a non-reducing end glycan residual compound. In some embodiments, the disease or disorder is caused by an abnormally functioning glycan degradation enzyme and wherein the abnormally functioning glycan degradation enzyme and the digesting glycan enzyme are of the same type. In some embodiments, the non-reducing end glycan residual compound is a monosaccharide. In some embodiments, the non-reducing end glycan residual compound is not a monosaccharide.

In some embodiments, the second biomarker is derived or generated from the reducing end of the same glycan from which the first non-reducing end glycan residual compound biomarker was generated. In some embodiments, the second biomarker is derived or generated from the internal oligosaccharide structures of the same glycan from which the first non-reducing end glycan residual compound biomarker was generated. In some embodiments, the disease or disorder is caused by the abnormal function of a glycan degradation enzyme in the individual, and wherein the second biomarker can be generated by treating the first non-reducing end glycan residual compound biomarker with the glycan degradation enzyme that is functioning abnormally in the individual.

In some embodiments, the disease or condition associated with abnormal glycan biosynthesis, degradation, or accumulation is a lysosomal storage disease. In some embodiments, the lysosomal storage disease is Mucopolysaccharidosis. In some embodiments, the Mucopolysaccharidosis is MPS I, II, IIIA, IIIB, IIIC, IIID, IVA, IVB, VI, or VII. In some embodiments, the disease or condition associated with abnormal glycan biosynthesis, degradation, or accumulation is Metachromatic Leukodystrophy or Krabbe disease. In some embodiments, the disease or condition associated with abnormal glycan biosynthesis, degradation, or accumulation is Gangliosidosis. In some embodiments, the Gangliosidosis is Tay Sachs, Sandhoff, AB Variant, or GM-1 Gangliosidoses.

In some embodiments, the presence of and/or measure of the first non-reducing end glycan residual compound biomarker in combination with or in relation to the second biomarker is utilized to monitor the treatment of a disorder associated with the abnormal biosynthesis of glycans. In some embodiments, the presence of and/or measure of the first non-reducing end glycan residual compound biomarker in combination with or in relation to the second biomarker is utilized to monitor the treatment of a disorder associated with the abnormal degradation or accumulation of glycans. In some embodiments, the treatment is enzyme replacement therapy. In some embodiments, the absence of an increase in the second biomarker combined with a reduction in the non-reducing end glycan residual compound biomarker indicates a positive response to treatment of the disorder associated with abnormal degradation or accumulation of glycans.

In some instances, a method described herein comprises utilization of a first biomarker that is a non-reducing end glycan biomarker, e.g., as set forth in US 2010/0184013, which is incorporated by reference herein in its entirety. In certain embodiments, the first biomarker is a C4-C5 non-reducing end saturated oligosaccharide. In some embodiments, the non-reducing end residue of the first biomarker (e.g., one or more disaccharide and/or one or more trisaccharide) are free of carbon-carbon unsaturation.

In some embodiments, the abnormal glycan accumulation or disorder associated therewith is caused by an abnormally functioning glycan degradation enzyme and wherein the abnormally functioning glycan degradation enzyme and glycan degradation enzyme are of the same type (e.g., the glycan degradation utilized in the transformation process is a functioning glycan degradation enzyme whereas the the abnormally functioning enzyme is not, such as due to deletions, insertions, substitutions, or other modifications to the enzyme sequence). In certain embodiments, the abnormally functioning glycan degradation enzyme functions abnormally as a result of being present in an abnormally low amount, functioning improperly, or a combination thereof. In some embodiments, the abnormal glycan accumulation comprises the accumulation of abnormal amounts of glycans. In certain embodiments, the abnormal glycan accumulation comprises the accumulation of abnormal amounts of normal glycans. In some embodiments, the abnormal glycan accumulation comprises the accumulation of abnormal amounts of abnormal glycans.

In certain embodiments, the biomarker is not present in the original biological sample. In some embodiments, the biomarker is not present in the biological sample after isolating a population of glycans therefrom (e.g., prior to transformation of the glycan according to a process described herein).

In certain embodiments, the normally functioning glycan degradation enzyme is a glycosidase, sulfatase, phosphorylase, deacetylase or a combination thereof. In some embodiments, the normally functioning glycan degradation enzyme is a glycosidase selected from an exo-glycosidase and an endo-glycosidase. In certain embodiments, the glycosidase is an exo-glycosidase selected from the group consisting of a galactosidase, and a glucuronidase. In some embodiments, the generated biomarker is a glycan residual compound. In some embodiments, the glycan residual compound is a monosaccharide. In certain embodiments, the glycan residual compound is sulfate, phosphate, acetate, or a combination thereof. In certain embodiments, the glycan residual compound has a molecular weight of less than 2000 g/mol, less than 1500 g/mol, less than 1000 g/mol, less than 500 g/mol, less than 400 g/mol, less than 300 g/mol, less than 260 g/mol, less than 200 g/mol, less than 100 g/mol, or the like (e.g., prior to tagging with any detectable label that may be included in a process described herein).

In some embodiments, any process described herein further comprises purifying a biological sample prior to transforming a glycan thereof. In some embodiments, the process of purifying a biological sample comprises removing monosaccharides therefrom, removing sulfates therefrom, removing phosphates therefrom, removing acetate therefrom, or a combination thereof.

In certain embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof.

In specific embodiments, a disorder associated with an abnormal glycan accumulation is any disorder described in Tables 1-4 (e.g., MPS I) and the normally functioning glycan degradation enzyme is any enzyme described in Tables 1-4 (e.g., L-iduronidase).

In some embodiments, determining whether the amount of liberated glycan residue is abnormal comprises labeling the glycan residue with a detectable label and measuring the amount of labeled glycan residue with an analytical instrument. In certain embodiments, the detectable label is a mass label, a radioisotope label, a fluorescent label, a chromophore label, or affinity label. In some embodiments, the amount of liberated glycan is measured using UV-V is spectroscopy, IR spectroscopy, mass spectrometry, or a combination thereof.

Provided in some embodiments herein is a method of monitoring the treatment of a disorder associated with the abnormal degradation, biosynthesis and/or accumulation of glycans, the methods comprising:

a. following administration of an agent for treating a disorder associated with the abnormal degradation, biosynthesis and/or accumulation of glycans to an individual in need thereof, using an analytical instrument to measure the amount of a population of a non-reducing end glycan residual compounds present in a transformed biological sample that has been prepared by:
   treating a population of glycans, in or isolated from a biological sample taken from the individual, with at least one normally functioning glycan degradation enzyme to liberate non-reducing end glycan residual compound;
b. determining whether or not the amount of liberated non-reducing end glycan residue has decreased or increased at a slower rate compared to the amount or rate of increase prior to administration of the agent for treating a disorder associated with the abnormal degradation, biosynthesis and/or accumulation of glycans.

In some embodiments, the disorder associated with the abnormal degradation, biosynthesis and/or accumulation of glycans is a lysosomal storage disease, a cancerous disease, or an infectious disease. In certain embodiments, the normally functioning glycan degradation enzyme is a glycosidase, sulfatase, phosphorylase, deacetylase, or a combination thereof. In some embodiments, the normally functioning glycan degradation enzyme is a glycosidase selected from an exo-glycosidase and an endo-glycosidase. In certain embodiments, the glycan residual compound is a monosaccharide, sulfate, phosphate, acetate, or a combination thereof. In some embodiments, transforming a glycan of a biological sample with a normally functioning glycan degradation enzyme comprises transforming a glycan of a biological sample with a plurality of normally functioning glycan degradation enzymes. In certain embodiments, the glycan is treated with a plurality of normally functioning glycan degradation enzymes concurrently, sequentially, or a combination thereof.

In some embodiments, prior to measuring the amount of a population of non-reducing end glycan residual compounds, the non-reducing end glycan residual compounds are labeled with a detectable label. In certain embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
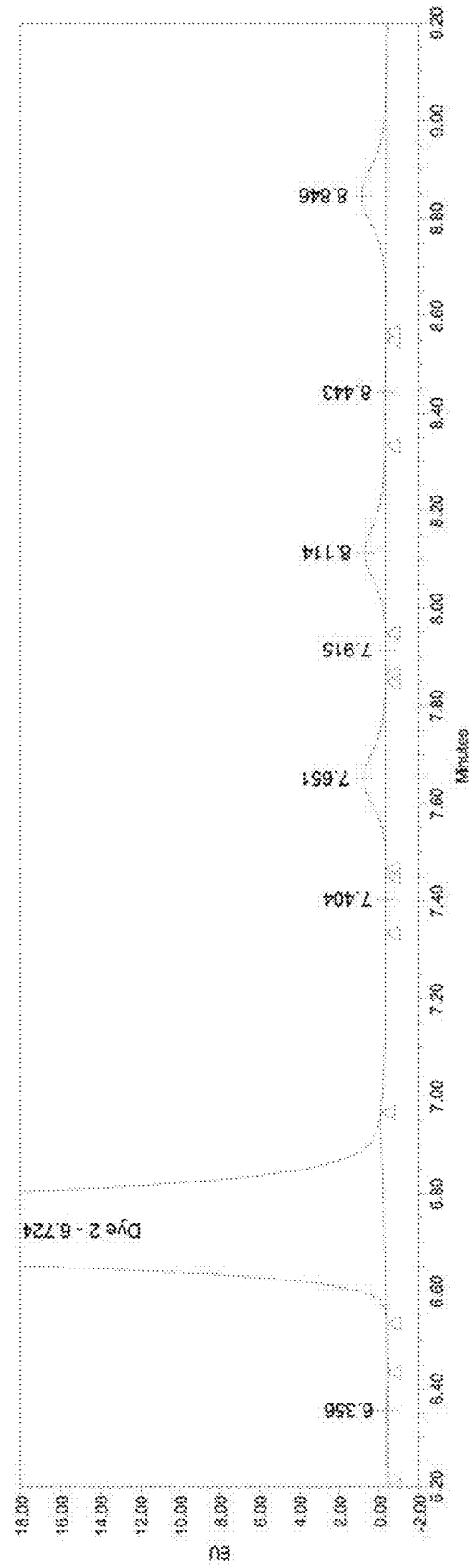
FIG. 1 illustrates compounds present in a normal biological sample not subject to an enzymatic glycan residual liberation process described herein.

While preferred embodiments of the present invention have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Glycosaminoglycans comprise a reducing end and a non-reducing end. Normal biological processes degrade glycosaminoglycans (such as heparan sulfate which has a normal component of about 50-80 kDa) into monosaccharides. Disorders associated with abnormal glycosaminoglycan degradation, biosynthesis, and/or accumulation can result in an accumulation of glycosaminoglycans and fragments thereof.

Many human diseases are caused by or correlated with changes in glycosaminoglycans. In order to use these changes as biomarkers of disease, analytical methods are used to quantify the changes. Some methods use antibodies, chromatography and/or mass spectrometry techniques to resolve and quantify the intact or partially intact glycans. The use of such methods are challenging due to the complexity and number of possible glycan structures present in biological samples. To address the complexity, methods have been developed which employ glycan digesting enzymes to liberate and quantify homogenous oligosaccharides generated from the polymeric glycosaminoglycans. The use of individual oligosaccharides as the biomarker of disease may not be sufficient. As a result, an opportunity exists to combine oligosaccharide biomarkers to provide the necessary insight related to presence of disease, prediction of severity, and characterization of the response to treatment.

Provided herein is a method of detecting abnormal glycan accumulation, e.g., in human disease. In some instances, the process described herein includes a strategy to quantify the changes by measuring the abundance of all glycans with a disease related glycan residual compound on the non-reducing end of glycans from a biological sample (e.g., monosaccharides and/or their modifications such as sulfation, acetylation, phosphorylation, or the like).

Provided in certain embodiments herein are methods of detecting glycan accumulation in a biological sample, the method comprising:
  a. transforming a glycan of a biological sample with a normally functioning glycan degradation enzyme to liberate a glycan residual compound from the non-reducing end of the glycan;
  b. measuring the amount of the glycan residual compound liberated by the functioning glycan degradation enzyme with an analytical device.

In certain embodiments, the method is associated with diagnosing an individual with abnormal glycan accumulation, or a disorder associated therewith.

Therefore, in specific embodiments, provided herein is a method of diagnosing an individual as having an abnormal glycan accumulation or a disorder associated with an abnormal glycan accumulation, the method comprising:
  a. transforming a glycan of a biological sample with a normally functioning glycan degradation enzyme to liberate a glycan residual compound from the non-reducing end of the glycan;
  b. measuring the amount of the glycan residual compound liberated by the functioning glycan degradation enzyme with an analytical device; and
  c. determining whether the amount of liberated glycan residue is abnormal.

In certain instances, methods of detecting abnormal glycan accumulation works based on the observation that altered glycans generated in a disease state are caused by an alteration in the activity of a biosynthetic enzyme (e.g., via increased expression, increased activity, increased substrate, or the like) that leads to the production of thousands of unique structures.

For example, in certain instances, the induction of an alpha 2,3 sialyltransferase leads to the novel expression of thousands of different glycans (potentially from multiple glycan classes) that present a non-reducing terminal alpha 2,3 linked sialic acid. By quantifying a limited set of these novel structures using current methods, only a fraction of the disease related structures are measured. Instead, as provided in certain embodiments herein, if a sample containing glycans (crude or purified for a specific glycan class) is treated with an alpha 2,3 sialidase to liberate the non-reducing end sialic acid, the free sialic acid (non-reducing end glycan residual) can be measured. This signal would represent a larger portion of the thousands of altered glycan structures that are made in the disease state due to the altered expression of the alpha 2,3 sialyltransferase. Furthermore, in certain embodiments, depending on the signal (i.e., measurement) of the sialic acid liberated, a determination is made as to whether or not the accumulation of sialic acid is abnormal and/or whether or not such levels of accumulated sialic acid is associated with a disorder.

Another example of the process includes a method involving a biological sample containing glycans (purified or not) that is treated with an exo-glycosidase (for example a β-galactosidase). In some of such embodiments, enzymatic treatment cleaves non-reducing end monosaccharides within the chosen enzymes specificity (e.g., β-linked galactose residues) and liberates them as free monosaccharide (e.g., galactose). In various embodiments, the free monosaccharide is isolated and quantified by any analytical method (HPLC, MS, GC, etc), and any disease that presents changes in the levels of non-reducing end β-linked galactose residues is detected or diagnosed.

Similar methods are also optionally utilized in methods of monitoring and/or determining the therapeutic of a treatment or treatment regimen, particularly in the treatment of a disorder associated with abnormal glycan accumulation. For example, provided in certain embodiments herein is a method of monitoring the treatment of disorders associated with the abnormal degradation, biosynthesis and/or accumulation of glycans, the methods comprising:

a. following administration of an agent for treating a disorder associated with the abnormal degradation, biosynthesis and/or accumulation of glycans to an individual in need thereof, using an analytical instrument to measure the amount of a population of a non-reducing end glycan residue present in a transformed biological sample that has been prepared by: treating a population of glycans, in or isolated from a biological sample taken from the individual, with at least one normally functioning glycan degradation enzyme to liberate non-reducing end glycan residue;

b. determining whether or not the amount of liberated non-reducing end glycan residue has decreased or increased at a slower rate compared to the amount or rate of increase prior to administration of the agent for treating a disorder associated with the abnormal degradation, biosynthesis and/or accumulation of glycans.

In some embodiments, any process described herein comprises:

a. comparing an amount of a population of one or more glycan residual compound present in a transformed biological sample to an amount of a population of one or more glycan residual compound present in a control biological sample that has been treated in a manner substantially similar to the transformed biological sample.

In certain embodiments, a control biological sample utilized in any process described herein was provided from an individual that does not suffer from a disorder being diagnosed. In other embodiments, a control biological sample is taken from an individual suffering from a disorder being diagnosed. In certain embodiments, the result obtained from the control biological sample is stored in a database. In such cases a test sample is optionally compared to a plurality of control data in a database. Moreover in certain embodiments, any diagnostic process described herein is optionally utilized alone or in combination with other diagnostic techniques. Other diagnostic techniques include, by way of non-limiting example, symptom analysis, biopsies, detection of accumulation of other compounds in biological samples, or the like. In some embodiments, control biological samples are optionally taken from the same individual at substantially the same time, simply from a different location (e.g., one inflamed/arthritic synovial joint fluid vs the contralateral non-arthritic synovial joint). In other embodiments, control biological samples are optionally taken from the same individual at different points in time (e.g., before therapy and after therapy if the method being utilized is a method of monitoring a treatment therapy).

In some embodiments, provided herein is a method of monitoring the treatment of a disorder associated with the abnormal degradation, biosynthesis and/or accumulation of glycans, the method comprising:

a. following administration of an agent for treating a disorder associated with the abnormal degradation, biosynthesis and/or accumulation of glycans to an individual in need thereof, using an analytical instrument to measure the amount of a population of a biomarker comprising a non-reducing end glycan residual compounds present in a transformed biological sample, the biomarker being generated by treating a population of glycans, in or isolated from a biological sample from the individual, with at least one digesting glycan enzyme(s), wherein prior to enzyme treatment, the biomarker is not present in abundance in samples from individuals with the disease or condition relative to individuals without the disease or condition, and b. determining whether or not the amount of biomarker has decreased or increased at a slower rate compared to the amount or rate of increase prior to administration of the agent for treating a disorder associated with the abnormal degradation, biosynthesis and/or accumulation of glycans.

In some embodiments, the disorder associated with the abnormal degradation, biosynthesis and/or accumulation of glycans is a lysosomal storage disease, a cancerous disease, an inflammatory disease, an infectious disease, a central nervous system disease, or a cardiovascular disease.

In some embodiments, the normally functioning glycan degradation enzyme is a glycosidase, sulfatase, phosphorylase, deacetylase, or a combination thereof. In some embodiments, the normally functioning glycan degradation enzyme is a glycosidaseis selected from an exo-glycosidase and an endo-glycosidase. In some embodiments, the glycan residual compound is a monosaccharide, sulfate, phosphate, acetate, or a combination thereof. In some embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof.

In some embodiments, prior to measuring the amount of a population of non-reducing end glycan residual compounds, the non-reducing end glycan residual compounds are labeled with a detectable label. In some embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

Provided in certain embodiments herein are:

a. Methods using a non-reducing end (NRE) glycan biomarker along with at least one other glycan biomarkers (e.g., a non-reducing end glycan biomarker, a reducing end biomarker, and/or an internal glycan biomarker). In some instances, the use of the two biomarkers provides a very valuable tool that provides detailed information about disease severity and/or the response to therapy. In various aspects, the biomarkers detected and/or analyzed according to the processed described herein are compared in any suitable manner, e.g., in a ratio or simultaneous comparison.

b. Methods using at least two different glycan biomarkers (e.g., wherein each biomarker is individually selected from a non-reducing end glycan biomarker, a reducing end biomarker, and an internal glycan biomarker) to identifying or diagnosing diseases caused by deficiencies in the accumulation and/or biosynthesis of glycosaminoglycans.

In certain aspects, such methods comprise comparing the amounts of such biomarkers to each other. In specific embodiments, the comparison involves determining ratios of the biomarkers, wherein the biomarkers are glycan fragments generated by glycosaminoglycan lyase digestion.

Provided in certain embodiments herein is a method of diagnosing an individual as having a disease or condition associated with abnormal glycan biosynthesis, degradation, or accumulation, the method comprising:

a. generating a biomarker comprising of one or more non-reducing end glycan residual compound, wherein the biomarker is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition, and b. using an analytical instrument to detect the presence of and/or measure the amount of the biomarker produced and displaying or recording the presence of or a measure of a population of the biomarker;

wherein the presence of and/or measure the amount of the biomarker is utilized to determine the presence, identity, and/or severity of the disease or condition.

In some embodiments, the disease or disorder is caused by an abnormally functioning glycan degradation enzyme and wherein the abnormally functioning glycan degradation enzyme and the normally functioning glycan degradation enzyme are of the same type. In some embodiments, the abnormally functioning glycan degradation enzyme functions abnormally as a result of being present in an abnormally low amount, functioning improperly, or a combination thereof. In some embodiments, the abnormal glycan accumulation comprises the accumulation of abnormal amounts of glycans. In some embodiments, the abnormal glycan accumulation comprises the accumulation of abnormal amounts of normal glycans. In some embodiments, the abnormal glycan accumulation comprises the accumulation of abnormal amounts of abnormal glycans.

In some embodiments, the normally functioning glycan degradation enzyme is a glycosidase, sulfatase, phosphorylase, deacetylase, or a combination thereof. In some embodiments, the normally functioning glycan degradation enzyme is a glycosidase selected from an exo-glycosidase and an endo-glycosidase. In some embodiments, the glycosidase is an exo-glycosidase selected from the group consisting of a galactosidase, and a glucuronidase. In some embodiments, the glycan residual compound is a monosaccharide. In some embodiments, the glycan residual compound is sulfate, phosphate, acetate, or a combination thereof.

In some embodiments, a biological sample is purified prior to transforming a glycan thereof. In some embodiments, the process of purifying a biological sample comprises removing monosaccharides therefrom, removing sulfates therefrom, removing phosphates therefrom, removing acetate therefrom, or a combination thereof. In some embodiments, transforming a glycan of a biological sample with a normally functioning glycan degradation enzyme comprises transforming a glycan of a biological sample with a plurality of normally functioning glycan degradation enzymes. In some embodiments, the glycan is treated with a plurality of normally functioning glycan degradation enzymes concurrently, sequentially, or a combination thereof.

In some embodiments, the disorder associated with an abnormal glycan accumulation is MPS I, MPS II, MPS IIIA, MPS IVA, MPSVI, or Fabry Disease.

In some embodiments, determining whether the amount of liberated glycan residue is abnormal comprises labeling the glycan residue with a detectable label and measuring the amount of labeled glycan residue with an analytical instrument. In some embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

Provided herein, in certain embodiments, is a method of diagnosing an individual as having a disease or condition (e.g., associated with abnormal glycan biosynthesis, degradation, or accumulation), the method comprising:

a. generating a first biomarker comprising a glycan residual compound, wherein the first biomarker is generated by treating a population of glycans, in or isolated from a biological sample from the individual, with at least one digesting glycan enzyme, wherein prior to enzyme treatment, the first biomarker is not present in abundance in samples from individuals with the disease or condition relative to individuals without the disease or condition, b. generating a second biomarker comprising a glycan residual compound, wherein the second biomarker is generated by treating a population of glycans, in or isolated from a biological sample from the individual, with at least one digesting glycan enzyme in the same or different digestion step as provided in step (a), wherein prior to enzyme treatment, the second biomarker is not present in abundance in samples from individuals with the disease or condition relative to individuals without the disease or condition, c. using an analytical instrument to detect the presence of and/or measure the amount of the first and second biomarker produced and displaying or recording the presence of or a measure of a population of the first and second biomarkers, and d. monitoring and/or comparing the amounts of the first and second biomarkers in a biological sample;

wherein the presence of and/or measure of the amounts of the first and second biomarkers are utilized to determine the presence, identity, and/or severity of the disease or condition.

In some embodiments, the first biomarker is a non-reducing end glycan residual compound. In some embodiments, the disease or disorder is caused by an abnormally functioning glycan degradation enzyme and wherein the abnormally functioning glycan degradation enzyme and the digesting glycan enzyme are of the same type. In some embodiments, the non-reducing end glycan residual compound is a monosaccharide. In some embodiments, the non-reducing end glycan residual compound is not a monosaccharide.

In some embodiments, the second biomarker is derived or generated from the reducing end of the same glycan from which the first non-reducing end glycan residual compound biomarker was generated. In some embodiments, the second biomarker is derived or generated from the internal oligosaccharide structures of the same glycan from which the first non-reducing end glycan residual compound biomarker was generated. In some embodiments, the disease or disorder is caused by the abnormal function of a glycan degradation enzyme in the individual, and wherein the second biomarker can be generated by treating the first non-reducing end glycan residual compound biomarker with the glycan degradation enzyme that is functioning abnormally in the individual.

In some embodiments, the disease or condition associated with abnormal glycan biosynthesis, degradation, or accumulation is a lysosomal storage disease. In some embodiments, the lysosomal storage disease is Mucopolysaccharidosis. In some embodiments, the Mucopolysaccharidosis is MPS I, II, IIIA, IIIB, IIIC, IIID, IVA, IVB, VI, or VII. In some embodiments, the disease or condition associated with abnormal glycan biosynthesis, degradation, or accumulation is Metachromatic Leukodystrophy or Krabbe disease. In some embodiments, the disease or condition associated with abnormal glycan biosynthesis, degradation, or accumulation is Gangliosidosis. In some embodiments, the Gangliosidosis is Tay Sachs, Sandhoff, AB Variant, or GM-1 Gangliosidoses.

In some embodiments, the presence of and/or measure of the first non-reducing end glycan residual compound biomarker in combination with or in relation to the second biomarker is utilized to monitor the treatment of a disorder associated with the abnormal biosynthesis of glycans. In some embodiments, the presence of and/or measure of the first non-reducing end glycan residual compound biomarker in combination with or in relation to the second biomarker is utilized to monitor the treatment of a disorder associated with the abnormal degradation or accumulation of glycans. In some embodiments, the treatment is enzyme replacement therapy. In some embodiments, the absence of an increase in the second biomarker combined with a reduction in the non-reducing end glycan residual compound biomarker indicates a positive response to treatment of the disorder associated with abnormal degradation or accumulation of glycans.

Glycan Accumulation:

In various instances, glycan accumulation occurs in a biological sample as a result natural glycan biosynthetic and/or degradation processes. In some instances, abnormal glycan accumulation occurs in a biological sample as a result of a disorder or disease within an individual from which the biological sample is obtained.

In certain embodiments, abnormal glycan accumulation that is observable by methods described herein is associated with the accumulation of glycans in a manner that does not normally occur in individuals who are not in a disease state.

In some embodiments, such accumulation includes the accumulation of abnormal glycans. In certain instances, these abnormal glycans include glycans that are not normally produced in an individual, or a particular biological sample thereof, in the absence of a particular disease state. Therefore, in some embodiments, abnormal glycan accumulation includes the accumulation of glycans, the glycans being abnormal themselves, especially in any significant quantity. In other words, such glycans are abnormal glycans in individuals or particular biological samples thereof when such individuals are in a non-diseased, normal, or wild type state.

In some embodiments, such accumulation includes the abnormal accumulation of glycans. In some instances, these glycans are glycans that normally occur in individuals in a non-diseased state, but at lower or higher levels or are abnormal only due to the location wherein they are produced. Therefore, in some embodiments, abnormal glycan accumulation includes the accumulation of abnormal amounts of glycans or the location thereof, the glycans being normally occurring or abnormal glycans. In other words, the amount of glycan accumulation is abnormal in individuals, or particular biological samples thereof, when such individuals are in a non-diseased, normal, or wild type state.

Biological Sample:

Biological samples suitable for analysis according to the methods and processes described herein include, by way of non-limiting example, blood, serum, urine, hair, saliva, skin, tissue, plasma, cerebrospinal fluid (CSF), amniotic fluid, nipple aspirate, sputum, tears, lung aspirate, semen, feces, synovial fluid, nails, or the like. In specific embodiments, the biological samples suitable for analysis according to the methods and processes described herein include, by way of non-limiting example, urine, serum, plasma, or CSF. In certain embodiments, processes for detecting glycan in a sample comprise providing, from the individual, a test biological sample that comprises glycan. In some embodiments, providing a test biological sample from an individual includes obtaining the sample from the individual or obtaining the sample from another source (e.g., from a technician or institution that obtained the sample from the individual). In some embodiments, the biological sample is obtained from any suitable source, e.g., any tissue or cell (e.g., urine, serum, plasma, or CSF) of an individual. In certain embodiments, the tissue and/or cell from which the glycans are recovered is obtained from liver tissue or cells, brain tissue or cells, kidney tissue or cells, or the like.

In certain embodiments, a biological sample according to any process described herein is taken from any individual. In some embodiments, the individual is an individual suspected of suffering from a disorder associated with abnormal glycan accumulation, biosynthesis, and/or degradation. In certain embodiments, the individual is a newborn or fetus.

In some embodiments, provided herein is a composition comprising isolated glycans, wherein the glycans were isolated from a biological sample, and one or more glycan degradation enzyme. In certain embodiments, the composition further comprises one or more biomarker generated according to any method described herein (e.g., wherein the biomarker is a non-reducing end glycan residual compound). In certain embodiments, provided herein is a biomarker described herein (e.g., a labeled or non-labeled non-reducing end glycan residual compound) and an analytical instrument or chromatographic resin.

Degradation Enzymes:

In certain embodiments, any suitable enzyme is optionally utilized in order to remove a glycan residual compound from the non-reducing end of a glycan. In certain disorders, e.g., as described herein, various types of abnormal glycan accumulation occurs. In certain instances, this type of glycan accumulation is detected and/or measured utilizing any suitable enzyme, e.g., as described herein. For example, Tables 1-4 illustrate various enzymes that are utilized in various embodiments of the processes described herein. Any enzyme with the desired specificity is optionally utilized in any process herein (i.e., to liberate the non-reducing end structures). Enzymes suitable for use in the processes described herein include, by way of non-limiting example, eukaryotic, prokaryotic, native, or recombinant enzymes.

In certain embodiments, a disorder associated with abnormal glycan accumulation includes a disorder associated therewith is caused by an abnormally functioning glycan degradation enzyme. In various embodiments, the abnormally functioning glycan degradation enzyme functions abnormally as a result of being present in an abnormally low amount, functioning improperly, or a combination thereof. For example, an abnormally functioning glycan degradation enzyme functions abnormally as a result of being present in an amount of less than 50%, less than 40%, less than 30%, less than 20%, less than 10%, or less than 5% than is present in an individual with normal amounts of the glycan degradation enzyme (e.g., an individual in a non-diseased, normal, or wild type state). In further or alternative embodiments, abnormally functioning glycan degradation enzymes are present in a normal amount, but do not function properly in degrading glycans. For example, such enzymes may be have amino acid substitutions in the sequences thereof that reduce or eliminate the glycan degradative properties of the enzyme.

In some embodiments, wherein abnormal glycan accumulation results, at least partially from, an abnormally functioning glycan degradation enzyme, a normally functioning glycan degradation is optionally utilized, particularly wherein the abnormally functioning glycan degradation enzyme and the normally functioning glycan degradation enzyme are of the same type.

Normally functioning glycan degradation enzymes that are used in various embodiments described herein include, by way of non-limiting example, glycosidases, sulfatases, phosphorylases, deacetylases, sialidases, or combinations thereof. In more specific embodiments, a normally functioning glycan degradation enzyme is a glycosidase, e.g., an exo-glycosidase or an endo-glycosidase. In more specific embodiments, the glycosidase is an exo-glycosidase, e.g., galactosidase, and a glucuronidase. In some embodiments, such enzymes serve to remove various glycan residual compounds, such as, monosaccharides, sulfate, phosphate, acetate, sialic acid, or combinations thereof, which are detected and/or measured in methods described herein.

In certain embodiments, one or normally functioning glycan degradation enzyme is optionally utilized to liberate a targeted glycan residual compound. Multiple enzyme treatments of glycans within a biological sample are useful in various embodiments, e.g., wherein a particular enzyme is unable to liberate a targeted residual glycan compound without first modifying the non-reducing end of the glycan. For example, a first enzyme is optionally utilized to remove a sulfate so that a second enzyme can be utilized to remove a monosaccharide. In various embodiments, the glycans are treated with a plurality of normally functioning glycan degradation enzymes concurrently, sequentially, or a combination thereof.

Various enzymes that are used in various embodiments of the methods described herein include, by way of non-limiting example, a glycosidase. Non-limiting examples of glycosidase that are optionally utilized in the methods described herein include, by way of non-limiting example, enzymes categorized as 3.2.1.X by BRENDA (the comprehensive Enzyme Information System) including 3.2.1.1 alpha-amylase, 3.2.1.B1 extracellular agarase, 3.2.1.2 beta-amylase, 3.2.1.3 glucan 1,4-alpha-glucosidase, 3.2.1.4 cellulase, 3.2.1.5 licheninase, 3.2.1.6 endo-1,3(4)-beta-glucanase, 3.2.1.7 inulinase, 3.2.1.8 endo-1,4-beta-xylanase, 3.2.1.9 amylopectin-1,6-glucosidase, 3.2.1.10 oligo-1,6-glucosidase, 3.2.1.11 dextranase, 3.2.1.12 cycloheptaglucanase, 3.2.1.13 cyclohexaglucanase, 3.2.1.14 chitinase, 3.2.1.15 polygalacturonase, 3.2.1.16 alginase, 3.2.1.17 lysozyme, 3.2.1.18 exo-alpha-sialidase, 3.2.1.19 heparinase, 3.2.1.20 alpha-glucosidase, 3.2.1.21 beta-glucosidase, 3.2.1.22 alpha-galactosidase, 3.2.1.23 beta-galactosidase, 3.2.1.24 alpha-mannosidase, 3.2.1.25 beta-mannosidase, 3.2.1.26 beta-fructofuranosidase, 3.2.1.27 alpha-1,3-glucosidase, 3.2.1.28 alpha,alpha-trehalase, 3.2.1.29 chitobiase, 3.2.1.30 beta-D-acetylglucosaminidase, 3.2.1.31 beta-glucuronidase, 3.2.1.32 xylan endo-1,3-beta-xylosidase, 3.2.1.33 amylo-alpha-1,6-glucosidase, 3.2.1.34 chondroitinase, 3.2.1.35 hyaluronoglucosaminidase, 3.2.1.36 hyaluronoglucuronidase, 3.2.1.37 xylan 1,4-beta-xylosidase, 3.2.1.38 beta-D-fucosidase, 3.2.1.39 glucan endo-1,3-beta-D-glucosidase, 3.2.1.40 alpha-L-rhamnosidase, 3.2.1.41 pullulanase, 3.2.1.42 GDP-glucosidase, 3.2.1.43 beta-L-rhamnosidase, 3.2.1.44 fucoidanase, 3.2.1.45 glucosylceramidase, 3.2.1.46 galactosylceramidase, 3.2.1.47 galactosylgalactosylglucosylceramidase, 3.2.1.48 sucrose alpha-glucosidase, 3.2.1.49 alpha-N-acetylgalactosaminidase, 3.2.1.50 alpha-N-acetylglucosaminidase, 3.2.1.51 alpha-L-fucosidase, 3.2.1.52 beta-N-acetylhexosaminidase, 3.2.1.53 beta-N-acetylgalactosaminidase, 3.2.1.54 cyclomaltodextrinase, 3.2.1.55 alpha-N-arabinofuranosidase, 3.2.1.56 glucuronosyl-disulfoglucosamine glucuronidase, 3.2.1.57 isopullulanase, 3.2.1.58 glucan 1,3-beta-glucosidase, 3.2.1.59 glucan endo-1,3-alpha-glucosidase, 3.2.1.60 glucan 1,4-alpha-maltotetraohydrolase, 3.2.1.61 mycodextranase, 3.2.1.62 glycosylceramidase, 3.2.1.63 1,2-alpha-L-fucosidase, 3.2.1.64 2,6-beta-fructan 6-levanbiohydrolase, 3.2.1.65 levanase, 3.2.1.66 quercitrinase, 3.2.1.67 galacturan 1,4-alpha-galacturonidase, 3.2.1.68 isoamylase, 3.2.1.69 amylopectin 6-glucanohydrolase, 3.2.1.70 glucan 1,6-alpha-glucosidase, 3.2.1.71 glucan endo-1,2-beta-glucosidase, 3.2.1.72 xylan 1,3-beta-xylosidase, 3.2.1.73 licheninase, 3.2.1.74 glucan 1,4-beta-glucosidase, 3.2.1.75 glucan endo-1,6-beta-glucosidase, 3.2.1.76 L-iduronidase, 3.2.1.77 mannan 1,2-(1,3)-alpha-mannosidase, 3.2.1.78 mannan endo-1,4-beta-mannosidase, 3.2.1.79 alpha-L-arabinofuranoside hydrolase, 3.2.1.80 fructan beta-fructosidase, 3.2.1.81 beta-agarase, 3.2.1.82 exo-poly-alpha-galacturonosidase, 3.2.1.83 kappa-carrageenase, 3.2.1.84 glucan 1,3-alpha-glucosidase, 3.2.1.85 6-phospho-beta-galactosidase, 3.2.1.86 6-phospho-beta-glucosidase, 3.2.1.87 capsular-polysaccharide endo-1,3-alpha-galactosidase, 3.2.1.88 beta-L-arabinosidase, 3.2.1.89 arabinogalactan endo-1,4-beta-galactosidase, 3.2.1.90 arabinogalactan endo-1,3-beta-galactosidase, 3.2.1.91 cellulose 1,4-beta-cellobiosidase, 3.2.1.92 peptidoglycan beta-N-acetylmuramidase, 3.2.1.93 alpha,alpha-phosphotrehalase, 3.2.1.94 glucan 1,6-alpha-isomaltosidase, 3.2.1.95 dextran 1,6-alpha-isomaltotriosidase, 3.2.1.96 mannosylglycoprotein endo-beta-N-acetylglucosaminidase, 3.2.1.97 glycopeptide alpha-N-acetylgalactosaminidase, 3.2.1.98 glucan 1,4-alpha-maltohexaosidase, 3.2.1.99 arabinan endo-1,5-alpha-L-arabinosidase, 3.2.1.100 mannan 1,4-mannobiosidase, 3.2.1.101 mannan endo-1,6-alpha-mannosidase, 3.2.1.102 blood-group-substance endo-1,4-beta-galactosidase, 3.2.1.103 keratan-sulfate endo-1,4-beta-galactosidase, 3.2.1.104 steryl-beta-glucosidase, 3.2.1.105 3alpha(S)-strictosidine beta-glucosidase, 3.2.1.106 mannosyl-oligosaccharide glucosidase, 3.2.1.107 protein-glucosyl-galactosylhydroxylysine glucosidase, 3.2.1.108 lactase, 3.2.1.109 endogalactosaminidase, 3.2.1.110 mucinaminyl-serine mucinaminidase, 3.2.1.111 1,3-alpha-L-fucosidase, 3.2.1.112 2-deoxyglucosidase, 3.2.1.113 mannosyl-oligosaccharide 1,2-alpha-mannosidase, 3.2.1.114 mannosyl-oligosaccharide 1,3-1,6-alpha-mannosidase, 3.2.1.115 branched-dextran exo-1,2-alpha-glucosidase, 3.2.1.116 glucan 1,4-alpha-maltotriohydrolase, 3.2.1.117 amygdalin beta-glucosidase, 3.2.1.118 prunasin beta-glucosidase, 3.2.1.119 vicianin beta-glucosidase, 3.2.1.120 oligoxyloglucan beta-glycosidase, 3.2.1.121 polymannuronate hydrolase, 3.2.1.122 maltose-6'-phosphate glucosidase, 3.2.1.123 endoglycosylceramidase, 3.2.1.124 3-deoxy-2-octulosonidase, 3.2.1.125 raucaffricine beta-glucosidase, 3.2.1.126 coniferin beta-glucosidase, 3.2.1.127 1,6-alpha-L-fucosidase, 3.2.1.128 glycyrrhizinate beta-glucuronidase, 3.2.1.129 endo-alpha-sialidase, 3.2.1.130 glycoprotein endo-alpha-1,2-mannosidase, 3.2.1.131 xylan alpha-1,2-glucuronosidase, 3.2.1.132 chitosanase, 3.2.1.133 glucan 1,4-alpha-maltohydrolase, 3.2.1.134 difructose-anhydride synthase, 3.2.1.135 neopullulanase, 3.2.1.136 glucuronoarabinoxylan endo-1,4-beta-xylanase, 3.2.1.137 mannan exo-1,2-1,6-alpha-mannosidase, 3.2.1.138 anhydrosialidase, 3.2.1.139 alpha-glucuronidase, 3.2.1.140 lacto-N-biosidase, 3.2.1.141 4-alpha- D-{(1->4)-alpha-D-glucano}trehalose trehalohydrolase, 3.2.1.142 limit dextrinase, 3.2.1.143 poly(ADP-ribose) glycohydrolase, 3.2.1.144 3-deoxyoctulosonase, 3.2.1.145 galactan 1,3-beta-galactosidase, 3.2.1.146 beta-galactofuranosidase, 3.2.1.147 thioglucosidase, 3.2.1.148 ribosylhomocysteinase, 3.2.1.149 beta-primeverosidase, 3.2.1.150 oligoxyloglucan reducing-end-specific cellobiohydrolase, 3.2.1.151 xyloglucan-specific endo-beta-1,4-glucanase, 3.2.1.152 mannosylglycoprotein endo-beta-mannosidase, 3.2.1.153 fructan beta-(2,1)-fructosidase, 3.2.1.154 fructan beta-(2,6)-fructosidase, 3.2.1.155 xyloglucan-specific exo-beta-1,4-glucanase, 3.2.1.156 oligosaccharide reducing-end xylanase, 3.2.1.157 iota-carrageenase 3.2.1.158 alpha-agarase, 3.2.1.159 alpha-neoagaro-oligosaccharide hydrolase, 3.2.1.160 xyloglucan-specific exo-beta-1,4-glucanase, 3.2.1.161 beta-apiosyl-beta-glucosidase, 3.2.1.162 lambda-carrageenase, 3.2.1.163 1,6-alpha-D-mannosidase, 3.2.1.164 galactan endo-1,6-beta-galactosidase, 3.2.1.165 exo-1,4-beta-D-glucosaminidase, or a combination thereof.

Other enzymes that are used in various embodiments of the methods described herein include, by way of non-limiting example, a sulfatase including, e.g., enzymes categorized as 3.1.6.X by BRENDA (the comprehensive Enzyme Information System) including 3.1.6.1 arylsulfatase, 3.1.6.2 steryl-sulfatase, 3.1.6.3 glycosulfatase, 3.1.6.4 N-acetylgalactosamine-6-sulfatase, 3.1.6.5 sinigrin sulfohydrolase; myrosulfatase, 3.1.6.6 choline-sulfatase, 3.1.6.7 cellulose-polysulfatase, 3.1.6.8 cerebroside-sulfatase, 3.1.6.9 chondro-4-sulfatase, 3.1.6.10 chondro-6-sulfatase, 3.1.6.11 di sulfoglucosamine-6-sulfatase, 3.1.6.12 N-acetylgalactosamine-4-sulfatase, 3.1.6.13 iduronate-2-sulfatase, 3.1.6.14 N-acetylglucosamine-6-sulfatase, 3.1.6.15 N-sulfoglucosamine-3-sulfatase, 3.1.6.16 monomethyl-sulfatase, 3.1.6.17 D-lactate-2-sulfatase, 3.1.6.18 glucuronate-2-sulfatase, 3.10.1.1 N-sulfoglucosamine sulfohydrolase, or combinations thereof.

Certain enzymes that are used in various embodiments of the methods described herein include, by way of non-limiting example, a deacetylase, e.g., an exo-deacetylase, including, by way of non-limiting example, the alpha-glucosaminide N-acetyltransferase (2.3.1.78) or similar enzymes.

Certain enzymes that are used in various embodiments of the methods described herein include, by way of non-limiting example, a carbohydrate phosphatase including, e.g., 3.1.3.1 alkaline phosphatase, 3.1.3.2 acid phosphatase, 3.1.3.B2 diacylglycerol pyrophosphate phosphatase, 3.1.3.3 phosphoserine phosphatase, 3.1.3.4 phosphatidate phosphatase, 3.1.3.5 5'-nucleotidase, 3.1.3.6 3'-nucleotidase, 3.1.3.7 3'(2'),5'-bisphosphate nucleotidase, 3.1.3.8 3-phytase, 3.1.3.9 glucose-6-phosphatase, 3.1.3.10 glucose-1-phosphatase, 3.1.3.11 fructose-bisphosphatase, 3.1.3.12 trehalose-phosphatase, 3.1.3.13 bisphosphoglycerate phosphatase, 3.1.3.14 methylphosphothioglycerate phosphatase, 3.1.3.15 histidinol-phosphatase, 3.1.3.16 phosphoprotein phosphatase, 3.1.3.17 [phosphorylase] phosphatase, 3.1.3.18 phosphoglycolate phosphatase, 3.1.3.19 glycerol-2-phosphatase, 3.1.3.20 phosphoglycerate phosphatase, 3.1.3.21 glycerol-1-phosphatase, 3.1.3.22 mannitol-1-phosphatase, 3.1.3.23 sugar-phosphatase, 3.1.3.24 sucrose-phosphate phosphatase, 3.1.3.25 inositol-phosphate phosphatase, 3.1.3.26 4-phytase, 3.1.3.27 phosphatidylglycerophosphatase, 3.1.3.28 ADP-phosphoglycerate phosphatase, 3.1.3.29 N-acylneuraminate-9-phosphatase, 3.1.3.30 3'-phosphoadenylylsulfate 3'-phosphatase, 3.1.3.31 nucleotidase, 3.1.3.32 polynucleotide 3'-phosphatase, 3.1.3.33 polynucleotide 5'-phosphatase, 3.1.3.34 deoxynucleotide 3'-phosphatase, 3.1.3.35 thymidylate 5'-phosphatase, 3.1.3.36 phosphoinositide 5-phosphatase, 3.1.3.37 sedoheptulose-bisphosphatase, 3.1.3.38 3-phosphoglycerate phosphatase, 3.1.3.39 streptomycin-6-phosphatase, 3.1.3.40 guanidinodeoxy-scyllo-inositol-4-phosphatase, 3.1.3.41 4-nitrophenylphosphatase, 3.1.3.42 [glycogen-synthase-D] phosphatase, 3.1.3.43 [pyruvate dehydrogenase (acetyl-transferring)]-phosphatase, 3.1.3.44 [acetyl-CoA carboxylase]-phosphatase, 3.1.3.45 3-deoxy-manno-octulosonate-8-phosphatase, 3.1.3.46 fructose-2,6-bisphosphate 2-phosphatase, 3.1.3.47 [hydroxymethylglutaryl-CoA reductase (NADPH)]-phosphatase, 3.1.3.48 protein-tyrosine-phosphatase, 3.1.3.49 [pyruvate kinase]-phosphatase, 3.1.3.50 sorbitol-6-phosphatase, 3.1.3.51 dolichyl-phosphatase, 3.1.3.52 [3-methyl-2-oxobutanoate dehydrogenase (2-methylpropanoyl-transferring)]-phosphatase, 3.1.3.53 [myosin-light-chain] phosphatase, 3.1.3.54 fructose-2,6-bisphosphate 6-phosphatase, 3.1.3.55 caldesmon-phosphatase, 3.1.3.56 inositol-polyphosphate 5-phosphatase, 3.1.3.57 inositol-1,4-bisphosphate 1-phosphatase, 3.1.3.58 sugar-terminal-phosphatase, 3.1.3.59 alkylacetylglycerophosphatase, 3.1.3.60 phosphoenolpyruvate phosphatase, 3.1.3.61 inositol-1,4,5-trisphosphate 1-phosphatase, 3.1.3.62 multiple inositol-polyphosphate phosphatase, 3.1.3.63 2-carboxy-D-arabinitol-1-phosphatase, 3.1.3.64 phosphatidylinositol-3-phosphatase, 3.1.3.65 inositol-1,3-bisphosphate 3-phosphatase, 3.1.3.66 phosphatidylinositol-3,4-bisphosphate 4-phosphatase, 3.1.3.67 phosphatidylinositol-3,4,5-trisphosphate 3-phosphatase, 3.1.3.68 2-deoxyglucose-6-phosphatase, 3.1.3.69 glucosylglycerol 3-phosphatase, 3.1.3.70 mannosyl-3-phosphoglycerate phosphatase, 3.1.3.71 2-phosphosulfolactate phosphatase, 3.1.3.72 5-phytase, 3.1.3.73 alpha-ribazole phosphatase, 3.1.3.74 pyridoxal phosphatase, 3.1.3.75 phosphoethanolamine/phosphocholine phosphatase, 3.1.3.76 lipid-phosphate phosphatase, 3.1.3.77 acireductone synthase, 3.1.3.78 phosphatidylinositol-4,5-bisphosphate 4-phosphatase, or 3.1.3.79 mannosyl-fructose-phosphate phosphatase, or a combination thereof.

In some embodiments, processes described herein include incubation and digestion with a first enzyme to clear a specific non-reducing end structure, incubation and digestion with a second enzyme. In certain embodiments, this multi-enzyme approach is useful in order to reduce the background. For example, in MPS II treating the sample with an iduronidase and/or glucuronidase to clear all non-sulfated non-reducing end uronic acids (this enzyme will not cleave sulfated iduronic acids) before 2-O sulfatase treatment. This approach will clear all non-sulfated non-reducing end uronic acids so that upon desulfation with the 2-O sulfatase the newly releasable uronic acids will be those that were previously sulfated (and therefore resistant to the action of the iduronidase and/or glucuronidase).

Glycan Residual Compounds:

Glycan residual compounds detected, measured, analyzed, and/or otherwise characterized according to any process described herein include any suitable glycan residue that is liberated from the non-reducing end of a glycan (e.g., a glycan obtained from a biological sample of an individual). In specific instances, glycan residual compounds including, e.g., oligosaccharides, monosaccharides, sulfate, phosphate, sialic acid, acetate, or the like.

Specific glycan residual compounds useful in any process herein are described in Tables 1-4.

In some embodiments, the generated biomarker is a glycan residual compound. In some embodiments, the glycan residual compound is a monosaccharide. In certain embodiments, the glycan residual compound is sulfate, phosphate, acetate, or a combination thereof. In certain embodiments, the glycan residual compound has a molecular weight of less than 2000 g/mol, less than 1500 g/mol, less than 1000 g/mol, less than 500 g/mol, less than 400 g/mol, less than 300 g/mol, less than 260 g/mol, less than 200 g/mol, less than 100 g/mol, or the like (e.g., prior to tagging with any detectable label that may be included in a process described herein).

Biomarker Ratios:

In various aspects provided herein, the simultaneous measurement or ratios of various biomarkers (e.g., saturated non-reducing end structures or internal unsaturated disaccharides generated by enzymatic depolymerization of glycosaminoglycans) reveals information about disease severity and response to therapy. Depending on the specific disease being diagnosed or otherwise analyzed, these comparisons (e.g., simultaneous measurement or ratios) use varying saturated and unsaturated structures.

For example, in some embodiments, one or more of the biomarkers used in any process described herein includes one of the saturated biomarkers (glycan fragments) set forth in Table 1. In specific embodiments, the disorder being diagnosed or otherwise analyzed is MPS I. In some embodiments, the first and second biomarkers are biomarkers of Table 1. In other embodiments, the first biomarker is a biomarker of Table 1 and the second biomarker is a biomarker of Table 9, 3, 4, or 6. In further or alternative embodiments, both the first and second biomarkers are from Table 1.

TABLE 1

| HS derived | CS/DS derived |
|---|---|
| IdoA-GlcNS | IdoA-GalNAc4S |
| IdoA-GlcNS6S | IdoA-GalNAc6S |
| IdoA-GlcNAc | IdoA-GalNAc |
| IdoA-GlcNAc6S | IdoA-GalNAc4S6S |

In further embodiments, one or more of the biomarkers used in any process described herein includes one of the saturated biomarkers (glycan fragments) set forth in Table 2. In specific embodiments, the disorder being diagnosed or otherwise analyzed is MPS II. In some embodiments, the first biomarker is a biomarker of Table 2 and the second biomarker is a biomarker of Table 1. In other embodiments, the first biomarker is a biomarker of Table 2 and the second biomarker is a biomarker of Table 9. In further or alternative embodiments, both the first and second biomarkers are from Table 2.

TABLE 2

| HS derived | CS/DS derived |
|---|---|
| IdoA2S-GlcNS | IdoA2S-GalNAc4S |
| IdoA2S-GlcNS6S | IdoA2S-GalNAc6S |
| IdoA2S-GlcNAc | IdoA2S-GalNAc |
| IdoA2S-GlcNAc6S | IdoA2S-GalNAc4S6S |

In further embodiments, one or more of the biomarkers used in any process described herein includes one of the saturated biomarkers (glycan fragments) set forth in Table 3. In specific embodiments, the disorder being diagnosed or otherwise analyzed is MPS IIIA. In some embodiments, the first biomarker is a biomarker of Table 3 and the second biomarker is a biomarker of Table 5. In other embodiments, the first biomarker is a biomarker of Table 3 and the second biomarker is a biomarker of Table 9. In further or alternative embodiments, both the first and second biomarkers are from Table 3.

TABLE 3

| HS derived |
|---|
| GlcNS |
| GlcNS+/−6S-UA+/−2S-GlcNAc+/−6S |
| GlcNS+/−6S-UA+/−2S-GlcNS+/−6S |

In further embodiments, one or more of the biomarkers used in any process described herein includes one of the saturated biomarkers (glycan fragments) set forth in Table 4. In specific embodiments, the disorder being diagnosed or otherwise analyzed is MPS IIIB In some embodiments, the first biomarker is a biomarker of Table 4 and the second biomarker is a biomarker of Table 1, 2, or 8. In other embodiments, the first biomarker is a biomarker of Table 4 and the second biomarker is a biomarker of Table 9. In further or alternative embodiments, both the first and second biomarkers are from Table 4.

TABLE 4

| HS derived |
|---|
| GlcNAc |
| GlcNAc-UA+/−2S-GlcNAc+/−6S |
| GlcNAc-UA+/−2S-GlcNS+/−6S |

In further embodiments, one or more of the biomarkers used in any process described herein includes one of the saturated biomarkers (glycan fragments) set forth in Table 5. In specific embodiments, the disorder being diagnosed or otherwise analyzed is MPS IIIC. In some embodiments, the first biomarker is a biomarker of Table 5 and the second biomarker is a biomarker of Table 4. In other embodiments, the first biomarker is a biomarker of Table 5 and the second biomarker is a biomarker of Table 9. In further or alternative embodiments, both the first and second biomarkers are from Table 5.

TABLE 5

| HS derived |
|---|
| GlcN |
| GlcN+/−6S-UA+/−2S-GlcNAc+/−6S |
| GlcN+/−6S-UA+/−2S-GlcNS+/−6S |

In further embodiments, one or more of the biomarkers used in any process described herein includes one of the saturated biomarkers (glycan fragments) set forth in Table 6. In specific embodiments, the disorder being diagnosed or otherwise analyzed is MPS IIID In some embodiments, the first biomarker is a biomarker of Table 6 and the second biomarker is a biomarker of Table 4 or 5. In other embodiments, the first biomarker is a biomarker of Table 6 and the second biomarker is a biomarker of Table 9. In further or alternative embodiments, both the first and second biomarkers are from Table 6.

TABLE 6

| HS derived |
| --- |
| GlcN6S |
| GlcNAc6S |
| GlcN6S-UA+/−2S-GlcNAc+/−6S |
| GlcNAc6S-UA+/−2S-GlcNAc+/−6S |
| GlcN6S-UA+/−2S-GlcNS+/−6S |
| GlcNAc6S-UA+/−2S-GlcNS+/−6S |

In further embodiments, one or more of the biomarkers used in any process described herein includes one of the saturated biomarkers (glycan fragments) set forth in Table 7. In specific embodiments, the disorder being diagnosed or otherwise analyzed is MPS VI. In some embodiments, the first biomarker is a biomarker of Table 7 and the second biomarker is a biomarker of Table 8. In other embodiments, the first biomarker is a biomarker of Table 7 and the second biomarker is a biomarker of Table 9. In further or alternative embodiments, both the first and second biomarkers are from Table 7.

TABLE 7

| CS derived |
| --- |
| GalNAc4S |
| GalNAc4S-UA-GalNAc |
| GalNAc4S-UA-GalNAc4S |
| GalNAc4S-UA-GalNAc6S |
| GalNAc4S-UA-GalNAc4S6S |
| GalNAc4S-UA2S-GalNAc |
| GalNAc4S-UA2S-GalNAc4S |
| GalNAc4S-UA2S-GalNAc6S |
| GalNAc4S-UA2S-GalNAc4S6S |

In further embodiments, one or more of the biomarkers used in any process described herein includes one of the saturated biomarkers (glycan fragments) set forth in Table 8. In specific embodiments, the disorder being diagnosed or otherwise analyzed is MPS VII. In some embodiments, the first biomarker is a biomarker of Table 8 and the second biomarker is a biomarker of Table 3, 4, 6, or 7. In other embodiments, the first biomarker is a biomarker of Table 8 and the second biomarker is a biomarker of Table 9. In further or alternative embodiments, both the first and second biomarkers are from Table 1.

TABLE 8

| HS derived | CS derived | KS derived |
| --- | --- | --- |
| GlcA-GlcNAc | GlcA-GalNAc | Gal-GlcNAc |
| GlcA-GlcNS | GlcA-GalNAc4S | Gal-GlcNAc6S |
| GlcA-GlcNAc6S | GlcA-GalNAc6S | Gal6S-GlcNAc |
| GlcA-GlcNS6S | GlcA-GalNAc4S6S | Gal6S-GlcNAc6S |
| | | GlcNAc-Gal |
| | | GlcNAc-Gal6S |
| | | GlcNAc6S-Gal |
| | | GlcNAc6S-Gal6S |

In further embodiments, one or more of the biomarkers used in any process described herein includes one of the unsaturated biomarkers (glycan fragments) set forth in Table 9. In further or alternative embodiments, both the first and second biomarkers are from Table 9.

TABLE 9

| HS derived | CS derived |
| --- | --- |
| ΔUA-GlcN | ΔUA-GalNAc |
| ΔUA-GlcN6S | ΔUA-GalNAc4S |
| ΔUA2S-GlcN | ΔUA-GalNAc6S |
| ΔUAS-GlcN6S | ΔUA2S-GalNAc |
| ΔUA-GlcNAc | ΔUA2S-GalNAc4S |
| ΔUA-GlcNAc6S | ΔUA2S-GalNAc6S |
| ΔUA2S-GlcNAc | ΔUA-GalNAc4S6S |
| ΔUA2S-GlcNAc6S | ΔUA2S-GalNAc4S6S |
| ΔUA-GlcNS | |
| ΔUA-GlcNS6S | |
| ΔUA-GlcNS3S | |
| ΔUA2S-GlcNS | |
| ΔUA2S-GlcNS6S | |
| ΔUA2S-GlcNS3S | |
| ΔUA-GlcNS6S3S | |
| ΔUA2S-GlcNS6S3S | |

In further embodiments, one or more of the biomarkers used in any process described herein includes one of the saturated biomarkers (glycan fragments) set forth in Table 10. In specific embodiments, the disorder being diagnosed or otherwise analyzed is MPS IVA. In some embodiments, the first biomarker is a biomarker of Table 10 and the second biomarker is a biomarker of Table 8. In other embodiments, the first biomarker is a biomarker of Table 10 and the second biomarker is a biomarker of Table 9. In further or alternative embodiments, both the first and second biomarkers are from Table 10.

TABLE 10

| KS derived | CS Derived |
| --- | --- |
| Gal6S | GalNAc6S |
| Gal6S-GlcNAc | GalNAc6S4S |
| Gal6S-GlcNAc6S | GalNAc6S-UA-GalNAc |
| Gal6S-GlcNAc-Gal | GalNAc6S-UA-GalNAc4S |
| Gal6S-GlcNAc-Gal6S | GalNAc6S-UA-GalNAc6S |
| Gal6S-GlcNAc6S-Gal | GalNAc6S-UA-GalNAc4S6S |
| Gal6S-GlcNAc6S-Gal6S | GalNAc6S-UA2S-GalNAc |
| | GalNAc6S-UA2S-GalNAc4S |
| | GalNAc6S-UA2S-GalNAc6S |
| | GalNAc6S-UA2S-GalNAc4S6S |
| | GalNAc6S4S-UA-GalNAc |
| | GalNAc6S4S-UA-GalNAc4S |
| | GalNAc6S4S-UA-GalNAc6S |
| | GalNAc6S4S-UA-GalNAc4S6S |
| | GalNAc6S4S-UA2S-GalNAc |
| | GalNAc6S4S-UA2S-GalNAc4S |
| | GalNAc6S4S-UA2S-GalNAc6S |
| | GalNAc6S4S-UA2S-GalNAc4S6S |

In further embodiments, one or more of the biomarkers used in any process described herein includes one of the saturated biomarkers (glycan fragments) set forth in Table 11. In specific embodiments, the disorder being diagnosed or otherwise analyzed is MPS IVB. In some embodiments, the first biomarker is a biomarker of Table 11 and the second biomarker is a biomarker of Table 8. In other embodiments, the first biomarker is a biomarker of Table 11 and the second biomarker is a biomarker of Table 9. In further or alternative embodiments, both the first and second biomarkers are from Table 11.

TABLE 11

| KS derived | CS Derived | Glyco-lipid derived |
|---|---|---|
| Gal | GalNAc | Gal-GalNAc-Gal-Glu |
| Gal-GlcNAc | GalNAc4S | Gal-GalNAc-Gal-Glu + 1Sialic acid |
| Gal-GlcNAc6S | GalNAc-UA-GalNAc | Gal-GalNAc-Gal-Glu + 2 Sialic acids |
| Gal-GlcNAc-Gal | GalNAc-UA-GalNAc4S | Gal-GalNAc-Gal-Glu + 3 Sialic acids |
| Gal-GlcNAc-Gal6S | GalNAc-UA-GalNAc6S | |
| Gal-GlcNAc6S-Gal | GalNAc-UA-GalNAc4S6S | |
| Gal-GlcNAc6S-Gal6S | GalNAc-UA2S-GalNAc | |
| | GalNAc-UA2S-GalNAc4S | |
| | GalNAc-UA2S-GalNAc6S | |
| | GalNAc-UA2S-GalNAc4S6S | |
| | GalNAc4S-UA-GalNAc | |
| | GalNAc4S-UA-GalNAc4S | |
| | GalNAc4S-UA-GalNAc6S | |
| | GalNAc4S-UA-GalNAc4S6S | |
| | GalNAc4S-UA2S-GalNAc | |
| | GalNAc4S-UA2S-GalNAc4S | |
| | GalNAc4S-UA2S-GalNAc6S | |
| | GalNAc4S-UA2S-GalNAc4S6S | |

As used herein, IdoA and ◆ are iduronic acid (e.g., α-L-iduronic acid) saccharide residues. As used herein, GlcA and ◆ are glucuronic acid (e.g., β-L-glucuronic acid) saccharide residues. As used herein, ◇ are unsaturated uronic acids (UA), such as IdoA and GlcA. As used herein, GlcN and ◼ are glucosamine (e.g., 2-deoxy-2-amino-β-D-glucopyranosyl) saccharide residues. As used herein, GlcN(Ac)1 and ▦ are a glucosamine (e.g., 2-deoxy-2-amino-β-D-glucopyranosyl) saccharide residue wherein the 2-amino group is acetylated. As used herein, Gal and ○ is a galactose saccharide residue. In various specific instances, iduronic acid, glucuronic acid, glucosamine, and/or galactose saccharide residues are saturated at 4 and 5 carbons of the non-reducing end saccharide residue, or are free of carbon-carbon unsaturation. In other instances, any one or more of the saccharide residues is unsaturated, e.g., at the 4 and 5 carbon positions of the saccharide residue at the non-reducing end of an oligosaccharide provided herein. The symbolic nomenclature used herein follows the "Symbol and Text Nomenclature for Representation of Glycan Structure" as promulgated by the Nomenclature Committee for the Consortium for Functional Glycomics, as amended on October 2007.

As an illustrative example of non-reducing end saccharide residues that are saturated and unsaturated at the C4 and C5 positions, an L-iduronic acid (IdoA) residue that is saturated at the C4 and C5 positions has a structure as follows:

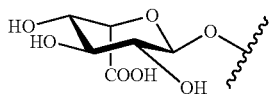

whereas an L-iduronic acid (IdoA) residue at the non-reducing end of the oligosaccharide that is unsaturated at the C4 and C5 positions may have a structure as follows:

or the like. Oligosaccharides having non-reducing end saccharide residues that are saturated at the C4 and C5 position are referred to herein as "C4-C5 non-reducing end saturated oligosaccharides".

Ratios of NRE Biomarkers:

In certain embodiments, a method provided for herein comprises comparing a first biomarker that is an NRE biomarker to a second biomarker that is a different NRE biomarker. In some embodiments, the first biomarker is specific to a particular disease (e.g., MPS disease or other disease associated with altered GAG synthesis or degradation). In certain embodiments, the second biomarker is an NRE biomarker that would not be expected for the particular disease (e.g., according to the tables provided herein).

In some embodiments, a method described herein is used in concert with an ERT therapy. In some of such embodiments, the method is utilized to monitor the efficacy of an ERT therapy.

In certain aspects, by examining the ratio of abundance of a disease specific NRE(s) to the NRE(s) that are generated after the action of an enzyme replacement therapy (ERT) in use, one can verify that the ERT is acting in the desired cellular compartment (the lysosome). In some instances, this is important in order to ensure that a reduction in the glycan substrate in response to treatment reflects the beneficial action of the ERT in the lysosome or the non-therapeutically beneficial action of the enzyme outside of the lysosome. This is especially important in therapeutic approaches that require sampling fluids for biomarker analysis through the same port that the ERT was delivered—such as intrathecal delivery of ERT. If the ERT is acting outside of the cell (in blood, CSF, or in a sampling port) the subsequent lysosomal enzymes will not efficiently degrade the resulting glycan.

This leads to the elimination of the disease specific NRE and generation of a NRE typically associated with a different disease.

For example, in one specific embodiment, the disease being diagnosed or otherwise analyzed is MPS II. In some of such instances, the first biomarker is an MPS II disease specific NRE biomarker, such as IdoA2S-GlcN(+/−NS, +/−6S). If the ERT (2-sulfatase) acts in the lysosome, this NRE is 2-O desulfated producing IdoA-GlcN(+/−NS, +/−6S) which is rapidly eliminated by the subsequent lysosomal enzymes that are functional in MPS II patients. In contrast, if the ERT acts outside of the lysosome, the first biomarker (the MPS II NRE biomarker) [IdoA2S-GlcN(+/−NS, +/−6S)] is eliminated and the second biomarker (e.g., an MPS I NRE, such as [IdoA-GlcN(+/−NS, +/−6S)]) is generated (the extracellular action NRE, EANRE). In some instances, because the other lysosomal enzymes are not present in significant active quantities outside of the lysosome, the MPS I markers are stable. In some cases the NREs can be converted to other NRE structures through the action of other endogenous enzymes. In some aspects, using such techniques and by simultaneous monitoring of the MPS II and MPS I NREs, the severity of disease and specific response to therapy are determined. Similar methods for the other MPS disorders, or any other disorder involving abnormal glycan accumulation, biosynthesis, and/or degradation are contemplated herein.

In exemplary embodiments, the generation of an MPS I NRE biomarker in an MPS II patient after ERT treatment indicates that the ERT is not effectively acting in the lysosome. In various aspects, the disease specific NRE and EANRE ratios that are relevant to each disease are different for each disease class dependent on the NRE of the target disease and the relevant EANREs that are generated by the ERT. In specific exemplary embodiments methods described herein utilize the following specific first and second biomarkers when utilized with the denoted disease:

MPS I
   Disease specific NREs (saturated fragments)
      Disaccharides IdoA-GlcN(+/−NS, +/−6S)
   EANREs
      Mono and trisaccharides from the MPS IIIA and MPS IIIB family MPS II
   Disease specific NREs (saturated fragments)
      Disaccharides IdoA2S-GlcN(+/−NS, +/−6S)
   EANREs
      Disaccharides from the MPS I family MPS IIIA
   Disease specific NREs (saturated fragments)
      Trisaccharides: GlcNS-GlcA/IdoA(+/−2S)-GlcN(+/−NS, +/−6S)
   EANREs
      Disaccharides from the MPS IIIC family MPS IIIB
   Disease specific NREs (saturated fragments)
      Trisaccharides: GlcNAc-GlcA/IdoA(+/−2S)-GlcN(+/−NS, +/−6S)
   EANREs
      Disaccharides from the MPS I, II and VII families MPS IIIC
   Disease specific NREs (saturated fragments)
      Trisaccharides: GlcN-GlcA/IdoA(+/−2S)-GlcN(+/−NS, +/−6S)
   EANREs
      Disaccharides from the MPS IIIB family MPS IIID
   Disease specific NREs (saturated fragments)
      Trisaccharides: GlcN(+/−NS)6S-GlcA/IdoA(+/−2S)-GlcN(+/−NS, +/−6S)
   EANREs
      Disaccharides from the MPS IIIA and IIIB families MPS IVA
   Disease specific NREs (saturated fragments)
      KS derived mono-, di, and trisaccharides: Gal6S, Gal6S-GlcNAc(+/−6S), Gal6S-UA(+/−2S)-Gal(+/−6S)
      CS derived mono-, di, and trisaccharides: GalNAc6S(+/−4S), GalNAc6S(+/−4S)-UA(+/−2S)-GalNAc(+/−4S, +/−6S)
   EANREs
      Mono and disaccharides from the MPS IVB family MPS VI
   Disease specific NREs (saturated fragments)
      CS derived mono and trisaccharides: GalNAc4S, GalNAc4S-UA(+/−2S)-GalNAc(+/−4S, +/−6S)
   EANREs
      NREs from hexosaminindase deficiencies MPS VII
   Disease specific NREs (saturated fragments)
      Disaccharides: GlcA-GlcN(+/−NS, +/−6S)
   EANREs
      Disaccharides from the MPS IIIA, IIIB, and IIID families Ratios of NRE and Non-NRE Biomarkers:

In certain embodiments, a method provided for herein comprises comparing a first biomarker that is an NRE biomarker to a second biomarker that is a non-NRE biomarker (e.g., a reducing end or internal glycan residual biomarker). In some embodiments, the first biomarker is specific to a particular disease (e.g., MPS disease). In specific embodiments, the second biomarker is an internal biomarker (e.g., from Table 9). In more specific embodiments, such methods are utilized in combination with a therapy for the treatment of a disorder associated with abnormal glycan biosynthesis, degradation, and/or accumulation.

In certain embodiments, the second biomarker is a non-NRE marker (e.g., rather than an EANRE discussed above). Because the non-therapeutic action of the ERT only eliminates the specific NRE structure, but does not reduce the level of the accumulating glycan, ratios of the disease specific NRE to other non-NRE structures can also be used to determine the site of action of the ERT.

In an exemplary embodiment, wherein the disease being diagnosed or otherwise analyzed is MPS II, a disease specific NRE is IdoA2S-GlcN(+/−NS, +/−6S). If the ERT (2-sulfatase) acts in the lysosome, this NRE is 2-O desulfated producing a GAG fragment that terminates with IdoA-GlcN(+/−NS, +/−6S). That fragment is rapidly eliminated by the subsequent lysosomal enzymes that are functional in MPS II patients. In contrast, if the ERT acts outside of the lysosome, the abundance of internal HS fragments liberated by lyase digestion remain constant. Therefore, by simultaneous monitoring of the MPS II and internal HS derived structures such as ΔUA-GlcNAc or ΔUA-GlcNS the true lysosomal activity of the treatment can be measured.

In some embodiments, a method described herein is utilized to determine the severity of a disease described herein. In some of such embodiments, the ratios of abundance of different biomarkers (e.g., NRE biomarkers) may be analyzed and utilized to determine disease severity and/or response to therapy.

For example, each MPS class has a number of specific NRE structures that accumulate. In some embodiments, the ratio of the different specific structures change as the disease severity changes. For example in MPS II there are a number of HS derived NREs (IdoA2S-GlcNS, IdoA2S-GlcNS6S, IdoA2S-GlcNAc, IdoA2S-GlcNAc6S) and CS/DS derived NREs (IdoA2S-GalNAc4S, IdoA2S-GalNAc6S, IdoA2S-GalNAc, IdoA2S-GalNAc4S6S) which are found in different abundance depending on the severity of disease. By monitoring the ratio of these distinct NRE structures, information about the severity of the disease and response to therapy can be obtained.

In some embodiments, a method described herein is utilized to identify disease. In specific embodiments, ratios of NRE biomarkers or Internal GAG lyase generated biomarkers are utilized in such methods. In specific instances, the ratios of abundance of different NRE and internal unsaturated saccharides generated after lyase digestion can be used to indicate the presence of human disease.

In specific embodiments, a method described herein is utilized to identify Schneckenbecken dysplasia (which leads to reduced UDP sugar donors which alters ratios of glycosminoglycan lyase generated fragments originating from HS, CS, and DS). In other exemplary embodiments, a deficiency in an enzyme required for the 2-O sulfation of heparan sulfate can be identified by examining the ratio of unsaturated 2-O sulfated disaccharides (generated by lyase digestion) to non-2-O sulfated disaccharides. In some instances, a reduction in this ratio indicates the disruption of heparan sulfate 2-O sulfation and the presence of human disease. In further exemplary embodiments, a deficiency in the biosynthesis of 4-O sulfated chondroitin and dermatan sulfate can be identified by examining the ratio of unsaturated 4-O sulfated disaccharides (generated after lyase digestion to non-4-O sulfated disaccharides). In some instances, a reduction in this ratio indicates the disruption of chondroitin sulfate 4-O sulfation and the presence of human disease. In still further exemplary embodiments, a deficiency in PAPs (3-prime-phosphoadenosine 5-prime-phosphosulfate) synthesis or transport can be identified in changes in the ratio of abundance or ratios of lyase generated glycosaminoglycan fragments.

Disorders:

In certain embodiments, a disorder associated with abnormal glycan accumulation includes a disorder associated therewith is caused by an abnormally functioning glycan degradation enzyme. In various embodiments, the abnormally functioning glycan degradation enzyme functions abnormally as a result of being present in an abnormally low amount, functioning improperly, or a combination thereof. For example, an abnormally functioning glycan degradation enzyme functions abnormally as a result of being present in an amount of less than 50%, less than 40%, less than 30%, less than 20%, less than 10%, or less than 5% than is present in an individual with normal amounts of the glycan degradation enzyme (e.g., an individual in a non-diseased, normal, or wild type state). In further or alternative embodiments, abnormally functioning glycan degradation enzymes are present in a normal amount, but do not function properly in degrading glycans. For example, such enzymes may be have amino acid substitutions in the sequences thereof that reduce or eliminate the glycan degradative properties of the enzyme.

MPS I is a human genetic disease caused by a deficiency in the lysosomal enzyme L-iduronidase. This enzyme is required in the lysosome to degrade glycans that contain iduronic acid. Due to this enzymatic deficiency, glycans with an iduronic acid on the non-reducing end accumulate to high levels (including heparan sulfate and dermatan sulfate). In certain embodiments, using the method described herein, MPS I is diagnosed in an individual from a biological sample taken therefrom. For example, in some embodiments, a biological sample is optionally placed into a defined MW cut off spin column (retains large molecules when spun), optionally washed (e.g., with water or buffer) to remove free monosaccharides, then treated with an iduronidase (e.g., to liberate a glycan residual compound iduronic acid). In certain embodiments, after incubation, the liberated iduronic acid is isolated, e.g., by washing the free monosaccharide through the defined MW cut off membrane (or other methods). In some of such embodiments, the monosaccharide would be in the flow through. The isolated monosaccharide solution is optionally dried or otherwise treated to concentrate the sample and subsequently analyzed for iduronic acid content by any suitable analytical technique (e.g., HPLC, MS, GC, or the like with or without chemical or enzymatic derivatization before detection). This method can be used to detect MPS I disease, measure disease severity, or to measure response to therapy.

MPS II is a human genetic disease caused by a deficiency in the lysosomal enzyme 2-sulfatase. This enzyme is required in the lysosome to degrade glycans that contain 2-O sulfated uronic acids. Due to this enzymatic deficiency, glycans with a 2-sulfated uronic acid on the non-reducing end accumulate to high levels (including heparan sulfate and dermatan sulfate). In certain embodiments, using the method described herein, MPS II is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 2-sulfatase (e.g., to liberate a glycan residual compound sulfate). In some embodiments, after incubation, the liberated sulfate is optionally isolated by washing the free monosaccharide (e.g., through a defined MW cut off membrane or by any other suitable method). In some of such embodiments, the free sulfate is in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS II disease, measure disease severity, or to measure response to therapy. In other exemplary embodiments, following treatment with a 2-sulfatase, the resulting 2-O desulfated non-reducing end uronic acid residues is optionally liberated with an iduronidase or glucuronidase. In some of such embodiments, the resulting liberated monosaccharide is optionally isolated, e.g., by washing free monosaccharide (e.g., through the defined MW cut off membrane or any other suitable method). In some of such embodiments, free iduronic or glucuronic acid is in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS II disease, measure disease severity, or to measure response to therapy.

MPS IIIA is a human genetic disease caused by a deficiency in the lysosomal enzyme N-sulfatase. This enzyme is required in the lysosome to degrade glycans that contain N-sulfated glucosamine residues. Due to this enzymatic deficiency, glycans with N-sulfated glucosamine residues on the non-reducing end accumulate to high levels (including heparan sulfate). In certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free sulfate, and treated with an N-sulfatase. In certain embodiments, after incubation, the liberated sulfate is optionally isolated, e.g., by washing the free monosaccharide (such as through a defined MW cut off membrane or any other suitable method). In some of such embodiments, free sulfate for detection and/or quantitation in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IIIA disease, measure disease severity, or to measure response to therapy. In further or alternative embodiments, following treatment with an N-sulfatase, the resulting N-desulfated non-reducing end glucosamine residues is optionally liberated with a hexosaminidase. In some of such embodiments, liberated monosaccharide is optionally isolated (e.g., by washing the free monosaccharide, such as through the defined MW cut off membrane or any other suitable method). In some of such embodiments, free glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free monosaccharide, and treated with an N-sulfo glucosaminidase such as a heparin lyase. In some embodiments, liberated sulfated monosaccharide is optionally isolated, e.g., by washing the free monosaccharide (such as through the defined MW cut off membrane or by any other suitable method). In some of such embodiments, free N-sulfated glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free monosaccharide, and treated with an N-sulfatase. In certain embodiments, the resulting glycan is subsequently treated such that the N-desulfated non-reducing end glucosamine residues is acetylated (e.g., with an N-acetyl transferase) and subsequently liberated with a hexosaminidase. In some of such embodiments, the resulting liberated monosaccharide is optionally isolated, e.g., by washing the free monosaccharide (e.g., through a defined MW cut off membrane or any other suitable methods). In some of such embodiments, free N-acetyl glucosamine for detection and/or quantitation is present in the flow through. In certain embodiments, the resulting isolated composition is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIIA disease, measure disease severity, or to measure response to therapy.

MPS IIIB is a human genetic disease caused by a deficiency in the enzyme N-acetyl glucosaminidase. This enzyme is required in the lysosome to degrade glycans that contain N-acetyl glucosamine residues. Due to this enzymatic deficiency, glycans with a N-acetyl glucosamine residue on the non-reducing end accumulate to high levels (including heparan sulfate). In certain embodiments, using the method described herein, MPS IIIB is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free N-acetyl glucosamine), and treated with a-acetyl glucosaminidase or a heparin lyase (e.g., to liberate a glycan residual compound N-acetyl glucosamine). In some embodiments, after incubation, the liberated N-acetyl glucosamine is optionally isolated by washing the free monosaccharide (e.g., through a defined MW cut off membrane or by any other suitable method). In some of such embodiments, the free monosaccharide is in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIB disease, measure disease severity, or to measure response to therapy.

As discussed above, in certain embodiments, using the method described herein, MPS IIIA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer) to remove free acetate, and treated with a deacetylase. The liberated acetate is optionally isolated, e.g., by washing the free acetate (such as through the defined MW cut off membrane or any other suitable method). In some of such embodiments, the free acetate for detection and/or quantitation is present the flow through. In some embodiments, the resulting isolated solution is optionally dried or otherwise treated to concentrate the sample and subsequently analyzed for acetate content by any suitable analytical technique (e.g., HPLC, MS, GC, pH detection, or the like with or without chemical or enzymatic derivatization before detection). This method can be used to detect MPS IIIB disease, measure disease severity, or to measure response to therapy.

MPS IIIC is a human genetic disease caused by a deficiency in the enzyme N-acetyltransferase. This enzyme is required in the lysosome to degrade glycans that contain glucosamine residues. Due to this enzymatic deficiency, glycans with a glucosamine residue on the non-reducing end accumulate to high levels (including heparan sulfate). In certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucosamine), and treated with a hexosaminidase or heparin lyase (e.g., to liberate a glycan residual compound glucosamine). In some embodiments, after incubation, the liberated glucosamine is optionally isolated by washing the free glucosamine (e.g., through a defined MW cut off membrane or by any other suitable method). In some of such embodiments, the free glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIC disease, measure disease severity, or to measure response to therapy.

As discussed above, in certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucosamine and/or N-acetyl glucosamine), and treated with a glucosamine N-acetyltransferase followed by a hexosaminidase (e.g., to liberate a glycan residual compound N-acetyl glucosamine). In some embodiments, after incubation, the liberated N-acetyl glucosamine is optionally isolated by washing the free N-acetyl glucosamine (e.g., through a defined MW cut off membrane or by any other suitable method). In some of such embodiments, the free N-acetyl glucosamine for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIIC disease, measure disease severity, or to measure response to therapy.

MPS IIID is a human genetic disease caused by a deficiency in the enzyme glucosamine 6-O sulfatase. This enzyme is required in the lysosome to degrade glycans that contain 6-O-sulfated glucosamine residues. Due to this enzymatic deficiency, glycans with a 6-O-sulfated N-acetyl glucosamine residue on the non-reducing end accumulate to high levels (including heparan sulfate). In certain embodiments, using the method described herein, MPS IIIC is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 6-O-sulfatase (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IIID disease, measure disease severity, or to measure response to therapy.

As discussed above, in certain embodiments, using the method described herein, MPS IIID is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate and/or N-acetyl glucosamine), and treated with a 6-O-sulfatase and a hexosaminidase (e.g., to liberate a glycan residual compound N-acetyl glucosamine). In some embodiments, after incubation, the liberated N-acetyl glucosamine is optionally isolated by washing the free N-acetyl glucosamine (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IIID disease, measure disease severity, or to measure response to therapy.

As discussed above, in certain embodiments, using the method described herein, MPS IIID is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate and/or N-acetyl glucosamine 6-O sulfate), and treated with a hexosaminidase or heparin lyase (e.g., to liberate a glycan residual compound N-acetyl glucosamine 6-O sulfate). In some embodiments, after incubation, the liberated N-acetyl glucosamine 6-O sulfate is optionally isolated by washing the free N-acetyl glucosamine 6-O sulfate (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS IIID disease, measure disease severity, or to measure response to therapy.

MPS IVA is a human genetic disease caused by a deficiency in the enzyme lysosomal enzyme galactose/N-acetyl galactosamine 6-O sulfatase. This enzyme is required in the lysosome to degrade glycans that contain 6-O-sulfated galactose and 6-O sulfated N-acetyl galactosamine residues. Due to this enzymatic deficiency, glycans with 6-O-sulfated galactose and 6-O sulfated N-acetyl galactosamine residues on the non-reducing end accumulate to high levels (including chondroitin and keratan sulfate). In certain embodiments, using the method described herein, MPS IVA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactose 6-O-sulfatase and/or an N-acetyl galactosamine 6-O sulfatase and a galactosidase and/or hexosaminidase (e.g., to liberate a glycan residual compound Gal and/or GalNAc). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IVA disease, measure disease severity, or to measure response to therapy.

As discussed above, in certain embodiments, using the method described herein, MPS IVA is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 6-O-sulfatase capable of desulfating 6-O-sulfated galactose and/or 6-O sulfated N-acetyl galactosamine residues (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS IVA disease, measure disease severity, or to measure response to therapy.

MPS IVB is a human genetic disease caused by a deficiency in the enzyme lysosomal β-galactosidase. This enzyme is required in the lysosome to degrade glycans that contain galactose residues. Due to this enzymatic deficiency, glycans with β-galactose residues on the non-reducing end accumulate to high levels (including keratan sulfate and other glycans). In certain embodiments, using the method described herein, MPS IVB is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactosidase (e.g., to liberate a glycan residual compound Gal). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS IVB disease, measure disease severity, or to measure response to therapy.

MPS VI is a human genetic disease caused by a deficiency in the enzyme 4-O sulfatase that desulfates N-acetyl galactosamine. This enzyme is required in the lysosome to degrade glycans that contain 4-O-sulfated N-acetyl galactosamine residues. Due to this enzymatic deficiency, glycans with 4-O-sulfated N-acetyl galactosamine residues on the non-reducing end accumulate to high levels (including chondroitin sulfate). In certain embodiments, using the method described herein, MPS VI is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sulfate), and treated with a 4-O-sulfatase that can desulfate 4-O-sulfated N-acetyl galactosamine residues (e.g., to liberate a glycan residual compound sulfate). In some embodiments, after incubation, the liberated sulfate is optionally isolated by washing the free sulfate (e.g., through a defined MW cut off membrane or by any other suitable method). In some of such embodiments, the free sulfate for detection and/or quantitation is present in the flow through. In certain embodiments, the resulting isolated solution is optionally dried or otherwise treated to concentrate the sample and subsequently analyzed for sulfate content by any suitable analytical technique (e.g., HPLC, MS, GC, pH detection, or the like with or without chemical or enzymatic derivatization before detection). This method can be used to detect MPS VI disease, measure disease severity, or to measure response to therapy.

As discussed above, in certain embodiments, using the method described herein, MPS VI is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free N-acetyl galactosamine), and treated with a 4-O-sulfatase that is capable of desulfating 4-O-sulfated N-acetyl galactosamine residues then treated with a hexosaminidase (e.g., to liberate a glycan residual compound N-acetyl galactosamine). In some embodiments, after incubation, the liberated N-acetyl galactosamine is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, or the like with or without chemical or enzymatic derivatization before detection). This method can be used to detect MPS VI disease, measure disease severity, or to measure response to therapy.

MPS VII is a human genetic disease caused by a deficiency in the lysosomal enzyme beta-glucuronidase. This enzyme is required in the lysosome to degrade glycans that contain glucuronic acid residues. Due to this enzymatic deficiency, glycans with glucuronic acid residues on the non-reducing end accumulate to high levels (including chondroitin sulfate, heparan sulfate and others). In certain embodiments, using the method described herein, MPS VII is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free glucuronic acid), and treated with a glucuronidase (e.g., to liberate a glycan residual compound glucuronic acid). In some embodiments, after incubation, the liberated monosaccharide is optionally isolated by washing the free monosaccharide (e.g., through a defined MW cut off membrane or by any other suitable method). In some of such embodiments, the free monosaccharide for detection and/or quantitation is present in the flow through. In certain embodiments, the resulting isolated solution is optionally dried or otherwise treated to concentrate the sample and subsequently analyzed for monosaccharide content by any suitable analytical technique (e.g., HPLC, MS, GC, pH detection, or the like with or without chemical or enzymatic derivatization before detection). This method can be used to detect MPS VII disease, measure disease severity, or to measure response to therapy.

Methods described herein can also be used to define the relative presence of different glycan classes.

Fabry Disease is a human genetic disease caused by a deficiency in the lysosomal α-galactosidase. Due to this enzymatic deficiency, glycans with non-reducing end terminal α-galactose residues are abundant. In certain embodiments, using the method described herein, Fabry Disease is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharide), and treated with a galactosidase that is capable of liberating a non-reducing end monosaccharide (e.g., to liberate a glycan residual compound). In some embodiments, after incubation, the liberated glycan residual compound is optionally isolated by washing the free glycan residual compound (e.g., through a defined MW cut off membrane or by any other suitable method). In some of such embodiments, the free glycan residual compound for detection and/or quantitation is present in the flow through. In certain embodiments, the resulting isolated solution is optionally dried or otherwise treated to concentrate the sample and subsequently analyzed for glycan residual compound content by any suitable analytical technique (e.g., HPLC, MS, GC, pH detection, or the like with or without chemical or enzymatic derivatization before detection). This method can be used to detect Fabry Disease, measure disease severity, or to measure response to therapy.

In some embodiments, as described in Table 1, other enzymes and processes are optionally utilized to diagnose other lysosomal storage diseases (LSDs). As described in the table, the appropriate enzyme(s) can be selected as appropriate for the specific disease.

Oncology—Melanoma and Neuroblastoma Via Sialic Acid

A hallmark of cancer is altered glycosylation. The changes in glycosylation are a reflection of changes in enzymes and factors that regulate the biosynthesis, turnover, presentation, stability, solubility, and degradation of glycans. Many of these changes result in glycans being produced that have altered structures. The methods described here are utilized in various embodiments to evaluate those structural changes (e.g., measure abnormal glycan accumulation) that are present on the non-reducing end of the glycans present in individuals suffering from a cancerous disease.

Some examples of cancerous diseases suitable for diagnosis and/or monitoring therapy according to methods described herein include, by way of non-limiting example, melanoma and neuroblastoma. In some instances, such cancers have alterations in the biosynthesis, turnover, presentation, stability, solubility, or degradation of gangliosides. In some instances, these sialic acid modified glycolipids are detected and/or otherwise characterized or analyzed in a biological sample (e.g., serum) of patients with these tumor types. In some embodiments, the abundance of the heterogeneous population of gangliosides is quantified to measuring sialic acid or other glycan residual released from gangliosides in the blood.

Due to this enzymatic alteration, gangliosides and other glycans are present in the body at high levels. In certain embodiments, using the method described herein, cancer (e.g., melanoma or neuroblastoma) is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free sialic acid), and treated with a sialidase that can liberate sialic acid (e.g., to liberate a glycan residual compound sialic acid). In some embodiments, after incubation, the liberated sialic acid is optionally isolated by washing the free sialic acid (e.g., through a defined MW cut off membrane or by any other suitable method). In some of such embodiments, the free sialic acid for detection and/or quantitation is present in the flow through. In certain embodiments, the resulting isolated solution is optionally dried or otherwise treated to concentrate the sample and subsequently analyzed for sialic acid content by any suitable analytical technique (e.g., HPLC, MS, GC, pH detection, or the like with or without chemical or enzymatic derivatization before detection). This method can be used to detect cancer (e.g., melanoma or neuroblastoma) disease, measure disease severity, or to measure response to therapy.

Oncology—Myeloma Via Heparan Sulfate Nonreducing Ends

An example of a human cancer that is diagnosed and/or monitored according to the methods described herein (i.e., by analyzing with such a method the altered degradation of a glycan) is multiple myeloma. In certain instances, multiple myeloma commonly produces heparanase. Heparanase is an endoglycosidase that cleaved heparan sulfate into smaller fragments, exposing novel non-reducing end structures. In certain embodiments described herein, the presence of these novel non-reducing end structures are detected using any method described herein (e.g., by incubating a biological sample with various glycosidases or sulfatases to detect the presence of novel glycan non-reducing ends).

Due to this enzymatic alteration, glycans (including heparan sulfate and others) are present in the body at high levels. In certain embodiments, using the method described herein, cancer (e.g., multiple myeloma) is diagnosed in an individual from a biological sample taken therefrom. For example, in some embodiments, a biological sample is optionally placed in to a defined MW cut off spin column (retains large molecules when spun), optionally washed (e.g., with 1 or more volumes of water or buffer to remove free monosaccharides and/or sulfate), and treated with a sulfatase, iduronidase, glucuronidase, hexosaminidase, or lyase that is capable of liberating a non-reducing end monosaccharide or sulfate. In some embodiments, after incubation, the liberated glycan residual compound is optionally isolated by washing the free glycan residual compound (e.g., through a defined MW cut off membrane or by any other suitable method). In some of such embodiments, the free glycan residual compound for detection and/or quantitation is present in the flow through. In certain embodiments, the resulting isolated solution is optionally dried or otherwise treated to concentrate the sample and subsequently analyzed for glycan residual compound content by any suitable analytical technique (e.g., HPLC, MS, GC, pH detection, or the like with or without chemical or enzymatic derivatization before detection). This method can be used to detect cancer (e.g., multiple myeloma) disease, measure disease severity, or to measure response to therapy.

Oncology—Adenocarcinoma

Adenocarcinoma is associated with changes in glycosylation including increased sialylation and fucosylation. The described method can be used to measure disease by analyzing glycans (total or purified or enriched for specific glycan classes) from a patient for the amount of nonreducing end terminal sialic acid or fucose, by measuring the release of these glycan residuals after treatment with a sialidase or fucosidase.

Other Applications

As described in Tables 12-15, various diseases associated with changes in glycosylation are optionally diagnosed and/or monitored according to methods described herein. Various disorders include, by way of non-limiting example, lysosomal storage disease, cancer, neurological disease (dementia, Alzheimer's, etc), liver disease, bone disease, infectious diseases, and the like.

Provided herein are methods of diagnosing individuals (including, e.g., a disease state or the severity of a disease states) with a lysosomal storage disease (LSD) or methods of monitoring the treatment of a lysosomal storage disease (LSD). Provided in Table 10 are specific embodiments of disease that are optionally diagnosed and/or monitored according to various embodiments described herein. Table 12 also illustrates various non-limiting embodiments of specific enzyme(s) that are optionally utilized to treat a biological sample from an individual suffering from or suspected (e.g., through a pre- or preliminary screening process) of suffering from an LSD. Moreover, Table 12 further illustrates various glycan residual compounds that are liberated in various embodiments described herein, such liberated glycan residual compounds optionally being detected and/or measured in order to diagnose and/or monitor a lysosomal storage disease (LSD).

TABLE 12

Exemplary LSD Uses

| Disease | Non-Reducing End Structure | Primary Releasing Enzyme | Secondary Releasing Enzyme | Glycan Residual Compound |
|---|---|---|---|---|
| MPS I | IdoA | iduronidase | | IdoA |
| MPS II | IdoA-2-O sufate and GlcA-2-O sufate | 2-sulfatase | | Sulfate |
| MPS II | IdoA-2-O sufate and GlcA-2-O sufate | 2-sulfatase | Iduronidase and/or glucuronidase | IdoA and/or GlcA |
| MPS IIIA | GlcN—N-sulfate | N-sulfatase | | Sulfate |
| MPS IIIA | GlcN—N-sulfate | N-sulfatase | hexosaminidase | GlcN |
| MPS IIIA | GlcN—N-sulfate | N-sulfatase | Heparin lyase | GlcN |
| MPS IIIA | GlcN—N-sulfate | N-sulfatase | N-acetyl transferase and hexosaminidase | GlcNAc |
| MPS IIIA | GlcN—N-sulfate | Heparin lyase | | GlcN—N-sulfate |
| MPS IIIB | GlcNAc | hexosaminidase | | GlcNAc |
| MPS IIIB | GlcNAc | Deacetylase | | acetate |
| MPS IIIB | GlcNAc | Heparin lyase | | GlcNAc |
| MPS IIIC | GlcNAc-6-O sulfate | 6-O sulfatase | | Sulfate |
| MPS IIIC | GlcNAc-6-O sulfate | 6-O sulfatase | hexosaminidase | GlcNAc |
| MPS IIIC | GlcNAc-6-O sulfate | 6-O sulfatase | Heparin lyase | GlcNAc |
| MPS IIIC | GlcNAc-6-O sulfate | Heparin lyase | | GlcNAc-6-O sulfate |
| MPS IIID | GlcN | hexosaminidase | | GlcN |
| MPS IIID | GlcN | Heparin lyase | | GlcN |
| MPS IIID | GlcN | N-acetyl transferase | hexosaminidase | GlcNAc |
| MPS IVA | Gal-6-O sulfate and GalNAc-6-O sulfate | 6-O sulfatase | | Sulfate |
| MPS IVA | Gal-6-O sulfate and GalNAc-6-O sulfate | galactosidase | | Gal-6-O sulfate |
| MPS IVA | Gal-6-O sulfate and GalNAc-6-O sulfate | N-acetyl galactosidase | | GalNAc-6-O sulfate |

TABLE 12-continued

Exemplary LSD Uses

| Disease | Non-Reducing End Structure | Primary Releasing Enzyme | Secondary Releasing Enzyme | Glycan Residual Compound |
|---|---|---|---|---|
| MPS IVA | Gal-6-O sulfate and GalNAc-6-O sulfate | hexosaminidase | | GalNAc-6-O sulfate |
| MPS IVA | Gal-6-O sulfate and GalNAc-6-O sulfate | 6-O sulfatase | galactosidase | Gal |
| MPS IVA | Gal-6-O sulfate and GalNAc-6-O sulfate | 6-O sulfatase | N-acetyl galactosidase | GalNAc |
| MPS IVA | Gal-6-O sulfate and GalNAc-6-O sulfate (+/−4-O-sulfate | Any combination of Chondroitin lyase A and/or B and/or C activities) | | GalNAc-6-O sulfate (+/−4-O sulfate) |
| MPS IVA | Gal-6-O sulfate and GalNAc-6-O sulfate (+/−4-O-sulfate | 6-O sulfatase | Any combination of Chondroitin lyase A and/or B and/or C activities) | GalNAc (+−4-O sulfate) |
| MPS IVB | Gal | Galactosidase | | Gal |
| MPS VI | GalNAc-4-O sulfate | 4-O sulfatase | | Sulfate |
| MPS VI | GalNAc-4-O sulfate | 4-O sulfatase | hexosaminidase | GalNAc |
| MPS VI | GalNAc-4-O sulfate | 4-O sulfatase | Chondroitin lyase | GalNAc |
| MPS VI | GalNAc-4-O sulfate | Chondroitin lyase | | GalNAc-4-O sulfate |
| MPS VII | GlcA | β-glucuronidase | | GlcA |
| Alpha Mannosidosis | Mannose | Manosidase | | Man |
| Aspartylglucosaminuria | GlcNAc | hexosaminidase | | GlcNAc |
| Fabry | Galactose | galactosidase | | Gal |
| Fucosidosis | Fucose | fucosidase | | Fuc |
| Galactosialidosis | Galactose and/or Sialic acid | Galactosidase and/or sialidase | | Gal and/or Sialic acid |
| Gaucher | glucose | glucosidase | | glucose |
| GM1 gangliosidosis | Beta-Galactose | Beta-Galactosidase | | galactose |
| GM1 gangliosidosis | Beta-Galactose | Beta-Galactosidase | Hexosaminidase | GalNAc |
| GM2 activator deficiency | GalNAc | hexosaminidase | | GalNAc |
| Sialidosis | Sialic acid | Sialidase | | Sialic acid |
| Sialidosis | Sialic acid | Alpha 2,3 Sialidase | | Sialic acid |
| Sialidosis | Sialic acid | Alphas 2,6 Sialidase | | Sialic acid |
| Sialidosis | Sialic acid | Alphas 2,8 Sialidase | | Sialic acid |
| Krabbe | Galactose | galactosidase | | Galactose |
| Metachromatic Leukodystrophy | Sulfated galactosylceramide | 3-O sulfatase | | Sulfate |
| Metachromatic Leukodystrophy | Sulfated galactosylceramide | 3-O sulfatase | galactosidase | Galactose |
| Mucolipidosis II | Broad range of glycans | Any listed enzyme | | Any monosaccharide or sulfate |
| Mucolipidosis III | Broad range of glycans | Any listed enzyme | | Any monosaccharide or sulfate |
| Mucolipidosis IV | Broad range of glycans | Any listed enzyme | | Any monosaccharide or sulfate |
| Multiple Sulfatase Deficiency | Sulfated glycans | sulfatase | | sulfate |
| Multiple Sulfatase Deficiency | Sulfated glycans | sulfatase | Any glycosidase | monosaccharide |
| Multiple Sulfatase Deficiency | Sulfated glycans | Any glycosidase | | Sulfated monosaccharide |
| Glycogen Storage Disease (Pompe) | glucose | glucosidase | | glucose |
| Sandhoff | GalNAc | hexosaminidase | | GalNAc |

TABLE 12-continued

Exemplary LSD Uses

| Disease | Non-Reducing End Structure | Primary Releasing Enzyme | Secondary Releasing Enzyme | Glycan Residual Compound |
|---|---|---|---|---|
| Tay-Sachs | GalNAc | hexosaminidase | | GalNAc |
| AB Variant | GalNAc | hexosaminidase | | GalNAc |
| Schindler Disease | Alpha-GalNAc | hexosaminidase | | GalNAc |
| Salla Disease | Sialic acid | none | | Sialic Acid |
| Alpha Mannosidosis | Alpha mannose | mannosidase | | Mannose |
| Beta Mannosidosis | Beta mannose | mannosidase | | Mannose |
| Globoid cell leukodystrophy | galactose | galactosidase | | galactose |

Provided herein are methods of diagnosing individuals (including, e.g., a disease state or the severity of a disease states) with a cancerous disease state or methods of monitoring the treatment of a cancer. Provided in Table 13 are specific embodiments of disease that are optionally diagnosed and/or monitored according to various embodiments described herein. Table 13 also illustrates various non-limiting embodiments of specific enzyme(s) that are optionally utilized to treat a biological sample from an individual suffering from or suspected of (e.g., through a pre- or preliminary screening process) suffering from a cancerous disease state. Moreover, Table 13 further illustrates various glycan residual compounds that are liberated in various embodiments described herein, such liberated glycan residual compounds optionally being detected and/or measured in order to diagnose and/or monitor a cancerous disease state.

TABLE 13

Exemplary Oncology Uses

| Cancer Type | Non-Reducing End Structure | Primary Liberating Enzyme | Secondary Liberating Enzyme | Glycan Residual Compound |
|---|---|---|---|---|
| Melanoma | Sialic Acid | Sialidase | | Sialic acid |
| Melanoma | Sialic Acid | Alpha 2,8 Sialidase | | Sialic acid |
| Melanoma | Sialic Acid | Alpha 2,3 Sialidase | | Sialic acid |
| Melanoma | Sialic Acid | Alpha 2,6 Sialidase | | Sialic acid |
| Melanoma | GalNAc | Hexosaminidase | | GalNAc |
| Melanoma | GalNAc | Sialidase | Hexosaminidase | GalNAc |
| Melanoma | Sialic acid | Hexosaminidase | Sialidase | Sialic acid |
| Melanoma | Galactose | galactosidase | | Galactose |
| Melanoma | Galactose | sialidase | galactosidase | Galactose |
| Melanoma | Fucose | fucosidase | | Fucose |
| Melanoma | Galactose | Galactosidase | | Galactose |
| Melanoma | GlcNAc | hexosaminidase | | GlcNAc |
| Melanoma | Sulfate | Sulfatase | | Sulfate |
| Melanoma | Sulfated hexose | Sulfatase | hexosaminidase | GlcNAc or GalNAc |
| Melanoma | Sulfated uronic acid | Sulfatase | Iduronidase or glucouronidase | IdoA or GlcA |
| Neuroblastoma | Sialic Acid | Sialidase | | Sialic acid |
| Neuroblastoma | Sialic Acid | Alpha 2,8 Sialidase | | Sialic acid |
| Neuroblastoma | Sialic Acid | Alpha 2,3 Sialidase | | Sialic acid |
| Neuroblastoma | Sialic Acid | Alpha 2,6 Sialidase | | Sialic acid |
| Neuroblastoma | GalNAc | Hexosaminidase | | GalNAc |
| Neuroblastoma | GalNAc | Sialidase | Hexosaminidase | GalNAc |
| Neuroblastoma | Sialic acid | Hexosaminidase | Sialidase | Sialic acid |
| Neuroblastoma | Galactose | galactosidase | | Galactose |
| Neuroblastoma | Galactose | sialidase | galactosidase | Galactose |
| Neuroblastoma | Fucose | fucosidase | | Fucose |
| Neuroblastoma | Galactose | Galactosidase | | Galactose |
| Neuroblastoma | GlcNAc | hexosaminidase | | GlcNAc |
| Neuroblastoma | Sulfate | Sulfatase | | Sulfate |
| Neuroblastoma | Sulfated hexose | Sulfatase | hexosaminidase | GlcNAc or GalNAc |
| Neuroblastoma | Sulfated uronic acid | Sulfatase | Iduronidase or glucouronidase | IdoA or GlcA |
| Adenocarcinoma | Sialic Acid | Sialidase | | Sialic acid |
| Adenocarcinoma | Sialic Acid | Alpha 2,8 Sialidase | | Sialic acid |
| Adenocarcinoma | Sialic Acid | Alpha 2,3 Sialidase | | Sialic acid |
| Adenocarcinoma | Sialic Acid | Alpha 2,6 Sialidase | | Sialic acid |
| Adenocarcinoma | GalNAc | Hexosaminidase | | GalNAc |
| Adenocarcinoma | GalNAc | Sialidase | Hexosaminidase | GalNAc |
| Adenocarcinoma | Sialic acid | Hexosaminidase | Sialidase | Sialic acid |

TABLE 13-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Adenocarcinoma | Galactose | galactosidase | | Galactose |
| Adenocarcinoma | Galactose | sialidase | galactosidase | Galactose |
| Adenocarcinoma | Fucose | fucosidase | | Fucose |
| Adenocarcinoma | Galactose | Galactosidase | | Galactose |
| Adenocarcinoma | GlcNAc | hexosaminidase | | GlcNAc |
| Adenocarcinoma | Sulfate | Sulfatase | | Sulfate |
| Adenocarcinoma | Sulfated hexose | Sulfatase | hexosaminidase | GlcNAc or GalNAc |
| Adenocarcinoma | Sulfated uronic acid | Sulfatase | Iduronidase or glucouronidase | IdoA or GlcA |
| Myeloma | Sialic Acid | Sialidase | | Sialic acid |
| Myeloma | Sialic Acid | Alpha 2,8 Sialidase | | Sialic acid |
| Myeloma | Sialic Acid | Alpha 2,3 Sialidase | | Sialic acid |
| Myeloma | Sialic Acid | Alpha 2,6 Sialidase | | Sialic acid |
| Myeloma | GalNAc | Hexosaminidase | | GalNAc |
| Myeloma | GalNAc | Sialidase | Hexosaminidase | GalNAc |
| Myeloma | Sialic acid | Hexosaminidase | Sialidase | Sialic acid |
| Myeloma | Galactose | galactosidase | | Galactose |
| Myeloma | Galactose | sialidase | galactosidase | Galactose |
| Myeloma | Fucose | fucosidase | | Fucose |
| Myeloma | Galactose | Galactosidase | | Galactose |
| Myeloma | GlcNAc | hexosaminidase | | GlcNAc |
| Myeloma | Sulfate | Sulfatase | | Sulfate |
| Myeloma | Sulfated hexose | Sulfatase | hexosaminidase | GlcNAc or GalNAc |
| Myeloma | Sulfated uronic acid | Sulfatase | Iduronidase or glucouronidase | IdoA or GlcA |
| Breast | Sialic Acid | Sialidase | | Sialic acid |
| Breast | Sialic Acid | Alpha 2,8 Sialidase | | Sialic acid |
| Breast | Sialic Acid | Alpha 2,3 Sialidase | | Sialic acid |
| Breast | Sialic Acid | Alpha 2,6 Sialidase | | Sialic acid |
| Breast | GalNAc | Hexosaminidase | | GalNAc |
| Breast | GalNAc | Sialidase | Hexosaminidase | GalNAc |
| Breast | Sialic acid | Hexosaminidase | Sialidase | Sialic acid |
| Breast | Galactose | galactosidase | | Galactose |
| Breast | Galactose | sialidase | galactosidase | Galactose |
| Breast | Fucose | fucosidase | | Fucose |
| Breast | Galactose | Galactosidase | | Galactose |
| Breast | GlcNAc | hexosaminidase | | GlcNAc |
| Breast | Sulfate | Sulfatase | | Sulfate |
| Breast | Sulfated hexose | Sulfatase | hexosaminidase | GlcNAc or GalNAc |
| Breast | Sulfated uronic acid | Sulfatase | Iduronidase or glucouronidase | IdoA or GlcA |
| Ovarian | Sialic Acid | Sialidase | | Sialic acid |
| Ovarian | Sialic Acid | Alpha 2,8 Sialidase | | Sialic acid |
| Ovarian | Sialic Acid | Alpha 2,3 Sialidase | | Sialic acid |
| Ovarian | Sialic Acid | Alpha 2,6 Sialidase | | Sialic acid |
| Ovarian | GalNAc | Hexosaminidase | | GalNAc |
| Ovarian | GalNAc | Sialidase | Hexosaminidase | GalNAc |
| Ovarian | Sialic acid | Hexosaminidase | Sialidase | Sialic acid |
| Ovarian | Galactose | galactosidase | | Galactose |
| Ovarian | Galactose | sialidase | galactosidase | Galactose |
| Ovarian | Fucose | fucosidase | | Fucose |
| Ovarian | Galactose | Galactosidase | | Galactose |
| Ovarian | GlcNAc | hexosaminidase | | GlcNAc |
| Ovarian | Sulfate | Sulfatase | | Sulfate |
| Ovarian | Sulfated hexose | Sulfatase | hexosaminidase | GlcNAc or GalNAc |
| Ovarian | Sulfated uronic acid | Sulfatase | Iduronidase or glucouronidase | IdoA or GlcA |
| Stomach | Sialic Acid | Sialidase | | Sialic acid |
| Stomach | Sialic Acid | Alpha 2,8 Sialidase | | Sialic acid |
| Stomach | Sialic Acid | Alpha 2,3 Sialidase | | Sialic acid |
| Stomach | Sialic Acid | Alpha 2,6 Sialidase | | Sialic acid |
| Stomach | GalNAc | Hexosaminidase | | GalNAc |
| Stomach | GalNAc | Sialidase | Hexosaminidase | GalNAc |
| Stomach | Sialic acid | Hexosaminidase | Sialidase | Sialic acid |
| Stomach | Galactose | galactosidase | | Galactose |
| Stomach | Galactose | sialidase | galactosidase | Galactose |

TABLE 13-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Stomach | Fucose | fucosidase | | Fucose |
| Stomach | Galactose | Galactosidase | | Galactose |
| Stomach | GlcNAc | hexosaminidase | | GlcNAc |
| Stomach | Sulfate | Sulfatase | | Sulfate |
| Stomach | Sulfated hexose | Sulfatase | hexosaminidase | GlcNAc or GalNAc |
| Stomach | Sulfated uronic acid | Sulfatase | Iduronidase or glucouronidase | IdoA or GlcA |
| Lung | Sialic Acid | Sialidase | | Sialic acid |
| Lung | Sialic Acid | Alpha 2,8 Sialidase | | Sialic acid |
| Lung | Sialic Acid | Alpha 2,3 Sialidase | | Sialic acid |
| Lung | Sialic Acid | Alpha 2,6 Sialidase | | Sialic acid |
| Lung | GalNAc | Hexosaminidase | | GalNAc |
| Lung | GalNAc | Sialidase | Hexosaminidase | GalNAc |
| Lung | Sialic acid | Hexosaminidase | Sialidase | Sialic acid |
| Lung | Galactose | galactosidase | | Galactose |
| Lung | Galactose | sialidase | galactosidase | Galactose |
| Lung | Fucose | fucosidase | | Fucose |
| Lung | Galactose | Galactosidase | | Galactose |
| Lung | GlcNAc | hexosaminidase | | GlcNAc |
| Lung | Sulfate | Sulfatase | | Sulfate |
| Lung | Sulfated hexose | Sulfatase | hexosaminidase | GlcNAc or GalNAc |
| Lung | Sulfated uronic acid | Sulfatase | Iduronidase or glucouronidase | IdoA or GlcA |
| Pancreatic | Sialic Acid | Sialidase | | Sialic acid |
| Pancreatic | Sialic Acid | Alpha 2,8 Sialidase | | Sialic acid |
| Pancreatic | Sialic Acid | Alpha 2,3 Sialidase | | Sialic acid |
| Pancreatic | Sialic Acid | Alpha 2,6 Sialidase | | Sialic acid |
| Pancreatic | GalNAc | Hexosaminidase | | GalNAc |
| Pancreatic | GalNAc | Sialidase | Hexosaminidase | GalNAc |
| Pancreatic | Sialic acid | Hexosaminidase | Sialidase | Sialic acid |
| Pancreatic | Galactose | galactosidase | | Galactose |
| Pancreatic | Galactose | sialidase | galactosidase | Galactose |
| Pancreatic | Fucose | fucosidase | | Fucose |
| Pancreatic | Galactose | Galactosidase | | Galactose |
| Pancreatic | GlcNAc | hexosaminidase | | GlcNAc |
| Pancreatic | Sulfate | Sulfatase | | Sulfate |
| Pancreatic | Sulfated hexose | Sulfatase | hexosaminidase | GlcNAc or GalNAc |
| Pancreatic | Sulfated uronic acid | Sulfatase | Iduronidase or glucouronidase | IdoA or GlcA |
| Oral | Sialic Acid | Sialidase | | Sialic acid |
| Oral | Sialic Acid | Alpha 2,8 Sialidase | | Sialic acid |
| Oral | Sialic Acid | Alpha 2,3 Sialidase | | Sialic acid |
| Oral | Sialic Acid | Alpha 2,6 Sialidase | | Sialic acid |
| Oral | GalNAc | Hexosaminidase | | GalNAc |
| Oral | GalNAc | Sialidase | Hexosaminidase | GalNAc |
| Oral | Sialic acid | Hexosaminidase | Sialidase | Sialic acid |
| Oral | Galactose | galactosidase | | Galactose |
| Oral | Galactose | sialidase | galactosidase | Galactose |
| Oral | Fucose | fucosidase | | Fucose |
| Oral | Galactose | Galactosidase | | Galactose |
| Oral | GlcNAc | hexosaminidase | | GlcNAc |
| Oral | Sulfate | Sulfatase | | Sulfate |
| Oral | Sulfated hexose | Sulfatase | hexosaminidase | GlcNAc or GalNAc |
| Oral | Sulfated uronic acid | Sulfatase | Iduronidase or glucouronidase | IdoA or GlcA |
| Colorectal | Sialic Acid | Sialidase | | Sialic acid |
| Colorectal | Sialic Acid | Alpha 2,8 Sialidase | | Sialic acid |
| Colorectal | Sialic Acid | Alpha 2,3 Sialidase | | Sialic acid |
| Colorectal | Sialic Acid | Alpha 2,6 Sialidase | | Sialic acid |
| Colorectal | GalNAc | Hexosaminidase | | GalNAc |
| Colorectal | GalNAc | Sialidase | Hexosaminidase | GalNAc |
| Colorectal | Sialic acid | Hexosaminidase | Sialidase | Sialic acid |
| Colorectal | Galactose | galactosidase | | Galactose |
| Colorectal | Galactose | sialidase | galactosidase | Galactose |
| Colorectal | Fucose | fucosidase | | Fucose |
| Colorectal | Galactose | Galactosidase | | Galactose |

TABLE 13-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Colorectal | GlcNAc | hexosaminidase | | GlcNAc |
| Colorectal | Sulfate | Sulfatase | | Sulfate |
| Colorectal | Sulfated hexose | Sulfatase | hexosaminidase | GlcNAc or GalNAc |
| Colorectal | Sulfated uronic acid | Sulfatase | Iduronidase or glucouronidase | IdoA or GlcA |
| Kidney | Sialic Acid | Sialidase | | Sialic acid |
| Kidney | Sialic Acid | Alpha 2,8 Sialidase | | Sialic acid |
| Kidney | Sialic Acid | Alpha 2,3 Sialidase | | Sialic acid |
| Kidney | Sialic Acid | Alpha 2,6 Sialidase | | Sialic acid |
| Kidney | GalNAc | Hexosaminidase | | GalNAc |
| Kidney | GalNAc | Sialidase | Hexosaminidase | GalNAc |
| Kidney | Sialic acid | Hexosaminidase | Sialidase | Sialic acid |
| Kidney | Galactose | galactosidase | | Galactose |
| Kidney | Galactose | sialidase | galactosidase | Galactose |
| Kidney | Fucose | fucosidase | | Fucose |
| Kidney | Galactose | Galactosidase | | Galactose |
| Kidney | GlcNAc | hexosaminidase | | GlcNAc |
| Kidney | Sulfate | Sulfatase | | Sulfate |
| Kidney | Sulfated hexose | Sulfatase | hexosaminidase | GlcNAc or GalNAc |
| Kidney | Sulfated uronic acid | Sulfatase | Iduronidase or glucouronidase | IdoA or GlcA |
| Bladder | Sialic Acid | Sialidase | | Sialic acid |
| Bladder | Sialic Acid | Alpha 2,8 Sialidase | | Sialic acid |
| Bladder | Sialic Acid | Alpha 2,3 Sialidase | | Sialic acid |
| Bladder | Sialic Acid | Alpha 2,6 Sialidase | | Sialic acid |
| Bladder | GalNAc | Hexosaminidase | | GalNAc |
| Bladder | GalNAc | Sialidase | Hexosaminidase | GalNAc |
| Bladder | Sialic acid | Hexosaminidase | Sialidase | Sialic acid |
| Bladder | Galactose | galactosidase | | Galactose |
| Bladder | Galactose | sialidase | galactosidase | Galactose |
| Bladder | Fucose | fucosidase | | Fucose |
| Bladder | Galactose | Galactosidase | | Galactose |
| Bladder | GlcNAc | hexosaminidase | | GlcNAc |
| Bladder | Sulfate | Sulfatase | | Sulfate |
| Bladder | Sulfated hexose | Sulfatase | hexosaminidase | GlcNAc or GalNAc |
| Bladder | Sulfated uronic acid | Sulfatase | Iduronidase or glucouronidase | IdoA or GlcA |
| Prostate | Sialic Acid | Sialidase | | Sialic acid |
| Prostate | Sialic Acid | Alpha 2,8 Sialidase | | Sialic acid |
| Prostate | Sialic Acid | Alpha 2,3 Sialidase | | Sialic acid |
| Prostate | Sialic Acid | Alpha 2,6 Sialidase | | Sialic acid |
| Prostate | GalNAc | Hexosaminidase | | GalNAc |
| Prostate | GalNAc | Sialidase | Hexosaminidase | GalNAc |
| Prostate | Sialic acid | Hexosaminidase | Sialidase | Sialic acid |
| Prostate | Galactose | galactosidase | | Galactose |
| Prostate | Galactose | sialidase | galactosidase | Galactose |
| Prostate | Fucose | fucosidase | | Fucose |
| Prostate | Galactose | Galactosidase | | Galactose |
| Prostate | GlcNAc | hexosaminidase | | GlcNAc |
| Prostate | Sulfate | Sulfatase | | Sulfate |
| Prostate | Sulfated hexose | Sulfatase | hexosaminidase | GlcNAc or GalNAc |
| Prostate | Sulfated uronic acid | Sulfatase | Iduronidase or glucouronidase | IdoA or GlcA |
| Uterine | Sialic Acid | Sialidase | | Sialic acid |
| Uterine | Sialic Acid | Alpha 2,8 Sialidase | | Sialic acid |
| Uterine | Sialic Acid | Alpha 2,3 Sialidase | | Sialic acid |
| Uterine | Sialic Acid | Alpha 2,6 Sialidase | | Sialic acid |
| Uterine | GalNAc | Hexosaminidase | | GalNAc |
| Uterine | GalNAc | Sialidase | Hexosaminidase | GalNAc |
| Uterine | Sialic acid | Hexosaminidase | Sialidase | Sialic acid |
| Uterine | Galactose | galactosidase | | Galactose |
| Uterine | Galactose | sialidase | galactosidase | Galactose |
| Uterine | Fucose | fucosidase | | Fucose |
| Uterine | Galactose | Galactosidase | | Galactose |
| Uterine | GlcNAc | hexosaminidase | | GlcNAc |
| Uterine | Sulfate | Sulfatase | | Sulfate |

TABLE 13-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Uterine | Sulfated hexose | Sulfatase | hexosaminidase | GlcNAc or GalNAc |
| Uterine | Sulfated uronic acid | Sulfatase | Iduronidase or glucouronidase | IdoA or GlcA |
| Thyroid | Sialic Acid | Sialidase | | Sialic acid |
| Thyroid | Sialic Acid | Alpha 2,8 Sialidase | | Sialic acid |
| Thyroid | Sialic Acid | Alpha 2,3 Sialidase | | Sialic acid |
| Thyroid | Sialic Acid | Alpha 2,6 Sialidase | | Sialic acid |
| Thyroid | GalNAc | Hexosaminidase | | GalNAc |
| Thyroid | GalNAc | Sialidase | Hexosaminidase | GalNAc |
| Thyroid | Sialic acid | Hexosaminidase | Sialidase | Sialic acid |
| Thyroid | Galactose | galactosidase | | Galactose |
| Thyroid | Galactose | sialidase | galactosidase | Galactose |
| Thyroid | Fucose | fucosidase | | Fucose |
| Thyroid | Galactose | Galactosidase | | Galactose |
| Thyroid | GlcNAc | hexosaminidase | | GlcNAc |
| Thyroid | Sulfate | Sulfatase | | Sulfate |
| Thyroid | Sulfated hexose | Sulfatase | hexosaminidase | GlcNAc or GalNAc |
| Thyroid | Sulfated uronic acid | Sulfatase | Iduronidase or glucouronidase | IdoA or GlcA |
| Liver | Sialic Acid | Sialidase | | Sialic acid |
| Liver | Sialic Acid | Alpha 2,8 Sialidase | | Sialic acid |
| Liver | Sialic Acid | Alpha 2,3 Sialidase | | Sialic acid |
| Liver | Sialic Acid | Alpha 2,6 Sialidase | | Sialic acid |
| Liver | GalNAc | Hexosaminidase | | GalNAc |
| Liver | GalNAc | Sialidase | Hexosaminidase | GalNAc |
| Liver | Sialic acid | Hexosaminidase | Sialidase | Sialic acid |
| Liver | Galactose | galactosidase | | Galactose |
| Liver | Galactose | sialidase | galactosidase | Galactose |
| Liver | Fucose | fucosidase | | Fucose |
| Liver | Galactose | Galactosidase | | Galactose |
| Liver | GlcNAc | hexosaminidase | | GlcNAc |
| Liver | Sulfate | Sulfatase | | Sulfate |
| Liver | Sulfated hexose | Sulfatase | hexosaminidase | GlcNAc or GalNAc |
| Liver | Sulfated uronic acid | Sulfatase | Iduronidase or glucouronidase | IdoA or GlcA |
| Esophagus | Sialic Acid | Sialidase | | Sialic acid |
| Esophagus | Sialic Acid | Alpha 2,8 Sialidase | | Sialic acid |
| Esophagus | Sialic Acid | Alpha 2,3 Sialidase | | Sialic acid |
| Esophagus | Sialic Acid | Alpha 2,6 Sialidase | | Sialic acid |
| Esophagus | GalNAc | Hexosaminidase | | GalNAc |
| Esophagus | GalNAc | Sialidase | Hexosaminidase | GalNAc |
| Esophagus | Sialic acid | Hexosaminidase | Sialidase | Sialic acid |
| Esophagus | Galactose | galactosidase | | Galactose |
| Esophagus | Galactose | sialidase | galactosidase | Galactose |
| Esophagus | Fucose | fucosidase | | Fucose |
| Esophagus | Galactose | Galactosidase | | Galactose |
| Esophagus | GlcNAc | hexosaminidase | | GlcNAc |
| Esophagus | Sulfate | Sulfatase | | Sulfate |
| Esophagus | Sulfated hexose | Sulfatase | hexosaminidase | GlcNAc or GalNAc |
| Esophagus | Sulfated uronic acid | Sulfatase | Iduronidase or glucouronidase | IdoA or GlcA |
| Brain | Sialic Acid | Sialidase | | Sialic acid |
| Brain | Sialic Acid | Alpha 2,8 Sialidase | | Sialic acid |
| Brain | Sialic Acid | Alpha 2,3 Sialidase | | Sialic acid |
| Brain | Sialic Acid | Alpha 2,6 Sialidase | | Sialic acid |
| Brain | GalNAc | Hexosaminidase | | GalNAc |
| Brain | GalNAc | Sialidase | Hexosaminidase | GalNAc |
| Brain | Sialic acid | Hexosaminidase | Sialidase | Sialic acid |
| Brain | Galactose | galactosidase | | Galactose |
| Brain | Galactose | sialidase | galactosidase | Galactose |
| Brain | Fucose | fucosidase | | Fucose |
| Brain | Galactose | Galactosidase | | Galactose |
| Brain | GlcNAc | hexosaminidase | | GlcNAc |
| Brain | Sulfate | Sulfatase | | Sulfate |

TABLE 13-continued

Exemplary Oncology Uses

| Cancer Type | Non-Reducing End Structure | Primary Liberating Enzyme | Secondary Liberating Enzyme | Glycan Residual Compound |
|---|---|---|---|---|
| Brain | Sulfated hexose | Sulfatase | hexosaminidase | GlcNAc or GalNAc |
| Brain | Sulfated uronic acid | Sulfatase | Iduronidase or glucouronidase | IdoA or GlcA |
| Lymphomas | Sialic Acid | Sialidase | | Sialic acid |
| Lymphomas | Sialic Acid | Alpha 2,8 Sialidase | | Sialic acid |
| Lymphomas | Sialic Acid | Alpha 2,3 Sialidase | | Sialic acid |
| Lymphomas | Sialic Acid | Alpha 2,6 Sialidase | | Sialic acid |
| Lymphomas | GalNAc | Hexosaminidase | | GalNAc |
| Lymphomas | GalNAc | Sialidase | Hexosaminidase | GalNAc |
| Lymphomas | Sialic acid | Hexosaminidase | Sialidase | Sialic acid |
| Lymphomas | Galactose | galactosidase | | Galactose |
| Lymphomas | Galactose | sialidase | galactosidase | Galactose |
| Lymphomas | Fucose | fucosidase | | Fucose |
| Lymphomas | Galactose | Galactosidase | | Galactose |
| Lymphomas | GlcNAc | hexosaminidase | | GlcNAc |
| Lymphomas | Sulfate | Sulfatase | | Sulfate |
| Lymphomas | Sulfated hexose | Sulfatase | hexosaminidase | GlcNAc or GalNAc |
| Lymphomas | Sulfated uronic acid | Sulfatase | Iduronidase or glucouronidase | IdoA or GlcA |
| Leukemias | Sialic Acid | Sialidase | | Sialic acid |
| Leukemias | Sialic Acid | Alpha 2,8 Sialidase | | Sialic acid |
| Leukemias | Sialic Acid | Alpha 2,3 Sialidase | | Sialic acid |
| Leukemias | Sialic Acid | Alpha 2,6 Sialidase | | Sialic acid |
| Leukemias | GalNAc | Hexosaminidase | | GalNAc |
| Leukemias | GalNAc | Sialidase | Hexosaminidase | GalNAc |
| Leukemias | Sialic acid | Hexosaminidase | Sialidase | Sialic acid |
| Leukemias | Galactose | galactosidase | | Galactose |
| Leukemias | Galactose | sialidase | galactosidase | Galactose |
| Leukemias | Fucose | fucosidase | | Fucose |
| Leukemias | Galactose | Galactosidase | | Galactose |
| Leukemias | GlcNAc | hexosaminidase | | GlcNAc |
| Leukemias | Sulfate | Sulfatase | | Sulfate |
| Leukemias | Sulfated hexose | Sulfatase | hexosaminidase | GlcNAc or GalNAc |
| Leukemias | Sulfated uronic acid | Sulfatase | Iduronidase or glucouronidase | IdoA or GlcA |

Provided herein are methods of diagnosing individuals (including, e.g., a disease state or the severity of a disease states) with a disease state associated with abnormal glycan accumulation. Provided in Table 14 are specific embodiments of disease that are optionally diagnosed and/or monitored according to various embodiments described herein. Table 14 also illustrates various non-limiting embodiments of specific enzyme(s) that are optionally utilized to treat a biological sample from an individual suffering from or suspected of (e.g., through a pre- or preliminary screening process) suffering from various disease states associated with abnormal glycan accumulation. Moreover, Table 14 further illustrates various glycan residual compounds that are liberated in various embodiments described herein, such liberated glycan residual compounds optionally being detected and/or measured in order to diagnose and/or monitor various disease states.

TABLE 14

| Disease | Non-Reducing End Structure | Primary Liberating Enzyme | Secondary Liberating Enzyme | Glycan Residual Compound |
|---|---|---|---|---|
| Alzheimers | Sialic Acid | Sialidase | | Sialic acid |
| Alzheimers | Sialic Acid | Alpha 2,8 Sialidase | | Sialic acid |
| Alzheimers | Sialic Acid | Alpha 2,3 Sialidase | | Sialic acid |
| Alzheimers | Sialic Acid | Alpha 2,6 Sialidase | | Sialic acid |
| Alzheimers | GalNAc | Hexosaminidase | | GalNAc |
| Alzheimers | GalNAc | Sialidase | Hexosaminidase | GalNAc |
| Alzheimers | Sialic acid | Hexosaminidase | Sialidase | Sialic acid |
| Alzheimers | Galactose | galactosidase | | Galactose |
| Alzheimers | Galactose | sialidase | galactosidase | Galactose |

TABLE 14-continued

| Disease | Non-Reducing End Structure | Primary Liberating Enzyme | Secondary Liberating Enzyme | Glycan Residual Compound |
|---|---|---|---|---|
| Alzheimers | Fucose | fucosidase | | Fucose |
| Alzheimers | Galactose | Galactosidase | | Galactose |
| Alzheimers | GlcNAc | hexosaminidase | | GlcNAc |
| Alzheimers | Sulfate | Sulfatase | | Sulfate |
| Alzheimers | Sulfated hexose | Sulfatase | hexosaminidase | GlcNAc or GalNAc |
| Alzheimers | Sulfated uronic acid | Sulfatase | Iduronidase or glucuronidase | IdoA or GlcA |
| Amyotrophic Lateral Sclerosis | Sialic Acid | Sialidase | | Sialic acid |
| Amyotrophic Lateral Sclerosis | Sialic Acid | Alpha 2,8 Sialidase | | Sialic acid |
| Amyotrophic Lateral Sclerosis | Sialic Acid | Alpha 2,3 Sialidase | | Sialic acid |
| Amyotrophic Lateral Sclerosis | Sialic Acid | Alpha 2,6 Sialidase | | Sialic acid |
| Amyotrophic Lateral Sclerosis | GalNAc | Hexosaminidase | | GalNAc |
| Amyotrophic Lateral Sclerosis | GalNAc | Sialidase | Hexosaminidase | GalNAc |
| Amyotrophic Lateral Sclerosis | Sialic acid | Hexosaminidase | Sialidase | Sialic acid |
| Amyotrophic Lateral Sclerosis | Galactose | galactosidase | | Galactose |
| Amyotrophic Lateral Sclerosis | Galactose | sialidase | galactosidase | Galactose |
| Amyotrophic Lateral Sclerosis | Fucose | fucosidase | | Fucose |
| Amyotrophic Lateral Sclerosis | Galactose | Galactosidase | | Galactose |
| Amyotrophic Lateral Sclerosis | GlcNAc | hexosaminidase | | GlcNAc |
| Amyotrophic Lateral Sclerosis | Sulfate | Sulfatase | | Sulfate |
| Amyotrophic Lateral Sclerosis | Sulfated hexose | Sulfatase | hexosaminidase | GlcNAc or GalNAc |
| Amyotrophic Lateral Sclerosis | Sulfated uronic acid | Sulfatase | Iduronidase or glucuronidase | IdoA or GlcA |
| Cerebral Palsy | Sialic Acid | Sialidase | | Sialic acid |
| Cerebral Palsy | Sialic Acid | Alpha 2,8 Sialidase | | Sialic acid |
| Cerebral Palsy | Sialic Acid | Alpha 2,3 Sialidase | | Sialic acid |
| Cerebral Palsy | Sialic Acid | Alpha 2,6 Sialidase | | Sialic acid |
| Cerebral Palsy | GalNAc | Hexosaminidase | | GalNAc |
| Cerebral Palsy | GalNAc | Sialidase | Hexosaminidase | GalNAc |
| Cerebral Palsy | Sialic acid | Hexosaminidase | Sialidase | Sialic acid |
| Cerebral Palsy | Galactose | galactosidase | | Galactose |
| Cerebral Palsy | Galactose | sialidase | galactosidase | Galactose |
| Cerebral Palsy | Fucose | fucosidase | | Fucose |
| Cerebral Palsy | Galactose | Galactosidase | | Galactose |
| Cerebral Palsy | GlcNAc | hexosaminidase | | GlcNAc |
| Cerebral Palsy | Sulfate | Sulfatase | | Sulfate |
| Cerebral Palsy | Sulfated hexose | Sulfatase | hexosaminidase | GlcNAc or GalNAc |
| Cerebral Palsy | Sulfated uronic acid | Sulfatase | Iduronidase or glucuronidase | IdoA or GlcA |
| Schizophrenia | Sialic Acid | Sialidase | | Sialic acid |
| Schizophrenia | Sialic Acid | Alpha 2,8 Sialidase | | Sialic acid |
| Schizophrenia | Sialic Acid | Alpha 2,3 Sialidase | | Sialic acid |
| Schizophrenia | Sialic Acid | Alpha 2,6 Sialidase | | Sialic acid |
| Schizophrenia | GalNAc | Hexosaminidase | | GalNAc |
| Schizophrenia | GalNAc | Sialidase | Hexosaminidase | GalNAc |
| Schizophrenia | Sialic acid | Hexosaminidase | Sialidase | Sialic acid |
| Schizophrenia | Galactose | galactosidase | | Galactose |
| Schizophrenia | Galactose | sialidase | galactosidase | Galactose |
| Schizophrenia | Fucose | fucosidase | | Fucose |
| Schizophrenia | Galactose | Galactosidase | | Galactose |
| Schizophrenia | GlcNAc | hexosaminidase | | GlcNAc |
| Schizophrenia | Sulfate | Sulfatase | | Sulfate |
| Schizophrenia | Sulfated hexose | Sulfatase | hexosaminidase | GlcNAc or GalNAc |

TABLE 14-continued

| Disease | Non-Reducing End Structure | Primary Liberating Enzyme | Secondary Liberating Enzyme | Glycan Residual Compound |
|---|---|---|---|---|
| Schizophrenia | Sulfated uronic acid | Sulfatase | Iduronidase or glucouronidase | IdoA or GlcA |
| Bipolar Disorder | Sialic Acid | Sialidase | | Sialic acid |
| Bipolar Disorder | Sialic Acid | Alpha 2,8 Sialidase | | Sialic acid |
| Bipolar Disorder | Sialic Acid | Alpha 2,3 Sialidase | | Sialic acid |
| Bipolar Disorder | Sialic Acid | Alpha 2,6 Sialidase | | Sialic acid |
| Bipolar Disorder | GalNAc | Hexosaminidase | | GalNAc |
| Bipolar Disorder | GalNAc | Sialidase | Hexosaminidase | GalNAc |
| Bipolar Disorder | Sialic acid | Hexosaminidase | Sialidase | Sialic acid |
| Bipolar Disorder | Galactose | galactosidase | | Galactose |
| Bipolar Disorder | Galactose | sialidase | galactosidase | Galactose |
| Bipolar Disorder | Fucose | fucosidase | | Fucose |
| Bipolar Disorder | Galactose | Galactosidase | | Galactose |
| Bipolar Disorder | GlcNAc | hexosaminidase | | GlcNAc |
| Bipolar Disorder | Sulfate | Sulfatase | | Sulfate |
| Bipolar Disorder | Sulfated hexose | Sulfatase | hexosaminidase | GlcNAc or GalNAc |
| Bipolar Disorder | Sulfated uronic acid | Sulfatase | Iduronidase or glucouronidase | IdoA or GlcA |
| Depression | Sialic Acid | Sialidase | | Sialic acid |
| Depression | Sialic Acid | Alpha 2,8 Sialidase | | Sialic acid |
| Depression | Sialic Acid | Alpha 2,3 Sialidase | | Sialic acid |
| Depression | Sialic Acid | Alpha 2,6 Sialidase | | Sialic acid |
| Depression | GalNAc | Hexosaminidase | | GalNAc |
| Depression | GalNAc | Sialidase | Hexosaminidase | GalNAc |
| Depression | Sialic acid | Hexosaminidase | Sialidase | Sialic acid |
| Depression | Galactose | galactosidase | | Galactose |
| Depression | Galactose | sialidase | galactosidase | Galactose |
| Depression | Fucose | fucosidase | | Fucose |
| Depression | Galactose | Galactosidase | | Galactose |
| Depression | GlcNAc | hexosaminidase | | GlcNAc |
| Depression | Sulfate | Sulfatase | | Sulfate |
| Depression | Sulfated hexose | Sulfatase | hexosaminidase | GlcNAc or GalNAc |
| Depression | Sulfated uronic acid | Sulfatase | Iduronidase or glucouronidase | IdoA or GlcA |
| Epilepsy | Sialic Acid | Sialidase | | Sialic acid |
| Epilepsy | Sialic Acid | Alpha 2,8 Sialidase | | Sialic acid |
| Epilepsy | Sialic Acid | Alpha 2,3 Sialidase | | Sialic acid |
| Epilepsy | Sialic Acid | Alpha 2,6 Sialidase | | Sialic acid |
| Epilepsy | GalNAc | Hexosaminidase | | GalNAc |
| Epilepsy | GalNAc | Sialidase | Hexosaminidase | GalNAc |
| Epilepsy | Sialic acid | Hexosaminidase | Sialidase | Sialic acid |
| Epilepsy | Galactose | galactosidase | | Galactose |
| Epilepsy | Galactose | sialidase | galactosidase | Galactose |
| Epilepsy | Fucose | fucosidase | | Fucose |
| Epilepsy | Galactose | Galactosidase | | Galactose |
| Epilepsy | GlcNAc | hexosaminidase | | GlcNAc |
| Epilepsy | Sulfate | Sulfatase | | Sulfate |
| Epilepsy | Sulfated hexose | Sulfatase | hexosaminidase | GlcNAc or GalNAc |
| Epilepsy | Sulfated uronic acid | Sulfatase | Iduronidase or glucouronidase | IdoA or GlcA |
| Migraine | Sialic Acid | Sialidase | | Sialic acid |
| Migraine | Sialic Acid | Alpha 2,8 Sialidase | | Sialic acid |
| Migraine | Sialic Acid | Alpha 2,3 Sialidase | | Sialic acid |
| Migraine | Sialic Acid | Alpha 2,6 Sialidase | | Sialic acid |
| Migraine | GalNAc | Hexosaminidase | | GalNAc |
| Migraine | GalNAc | Sialidase | Hexosaminidase | GalNAc |
| Migraine | Sialic acid | Hexosaminidase | Sialidase | Sialic acid |
| Migraine | Galactose | galactosidase | | Galactose |
| Migraine | Galactose | sialidase | galactosidase | Galactose |
| Migraine | Fucose | fucosidase | | Fucose |
| Migraine | Galactose | Galactosidase | | Galactose |

TABLE 14-continued

| Disease | Non-Reducing End Structure | Primary Liberating Enzyme | Secondary Liberating Enzyme | Glycan Residual Compound |
|---|---|---|---|---|
| Migraine | GlcNAc | hexosaminidase | | GlcNAc |
| Migraine | Sulfate | Sulfatase | | Sulfate |
| Migraine | Sulfated hexose | Sulfatase | hexosaminidase | GlcNAc or GalNAc |
| Migraine | Sulfated uronic acid | Sulfatase | Iduronidase or glucouronidase | IdoA or GlcA |
| Multiple Sclerosis | Sialic Acid | Sialidase | | Sialic acid |
| Multiple Sclerosis | Sialic Acid | Alpha 2,8 Sialidase | | Sialic acid |
| Multiple Sclerosis | Sialic Acid | Alpha 2,3 Sialidase | | Sialic acid |
| Multiple Sclerosis | Sialic Acid | Alpha 2,6 Sialidase | | Sialic acid |
| Multiple Sclerosis | GalNAc | Hexosaminidase | | GalNAc |
| Multiple Sclerosis | GalNAc | Sialidase | Hexosaminidase | GalNAc |
| Multiple Sclerosis | Sialic acid | Hexosaminidase | Sialidase | Sialic acid |
| Multiple Sclerosis | Galactose | galactosidase | | Galactose |
| Multiple Sclerosis | Galactose | sialidase | galactosidase | Galactose |
| Multiple Sclerosis | Fucose | fucosidase | | Fucose |
| Multiple Sclerosis | Galactose | Galactosidase | | Galactose |
| Multiple Sclerosis | GlcNAc | hexosaminidase | | GlcNAc |
| Multiple Sclerosis | Sulfate | Sulfatase | | Sulfate |
| Multiple Sclerosis | Sulfated hexose | Sulfatase | hexosaminidase | GlcNAc or GalNAc |
| Multiple Sclerosis | Sulfated uronic acid | Sulfatase | Iduronidase or glucouronidase | IdoA or GlcA |
| Parkinson's | Sialic Acid | Sialidase | | Sialic acid |
| Parkinson's | Sialic Acid | Alpha 2,8 Sialidase | | Sialic acid |
| Parkinson's | Sialic Acid | Alpha 2,3 Sialidase | | Sialic acid |
| Parkinson's | Sialic Acid | Alpha 2,6 Sialidase | | Sialic acid |
| Parkinson's | GalNAc | Hexosaminidase | | GalNAc |
| Parkinson's | GalNAc | Sialidase | Hexosaminidase | GalNAc |
| Parkinson's | Sialic acid | Hexosaminidase | Sialidase | Sialic acid |
| Parkinson's | Galactose | galactosidase | | Galactose |
| Parkinson's | Galactose | sialidase | galactosidase | Galactose |
| Parkinson's | Fucose | fucosidase | | Fucose |
| Parkinson's | Galactose | Galactosidase | | Galactose |
| Parkinson's | GlcNAc | hexosaminidase | | GlcNAc |
| Parkinson's | Sulfate | Sulfatase | | Sulfate |
| Parkinson's | Sulfated hexose | Sulfatase | hexosaminidase | GlcNAc or GalNAc |
| Parkinson's | Sulfated uronic acid | Sulfatase | Iduronidase or glucouronidase | IdoA or GlcA |
| Rheumatoid Arthritis | Sialic Acid | Sialidase | | Sialic acid |
| Rheumatoid Arthritis | Sialic Acid | Alpha 2,8 Sialidase | | Sialic acid |
| Rheumatoid Arthritis | Sialic Acid | Alpha 2,3 Sialidase | | Sialic acid |
| Rheumatoid Arthritis | Sialic Acid | Alpha 2,6 Sialidase | | Sialic acid |
| Rheumatoid Arthritis | GalNAc | Hexosaminidase | | GalNAc |
| Rheumatoid Arthritis | GalNAc | Sialidase | Hexosaminidase | GalNAc |
| Rheumatoid Arthritis | Sialic acid | Hexosaminidase | Sialidase | Sialic acid |
| Rheumatoid Arthritis | Galactose | galactosidase | | Galactose |
| Rheumatoid Arthritis | Galactose | sialidase | galactosidase | Galactose |
| Rheumatoid Arthritis | Fucose | fucosidase | | Fucose |
| Rheumatoid Arthritis | Galactose | Galactosidase | | Galactose |
| Rheumatoid Arthritis | GlcNAc | hexosaminidase | | GlcNAc |
| Rheumatoid Arthritis | Sulfate | Sulfatase | | Sulfate |
| Rheumatoid Arthritis | Sulfated hexose | Sulfatase | hexosaminidase | GlcNAc or GalNAc |
| Rheumatoid Arthritis | Sulfated uronic acid | Sulfatase | Iduronidase or glucouronidase | IdoA or GlcA |
| Psoriatic Arthritis | Sialic Acid | Sialidase | | Sialic acid |
| Psoriatic Arthritis | Sialic Acid | Alpha 2,8 Sialidase | | Sialic acid |
| Psoriatic Arthritis | Sialic Acid | Alpha 2,3 Sialidase | | Sialic acid |
| Psoriatic Arthritis | Sialic Acid | Alpha 2,6 Sialidase | | Sialic acid |
| Psoriatic Arthritis | GalNAc | Hexosaminidase | | GalNAc |
| Psoriatic Arthritis | GalNAc | Sialidase | Hexosaminidase | GalNAc |
| Psoriatic Arthritis | Sialic acid | Hexosaminidase | Sialidase | Sialic acid |

TABLE 14-continued

| Disease | Non-Reducing End Structure | Primary Liberating Enzyme | Secondary Liberating Enzyme | Glycan Residual Compound |
|---|---|---|---|---|
| Psoriatic Arthritis | Galactose | galactosidase | | Galactose |
| Psoriatic Arthritis | Galactose | sialidase | galactosidase | Galactose |
| Psoriatic Arthritis | Fucose | fucosidase | | Fucose |
| Psoriatic Arthritis | Galactose | Galactosidase | | Galactose |
| Psoriatic Arthritis | GlcNAc | hexosaminidase | | GlcNAc |
| Psoriatic Arthritis | Sulfate | Sulfatase | | Sulfate |
| Psoriatic Arthritis | Sulfated hexose | Sulfatase | hexosaminidase | GlcNAc or GalNAc |
| Psoriatic Arthritis | Sulfated uronic acid | Sulfatase | Iduronidase or glucouronidase | IdoA or GlcA |
| Asthma | Sialic Acid | Sialidase | | Sialic acid |
| Asthma | Sialic Acid | Alpha 2,8 Sialidase | | Sialic acid |
| Asthma | Sialic Acid | Alpha 2,3 Sialidase | | Sialic acid |
| Asthma | Sialic Acid | Alpha 2,6 Sialidase | | Sialic acid |
| Asthma | GalNAc | Hexosaminidase | | GalNAc |
| Asthma | GalNAc | Sialidase | Hexosaminidase | GalNAc |
| Asthma | Sialic acid | Hexosaminidase | Sialidase | Sialic acid |
| Asthma | Galactose | galactosidase | | Galactose |
| Asthma | Galactose | sialidase | galactosidase | Galactose |
| Asthma | Fucose | fucosidase | | Fucose |
| Asthma | Galactose | Galactosidase | | Galactose |
| Asthma | GlcNAc | hexosaminidase | | GlcNAc |
| Asthma | Sulfate | Sulfatase | | Sulfate |
| Asthma | Sulfated hexose | Sulfatase | hexosaminidase | GlcNAc or GalNAc |
| Asthma | Sulfated uronic acid | Sulfatase | Iduronidase or glucouronidase | IdoA or GlcA |
| Chronic Obstructive Pulmonary Disorder | Sialic Acid | Sialidase | | Sialic acid |
| Chronic Obstructive Pulmonary Disorder | Sialic Acid | Alpha 2,8 Sialidase | | Sialic acid |
| Chronic Obstructive Pulmonary Disorder | Sialic Acid | Alpha 2,3 Sialidase | | Sialic acid |
| Chronic Obstructive Pulmonary Disorder | Sialic Acid | Alpha 2,6 Sialidase | | Sialic acid |
| Chronic Obstructive Pulmonary Disorder | GalNAc | Hexosaminidase | | GalNAc |
| Chronic Obstructive Pulmonary Disorder | GalNAc | Sialidase | Hexosaminidase | GalNAc |
| Chronic Obstructive Pulmonary Disorder | Sialic acid | Hexosaminidase | Sialidase | Sialic acid |
| Chronic Obstructive Pulmonary Disorder | Galactose | galactosidase | | Galactose |
| Chronic Obstructive Pulmonary Disorder | Galactose | sialidase | galactosidase | Galactose |
| Chronic Obstructive Pulmonary Disorder | Fucose | fucosidase | | Fucose |
| Chronic Obstructive Pulmonary Disorder | Galactose | Galactosidase | | Galactose |
| Chronic Obstructive Pulmonary Disorder | GlcNAc | hexosaminidase | | GlcNAc |
| Chronic Obstructive Pulmonary Disorder | Sulfate | Sulfatase | | Sulfate |
| Chronic Obstructive Pulmonary Disorder | Sulfated hexose | Sulfatase | hexosaminidase | GlcNAc or GalNAc |
| Chronic Obstructive Pulmonary Disorder | Sulfated uronic acid | Sulfatase | Iduronidase or glucouronidase | IdoA or GlcA |
| Lupus | Sialic Acid | Sialidase | | Sialic acid |
| Lupus | Sialic Acid | Alpha 2,8 Sialidase | | Sialic acid |
| Lupus | Sialic Acid | Alpha 2,3 Sialidase | | Sialic acid |
| Lupus | Sialic Acid | Alpha 2,6 Sialidase | | Sialic acid |
| Lupus | GalNAc | Hexosaminidase | | GalNAc |
| Lupus | GalNAc | Sialidase | Hexosaminidase | GalNAc |
| Lupus | Sialic acid | Hexosaminidase | Sialidase | Sialic acid |
| Lupus | Galactose | galactosidase | | Galactose |
| Lupus | Galactose | sialidase | galactosidase | Galactose |
| Lupus | Fucose | fucosidase | | Fucose |
| Lupus | Galactose | Galactosidase | | Galactose |
| Lupus | GlcNAc | hexosaminidase | | GlcNAc |
| Lupus | Sulfate | Sulfatase | | Sulfate |

TABLE 14-continued

| Disease | Non-Reducing End Structure | Primary Liberating Enzyme | Secondary Liberating Enzyme | Glycan Residual Compound |
|---|---|---|---|---|
| Lupus | Sulfated hexose | Sulfatase | hexosaminidase | GlcNAc or GalNAc |
| Lupus | Sulfated uronic acid | Sulfatase | Iduronidase or glucouronidase | IdoA or GlcA |
| Hepatitis | Sialic Acid | Sialidase | | Sialic acid |
| Hepatitis | Sialic Acid | Alpha 2,8 Sialidase | | Sialic acid |
| Hepatitis | Sialic Acid | Alpha 2,3 Sialidase | | Sialic acid |
| Hepatitis | Sialic Acid | Alpha 2,6 Sialidase | | Sialic acid |
| Hepatitis | GalNAc | Hexosaminidase | | GalNAc |
| Hepatitis | GalNAc | Sialidase | Hexosaminidase | GalNAc |
| Hepatitis | Sialic acid | Hexosaminidase | Sialidase | Sialic acid |
| Hepatitis | Galactose | galactosidase | | Galactose |
| Hepatitis | Galactose | sialidase | galactosidase | Galactose |
| Hepatitis | Fucose | fucosidase | | Fucose |
| Hepatitis | Galactose | Galactosidase | | Galactose |
| Hepatitis | GlcNAc | hexosaminidase | | GlcNAc |
| Hepatitis | Sulfate | Sulfatase | | Sulfate |
| Hepatitis | Sulfated hexose | Sulfatase | hexosaminidase | GlcNAc or GalNAc |
| Hepatitis | Sulfated uronic acid | Sulfatase | Iduronidase or glucouronidase | IdoA or GlcA |
| Renal Disease | Sialic Acid | Sialidase | | Sialic acid |
| Renal Disease | Sialic Acid | Alpha 2,8 Sialidase | | Sialic acid |
| Renal Disease | Sialic Acid | Alpha 2,3 Sialidase | | Sialic acid |
| Renal Disease | Sialic Acid | Alpha 2,6 Sialidase | | Sialic acid |
| Renal Disease | GalNAc | Hexosaminidase | | GalNAc |
| Renal Disease | GalNAc | Sialidase | Hexosaminidase | GalNAc |
| Renal Disease | Sialic acid | Hexosaminidase | Sialidase | Sialic acid |
| Renal Disease | Galactose | galactosidase | | Galactose |
| Renal Disease | Galactose | sialidase | galactosidase | Galactose |
| Renal Disease | Fucose | fucosidase | | Fucose |
| Renal Disease | Galactose | Galactosidase | | Galactose |
| Renal Disease | GlcNAc | hexosaminidase | | GlcNAc |
| Renal Disease | Sulfate | Sulfatase | | Sulfate |
| Renal Disease | Sulfated hexose | Sulfatase | hexosaminidase | GlcNAc or GalNAc |
| Renal Disease | Sulfated uronic acid | Sulfatase | Iduronidase or glucouronidase | IdoA or GlcA |
| Sickle Cell Disease | Sialic Acid | Sialidase | | Sialic acid |
| Sickle Cell Disease | Sialic Acid | Alpha 2,8 Sialidase | | Sialic acid |
| Sickle Cell Disease | Sialic Acid | Alpha 2,3 Sialidase | | Sialic acid |
| Sickle Cell Disease | Sialic Acid | Alpha 2,6 Sialidase | | Sialic acid |
| Sickle Cell Disease | GalNAc | Hexosaminidase | | GalNAc |
| Sickle Cell Disease | GalNAc | Sialidase | Hexosaminidase | GalNAc |
| Sickle Cell Disease | Sialic acid | Hexosaminidase | Sialidase | Sialic acid |
| Sickle Cell Disease | Galactose | galactosidase | | Galactose |
| Sickle Cell Disease | Galactose | sialidase | galactosidase | Galactose |
| Sickle Cell Disease | Fucose | fucosidase | | Fucose |
| Sickle Cell Disease | Galactose | Galactosidase | | Galactose |
| Sickle Cell Disease | GlcNAc | hexosaminidase | | GlcNAc |
| Sickle Cell Disease | Sulfate | Sulfatase | | Sulfate |
| Sickle Cell Disease | Sulfated hexose | Sulfatase | hexosaminidase | GlcNAc or GalNAc |
| Sickle Cell Disease | Sulfated uronic acid | Sulfatase | Iduronidase or glucouronidase | IdoA or GlcA |
| Fibromyalgia | Sialic Acid | Sialidase | | Sialic acid |
| Fibromyalgia | Sialic Acid | Alpha 2,8 Sialidase | | Sialic acid |
| Fibromyalgia | Sialic Acid | Alpha 2,3 Sialidase | | Sialic acid |
| Fibromyalgia | Sialic Acid | Alpha 2,6 Sialidase | | Sialic acid |
| Fibromyalgia | GalNAc | Hexosaminidase | | GalNAc |
| Fibromyalgia | GalNAc | Sialidase | Hexosaminidase | GalNAc |
| Fibromyalgia | Sialic acid | Hexosaminidase | Sialidase | Sialic acid |
| Fibromyalgia | Galactose | galactosidase | | Galactose |
| Fibromyalgia | Galactose | sialidase | galactosidase | Galactose |

TABLE 14-continued

| Disease | Non-Reducing End Structure | Primary Liberating Enzyme | Secondary Liberating Enzyme | Glycan Residual Compound |
|---|---|---|---|---|
| Fibromyalgia | Fucose | fucosidase | | Fucose |
| Fibromyalgia | Galactose | Galactosidase | | Galactose |
| Fibromyalgia | GlcNAc | hexosaminidase | | GlcNAc |
| Fibromyalgia | Sulfate | Sulfatase | | Sulfate |
| Fibromyalgia | Sulfated hexose | Sulfatase | hexosaminidase | GlcNAc or GalNAc |
| Fibromyalgia | Sulfated uronic acid | Sulfatase | Iduronidase or glucouronidase | IdoA or GlcA |
| Irritable Bowel Syndrome | Sialic Acid | Sialidase | | Sialic acid |
| Irritable Bowel Syndrome | Sialic Acid | Alpha 2,8 Sialidase | | Sialic acid |
| Irritable Bowel Syndrome | Sialic Acid | Alpha 2,3 Sialidase | | Sialic acid |
| Irritable Bowel Syndrome | Sialic Acid | Alpha 2,6 Sialidase | | Sialic acid |
| Irritable Bowel Syndrome | GalNAc | Hexosaminidase | | GalNAc |
| Irritable Bowel Syndrome | GalNAc | Sialidase | Hexosaminidase | GalNAc |
| Irritable Bowel Syndrome | Sialic acid | Hexosaminidase | Sialidase | Sialic acid |
| Irritable Bowel Syndrome | Galactose | galactosidase | | Galactose |
| Irritable Bowel Syndrome | Galactose | sialidase | galactosidase | Galactose |
| Irritable Bowel Syndrome | Fucose | fucosidase | | Fucose |
| Irritable Bowel Syndrome | Galactose | Galactosidase | | Galactose |
| Irritable Bowel Syndrome | GlcNAc | hexosaminidase | | GlcNAc |
| Irritable Bowel Syndrome | Sulfate | Sulfatase | | Sulfate |
| Irritable Bowel Syndrome | Sulfated hexose | Sulfatase | hexosaminidase | GlcNAc or GalNAc |
| Irritable Bowel Syndrome | Sulfated uronic acid | Sulfatase | Iduronidase or glucouronidase | IdoA or GlcA |
| Ulcer | Sialic Acid | Sialidase | | Sialic acid |
| Ulcer | Sialic Acid | Alpha 2,8 Sialidase | | Sialic acid |
| Ulcer | Sialic Acid | Alpha 2,3 Sialidase | | Sialic acid |
| Ulcer | Sialic Acid | Alpha 2,6 Sialidase | | Sialic acid |
| Ulcer | GalNAc | Hexosaminidase | | GalNAc |
| Ulcer | GalNAc | Sialidase | Hexosaminidase | GalNAc |
| Ulcer | Sialic acid | Hexosaminidase | Sialidase | Sialic acid |
| Ulcer | Galactose | galactosidase | | Galactose |
| Ulcer | Galactose | sialidase | galactosidase | Galactose |
| Ulcer | Fucose | fucosidase | | Fucose |
| Ulcer | Galactose | Galactosidase | | Galactose |
| Ulcer | GlcNAc | hexosaminidase | | GlcNAc |
| Ulcer | Sulfate | Sulfatase | | Sulfate |
| Ulcer | Sulfated hexose | Sulfatase | hexosaminidase | GlcNAc or GalNAc |
| Ulcer | Sulfated uronic acid | Sulfatase | Iduronidase or glucouronidase | IdoA or GlcA |
| Irritable Bowel Disease | Sialic Acid | Sialidase | | Sialic acid |
| Irritable Bowel Disease | Sialic Acid | Alpha 2,8 Sialidase | | Sialic acid |
| Irritable Bowel Disease | Sialic Acid | Alpha 2,3 Sialidase | | Sialic acid |
| Irritable Bowel Disease | Sialic Acid | Alpha 2,6 Sialidase | | Sialic acid |
| Irritable Bowel Disease | GalNAc | Hexosaminidase | | GalNAc |
| Irritable Bowel Disease | GalNAc | Sialidase | Hexosaminidase | GalNAc |
| Irritable Bowel Disease | Sialic acid | Hexosaminidase | Sialidase | Sialic acid |
| Irritable Bowel Disease | Galactose | galactosidase | | Galactose |
| Irritable Bowel Disease | Galactose | sialidase | galactosidase | Galactose |
| Irritable Bowel Disease | Fucose | fucosidase | | Fucose |
| Irritable Bowel Disease | Galactose | Galactosidase | | Galactose |
| Irritable Bowel Disease | GlcNAc | hexosaminidase | | GlcNAc |
| Irritable Bowel Disease | Sulfate | Sulfatase | | Sulfate |
| Irritable Bowel Disease | Sulfated hexose | Sulfatase | hexosaminidase | GlcNAc or GalNAc |

TABLE 14-continued

| Disease | Non-Reducing End Structure | Primary Liberating Enzyme | Secondary Liberating Enzyme | Glycan Residual Compound |
|---|---|---|---|---|
| Irritable Bowel Disease | Sulfated uronic acid | Sulfatase | Iduronidase or glucuronidase | IdoA or GlcA |
| Coronary Artery Disease | Sialic Acid | Sialidase | | Sialic acid |
| Coronary Artery Disease | Sialic Acid | Alpha 2,8 Sialidase | | Sialic acid |
| Coronary Artery Disease | Sialic Acid | Alpha 2,3 Sialidase | | Sialic acid |
| Coronary Artery Disease | Sialic Acid | Alpha 2,6 Sialidase | | Sialic acid |
| Coronary Artery Disease | GalNAc | Hexosaminidase | | GalNAc |
| Coronary Artery Disease | GalNAc | Sialidase | Hexosaminidase | GalNAc |
| Coronary Artery Disease | Sialic acid | Hexosaminidase | Sialidase | Sialic acid |
| Coronary Artery Disease | Galactose | galactosidase | | Galactose |
| Coronary Artery Disease | Galactose | sialidase | galactosidase | Galactose |
| Coronary Artery Disease | Fucose | fucosidase | | Fucose |
| Coronary Artery Disease | Galactose | Galactosidase | | Galactose |
| Coronary Artery Disease | GlcNAc | hexosaminidase | | GlcNAc |
| Coronary Artery Disease | Sulfate | Sulfatase | | Sulfate |
| Coronary Artery Disease | Sulfated hexose | Sulfatase | hexosaminidase | GlcNAc or GalNAc |
| Coronary Artery Disease | Sulfated uronic acid | Sulfatase | Iduronidase or glucuronidase | IdoA or GlcA |
| Restenosis | Sialic Acid | Sialidase | | Sialic acid |
| Restenosis | Sialic Acid | Alpha 2,8 Sialidase | | Sialic acid |
| Restenosis | Sialic Acid | Alpha 2,3 Sialidase | | Sialic acid |
| Restenosis | Sialic Acid | Alpha 2,6 Sialidase | | Sialic acid |
| Restenosis | GalNAc | Hexosaminidase | | GalNAc |
| Restenosis | GalNAc | Sialidase | Hexosaminidase | GalNAc |
| Restenosis | Sialic acid | Hexosaminidase | Sialidase | Sialic acid |
| Restenosis | Galactose | galactosidase | | Galactose |
| Restenosis | Galactose | sialidase | galactosidase | Galactose |
| Restenosis | Fucose | fucosidase | | Fucose |
| Restenosis | Galactose | Galactosidase | | Galactose |
| Restenosis | GlcNAc | hexosaminidase | | GlcNAc |
| Restenosis | Sulfate | Sulfatase | | Sulfate |
| Restenosis | Sulfated hexose | Sulfatase | hexosaminidase | GlcNAc or GalNAc |
| Restenosis | Sulfated uronic acid | Sulfatase | Iduronidase or glucuronidase | IdoA or GlcA |
| Stroke | Sialic Acid | Sialidase | | Sialic acid |
| Stroke | Sialic Acid | Alpha 2,8 Sialidase | | Sialic acid |
| Stroke | Sialic Acid | Alpha 2,3 Sialidase | | Sialic acid |
| Stroke | Sialic Acid | Alpha 2,6 Sialidase | | Sialic acid |
| Stroke | GalNAc | Hexosaminidase | | GalNAc |
| Stroke | GalNAc | Sialidase | Hexosaminidase | GalNAc |
| Stroke | Sialic acid | Hexosaminidase | Sialidase | Sialic acid |
| Stroke | Galactose | galactosidase | | Galactose |
| Stroke | Galactose | sialidase | galactosidase | Galactose |
| Stroke | Fucose | fucosidase | | Fucose |
| Stroke | Galactose | Galactosidase | | Galactose |
| Stroke | GlcNAc | hexosaminidase | | GlcNAc |
| Stroke | Sulfate | Sulfatase | | Sulfate |
| Stroke | Sulfated hexose | Sulfatase | hexosaminidase | GlcNAc or GalNAc |
| Stroke | Sulfated uronic acid | Sulfatase | Iduronidase or glucuronidase | IdoA or GlcA |
| Diabetes | Sialic Acid | Sialidase | | Sialic acid |
| Diabetes | Sialic Acid | Alpha 2,8 Sialidase | | Sialic acid |
| Diabetes | Sialic Acid | Alpha 2,3 Sialidase | | Sialic acid |
| Diabetes | Sialic Acid | Alpha 2,6 Sialidase | | Sialic acid |
| Diabetes | GalNAc | Hexosaminidase | | GalNAc |
| Diabetes | GalNAc | Sialidase | Hexosaminidase | GalNAc |
| Diabetes | Sialic acid | Hexosaminidase | Sialidase | Sialic acid |
| Diabetes | Galactose | galactosidase | | Galactose |
| Diabetes | Galactose | sialidase | galactosidase | Galactose |
| Diabetes | Fucose | fucosidase | | Fucose |
| Diabetes | Galactose | Galactosidase | | Galactose |

TABLE 14-continued

| Disease | Non-Reducing End Structure | Primary Liberating Enzyme | Secondary Liberating Enzyme | Glycan Residual Compound |
|---|---|---|---|---|
| Diabetes | GlcNAc | hexosaminidase | | GlcNAc |
| Diabetes | Sulfate | Sulfatase | | Sulfate |
| Diabetes | Sulfated hexose | Sulfatase | hexosaminidase | GlcNAc or GalNAc |
| Diabetes | Sulfated uronic acid | Sulfatase | Iduronidase or glucouronidase | IdoA or GlcA |
| Hyperheparanemia | Sialic Acid | Sialidase | | Sialic acid |
| Hyperheparanemia | Sialic Acid | Alpha 2,8 Sialidase | | Sialic acid |
| Hyperheparanemia | Sialic Acid | Alpha 2,3 Sialidase | | Sialic acid |
| Hyperheparanemia | Sialic Acid | Alpha 2,6 Sialidase | | Sialic acid |
| Hyperheparanemia | GalNAc | Hexosaminidase | | GalNAc |
| Hyperheparanemia | GalNAc | Sialidase | Hexosaminidase | GalNAc |
| Hyperheparanemia | Sialic acid | Hexosaminidase | Sialidase | Sialic acid |
| Hyperheparanemia | Galactose | galactosidase | | Galactose |
| Hyperheparanemia | Galactose | sialidase | galactosidase | Galactose |
| Hyperheparanemia | Fucose | fucosidase | | Fucose |
| Hyperheparanemia | Galactose | Galactosidase | | Galactose |
| Hyperheparanemia | GlcNAc | hexosaminidase | | GlcNAc |
| Hyperheparanemia | Sulfate | Sulfatase | | Sulfate |
| Hyperheparanemia | Sulfated hexose | Sulfatase | hexosaminidase | GlcNAc or GalNAc |
| Hyperheparanemia | Sulfated uronic acid | Sulfatase | Iduronidase or glucouronidase | IdoA or GlcA |
| Hypergangliosidemia | Sialic Acid | Sialidase | | Sialic acid |
| Hypergangliosidemia | Sialic Acid | Alpha 2,8 Sialidase | | Sialic acid |
| Hypergangliosidemia | Sialic Acid | Alpha 2,3 Sialidase | | Sialic acid |
| Hypergangliosidemia | Sialic Acid | Alpha 2,6 Sialidase | | Sialic acid |
| Hypergangliosidemia | GalNAc | Hexosaminidase | | GalNAc |
| Hypergangliosidemia | GalNAc | Sialidase | Hexosaminidase | GalNAc |
| Hypergangliosidemia | Sialic acid | Hexosaminidase | Sialidase | Sialic acid |
| Hypergangliosidemia | Galactose | galactosidase | | Galactose |
| Hypergangliosidemia | Galactose | sialidase | galactosidase | Galactose |
| Hypergangliosidemia | Fucose | fucosidase | | Fucose |
| Hypergangliosidemia | Galactose | Galactosidase | | Galactose |
| Hypergangliosidemia | GlcNAc | hexosaminidase | | GlcNAc |
| Hypergangliosidemia | Sulfate | Sulfatase | | Sulfate |
| Hypergangliosidemia | Sulfated hexose | Sulfatase | hexosaminidase | GlcNAc or GalNAc |
| Hypergangliosidemia | Sulfated uronic acid | Sulfatase | Iduronidase or glucouronidase | IdoA or GlcA |
| Hypermucinemia | Sialic Acid | Sialidase | | Sialic acid |
| Hypermucinemia | Sialic Acid | Alpha 2,8 Sialidase | | Sialic acid |
| Hypermucinemia | Sialic Acid | Alpha 2,3 Sialidase | | Sialic acid |
| Hypermucinemia | Sialic Acid | Alpha 2,6 Sialidase | | Sialic acid |
| Hypermucinemia | GalNAc | Hexosaminidase | | GalNAc |
| Hypermucinemia | GalNAc | Sialidase | Hexosaminidase | GalNAc |
| Hypermucinemia | Sialic acid | Hexosaminidase | Sialidase | Sialic acid |
| Hypermucinemia | Galactose | galactosidase | | Galactose |
| Hypermucinemia | Galactose | sialidase | galactosidase | Galactose |
| Hypermucinemia | Fucose | fucosidase | | Fucose |
| Hypermucinemia | Galactose | Galactosidase | | Galactose |
| Hypermucinemia | GlcNAc | hexosaminidase | | GlcNAc |
| Hypermucinemia | Sulfate | Sulfatase | | Sulfate |
| Hypermucinemia | Sulfated hexose | Sulfatase | hexosaminidase | GlcNAc or GalNAc |
| Hypermucinemia | Sulfated uronic acid | Sulfatase | Iduronidase or glucouronidase | IdoA or GlcA |
| Hyper O-linked glycanemia | Sialic Acid | Sialidase | | Sialic acid |
| Hyper O-linked glycanemia | Sialic Acid | Alpha 2,8 Sialidase | | Sialic acid |
| Hyper O-linked glycanemia | Sialic Acid | Alpha 2,3 Sialidase | | Sialic acid |
| Hyper O-linked glycanemia | Sialic Acid | Alpha 2,6 Sialidase | | Sialic acid |
| Hyper O-linked glycanemia | GalNAc | Hexosaminidase | | GalNAc |

TABLE 14-continued

| Disease | Non-Reducing End Structure | Primary Liberating Enzyme | Secondary Liberating Enzyme | Glycan Residual Compound |
|---|---|---|---|---|
| Hyper O-linked glycanemia | GalNAc | Sialidase | Hexosaminidase | GalNAc |
| Hyper O-linked glycanemia | Sialic acid | Hexosaminidase | Sialidase | Sialic acid |
| Hyper O-linked glycanemia | Galactose | galactosidase | | Galactose |
| Hyper O-linked glycanemia | Galactose | sialidase | galactosidase | Galactose |
| Hyper O-linked glycanemia | Fucose | fucosidase | | Fucose |
| Hyper O-linked glycanemia | Galactose | Galactosidase | | Galactose |
| Hyper O-linked glycanemia | GlcNAc | hexosaminidase | | GlcNAc |
| Hyper O-linked glycanemia | Sulfate | Sulfatase | | Sulfate |
| Hyper O-linked glycanemia | Sulfated hexose | Sulfatase | hexosaminidase | GlcNAc or GalNAc |
| Hyper O-linked glycanemia | Sulfated uronic acid | Sulfatase | Iduronidase or glucouronidase | IdoA or GlcA |
| Hyper N-linked glycanemia | Sialic Acid | Sialidase | | Sialic acid |
| Hyper N-linked glycanemia | Sialic Acid | Alpha 2,8 Sialidase | | Sialic acid |
| Hyper N-linked glycanemia | Sialic Acid | Alpha 2,3 Sialidase | | Sialic acid |
| Hyper N-linked glycanemia | Sialic Acid | Alpha 2,6 Sialidase | | Sialic acid |
| Hyper N-linked glycanemia | GalNAc | Hexosaminidase | | GalNAc |
| Hyper N-linked glycanemia | GalNAc | Sialidase | Hexosaminidase | GalNAc |
| Hyper N-linked glycanemia | Sialic acid | Hexosaminidase | Sialidase | Sialic acid |
| Hyper N-linked glycanemia | Galactose | galactosidase | | Galactose |
| Hyper N-linked glycanemia | Galactose | sialidase | galactosidase | Galactose |
| Hyper N-linked glycanemia | Fucose | fucosidase | | Fucose |
| Hyper N-linked glycanemia | Galactose | Galactosidase | | Galactose |
| Hyper N-linked glycanemia | GlcNAc | hexosaminidase | | GlcNAc |
| Hyper N-linked glycanemia | Sulfate | Sulfatase | | Sulfate |
| Hyper N-linked glycanemia | Sulfated hexose | Sulfatase | hexosaminidase | GlcNAc or GalNAc |
| Hyper N-linked glycanemia | Sulfated uronic acid | Sulfatase | Iduronidase or glucouronidase | IdoA or GlcA |
| Hypersialylemia | Sialic Acid | Sialidase | | Sialic acid |
| Hypersialylemia | Sialic Acid | Alpha 2,8 Sialidase | | Sialic acid |
| Hypersialylemia | Sialic Acid | Alpha 2,3 Sialidase | | Sialic acid |
| Hypersialylemia | Sialic Acid | Alpha 2,6 Sialidase | | Sialic acid |
| Hypersialylemia | GalNAc | Hexosaminidase | | GalNAc |
| Hypersialylemia | GalNAc | Sialidase | Hexosaminidase | GalNAc |
| Hypersialylemia | Sialic acid | Hexosaminidase | Sialidase | Sialic acid |
| Hypersialylemia | Galactose | galactosidase | | Galactose |
| Hypersialylemia | Galactose | sialidase | galactosidase | Galactose |
| Hypersialylemia | Fucose | fucosidase | | Fucose |
| Hypersialylemia | Galactose | Galactosidase | | Galactose |
| Hypersialylemia | GlcNAc | hexosaminidase | | GlcNAc |
| Hypersialylemia | Sulfate | Sulfatase | | Sulfate |
| Hypersialylemia | Sulfated hexose | Sulfatase | hexosaminidase | GlcNAc or GalNAc |
| Hypersialylemia | Sulfated uronic acid | Sulfatase | Iduronidase or glucouronidase | IdoA or GlcA |
| Hyperfucosylemia | Sialic Acid | Sialidase | | Sialic acid |
| Hyperfucosylemia | Sialic Acid | Alpha 2,8 Sialidase | | Sialic acid |
| Hyperfucosylemia | Sialic Acid | Alpha 2,3 Sialidase | | Sialic acid |

TABLE 14-continued

| Disease | Non-Reducing End Structure | Primary Liberating Enzyme | Secondary Liberating Enzyme | Glycan Residual Compound |
|---|---|---|---|---|
| Hyperfucosylemia | Sialic Acid | Alpha 2,6 Sialidase | | Sialic acid |
| Hyperfucosylemia | GalNAc | Hexosaminidase | | GalNAc |
| Hyperfucosylemia | GalNAc | Sialidase | Hexosaminidase | GalNAc |
| Hyperfucosylemia | Sialic acid | Hexosaminidase | Sialidase | Sialic acid |
| Hyperfucosylemia | Galactose | galactosidase | | Galactose |
| Hyperfucosylemia | Galactose | sialidase | galactosidase | Galactose |
| Hyperfucosylemia | Fucose | fucosidase | | Fucose |
| Hyperfucosylemia | Galactose | Galactosidase | | Galactose |
| Hyperfucosylemia | GlcNAc | hexosaminidase | | GlcNAc |
| Hyperfucosylemia | Sulfate | Sulfatase | | Sulfate |
| Hyperfucosylemia | Sulfated hexose | Sulfatase | hexosaminidase | GlcNAc or GalNAc |
| Hyperfucosylemia | Sulfated uronic acid | Sulfatase | Iduronidase or glucouronidase | IdoA or GlcA |
| Hypersulfogycanemia | Sialic Acid | Sialidase | | Sialic acid |
| Hypersulfogycanemia | Sialic Acid | Alpha 2,8 Sialidase | | Sialic acid |
| Hypersulfogycanemia | Sialic Acid | Alpha 2,3 Sialidase | | Sialic acid |
| Hypersulfogycanemia | Sialic Acid | Alpha 2,6 Sialidase | | Sialic acid |
| Hypersulfogycanemia | GalNAc | Hexosaminidase | | GalNAc |
| Hypersulfogycanemia | GalNAc | Sialidase | Hexosaminidase | GalNAc |
| Hypersulfogycanemia | Sialic acid | Hexosaminidase | Sialidase | Sialic acid |
| Hypersulfogycanemia | Galactose | galactosidase | | Galactose |
| Hypersulfogycanemia | Galactose | sialidase | galactosidase | Galactose |
| Hypersulfogycanemia | Fucose | fucosidase | | Fucose |
| Hypersulfogycanemia | Galactose | Galactosidase | | Galactose |
| Hypersulfogycanemia | GlcNAc | hexosaminidase | | GlcNAc |
| Hypersulfogycanemia | Sulfate | Sulfatase | | Sulfate |
| Hypersulfogycanemia | Sulfated hexose | Sulfatase | hexosaminidase | GlcNAc or GalNAc |
| Hypersulfogycanemia | Sulfated uronic acid | Sulfatase | Iduronidase or glucouronidase | IdoA or GlcA |

Provided herein are methods of diagnosing individuals (including, e.g., a disease state or the severity of a disease states) with an infectious disease state associated with abnormal glycan accumulation. Provided in Table 15 are specific embodiments of disease that are optionally diagnosed and/or monitored according to various embodiments described herein. Table 15 also illustrates various non-limiting embodiments of specific enzyme(s) that are optionally utilized to treat a biological sample from an individual suffering from or suspected of (e.g., through a pre- or preliminary screening process) suffering from various infectious disease states associated with abnormal glycan accumulation. Moreover, Table 15 further illustrates various glycan residual compounds that are liberated in various embodiments described herein, such liberated glycan residual compounds optionally being detected and/or measured in order to diagnose and/or monitor various infectious disease states.

TABLE 15

Infectious Diseases

| Disease | Non-Reducing end structure | Primary Liberating Enzyme | Secondary Liberating Enzyme | Glycan Residual Compound |
|---|---|---|---|---|
| Bacterial Infections | Mannose | Mannosidase | | Mannose |
| Bacterial Infections | Fucose | Fucosidase | | Fucose |
| Bacterial Infections | Glucose | Glucosidase | | Glucose |
| Bacterial Infections | Galactose | Galactosidase | | Galactose |
| Bacterial Infections | GlcNAc | hexosaminidase | | GlcNAc |
| Bacterial Infections | GalNAc | hexosaminidase | | GalNAc |
| Bacterial Infections | Arabinose | Arabinosidase | | Arabinose |
| Bacterial Infections | Xylose | Xylosidase | | Xylose |
| Bacterial Infections | Ribose | Ribosidase | | Ribose |
| Bacterial Infections | Lyxose | Lyxosidase | | Lyxose |
| Bacterial Infections | Talose | Talosidase | | Talose |
| Bacterial Infections | Idose | Idosidase | | Idose |
| Bacterial Infections | Gulose | Gulosidase | | Gulose |
| Bacterial Infections | Altrose | Altrosidase | | Altrose |
| Bacterial Infections | Allose | Allosidase | | Allose |
| Fungal Infections | Mannose | Mannosidase | | Mannose |
| Fungal Infections | Fucose | Fucosidase | | Fucose |
| Fungal Infections | Glucose | Glucosidase | | Glucose |
| Fungal Infections | Galactose | Galactosidase | | Galactose |

TABLE 15-continued

Infectious Diseases

| Disease | Non-Reducing end structure | Primary Liberating Enzyme | Secondary Liberating Enzyme | Glycan Residual Compound |
|---|---|---|---|---|
| Fungal Infections | GlcNAc | hexosaminidase | | GlcNAc |
| Fungal Infections | GalNAc | hexosaminidase | | GalNAc |
| Fungal Infections | Arabinose | Arabinosidase | | Arabinose |
| Fungal Infections | Xylose | Xylosidase | | Xylose |
| Fungal Infections | Ribose | Ribosidase | | Ribose |
| Fungal Infections | Lyxose | Lyxosidase | | Lyxose |
| Fungal Infections | Talose | Talosidase | | Talose |
| Fungal Infections | Idose | Idosidase | | Idose |
| Fungal Infections | Gulose | Gulosidase | | Gulose |
| Fungal Infections | Altrose | Altrosidase | | Altrose |
| Fungal Infections | Allose | Allosidase | | Allose |
| Viral Infections | Sialic Acid | Sialidase | | Sialic acid |
| Viral Infections | Sialic Acid | Alpha 2,8 Sialidase | | Sialic acid |
| Viral Infections | Sialic Acid | Alpha 2,3 Sialidase | | Sialic acid |
| Viral Infections | Sialic Acid | Alpha 2,6 Sialidase | | Sialic acid |
| Viral Infections | GalNAc | Hexosaminidase | | GalNAc |
| Viral Infections | GalNAc | Sialidase | Hexosaminidase | GalNAc |
| Viral Infections | Sialic acid | Hexosaminidase | Sialidase | Sialic acid |
| Viral Infections | Galactose | galactosidase | | Galactose |
| Viral Infections | Galactose | sialidase | galactosidase | Galactose |
| Viral Infections | Fucose | fucosidase | | Fucose |
| Viral Infections | Galactose | Galactosidase | | Galactose |
| Viral Infections | GlcNAc | hexosaminidase | | GlcNAc |
| Viral Infections | Sulfate | Sulfatase | | Sulfate |
| Viral Infections | Sulfated hexose | Sulfatase | hexosaminidase | GlcNAc or GalNAc |
| Viral Infections | Sulfated uronic acid | Sulfatase | Iduronidase or glucouronidase | IdoA or GlcA |

Figure 2:
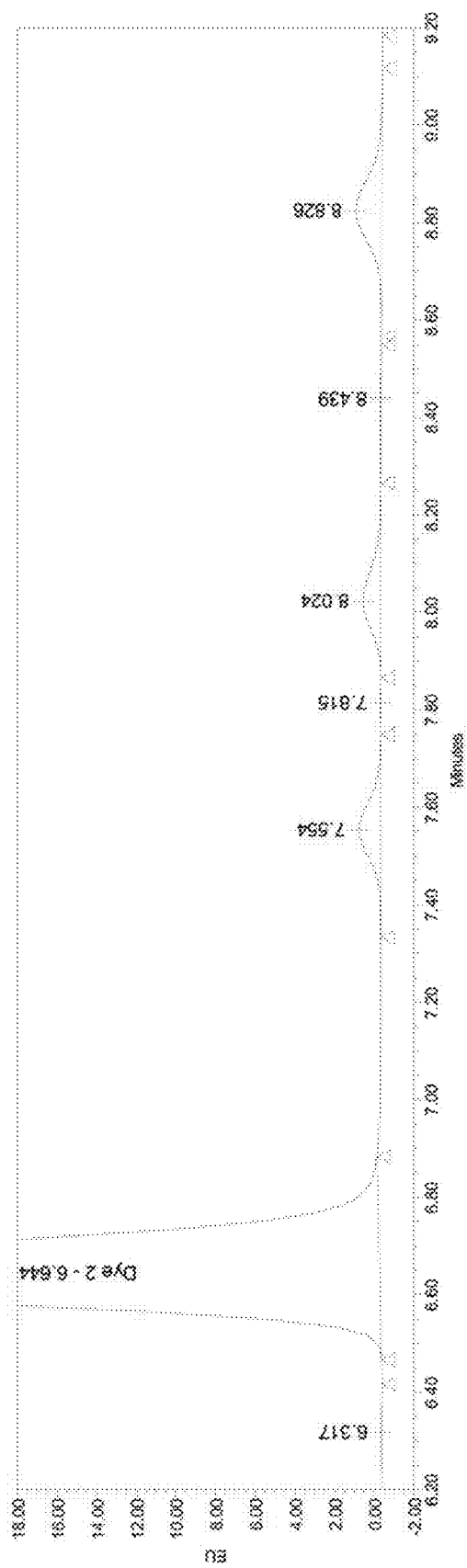
FIG. 2 illustrates compounds present in a normal biological subject to an enzymatic glycan residual liberation process described herein.
Figure 3:
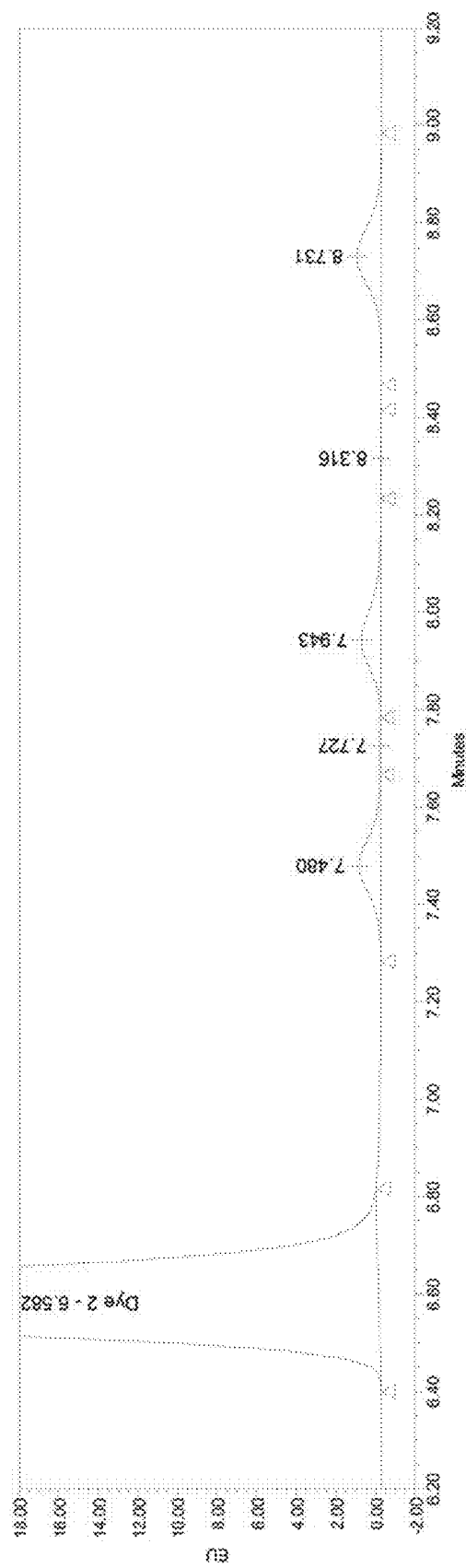
FIG. 3 illustrates compounds present in a biological sample of an individual suffering from a disorder associated with abnormal glycan accumulation not subject to an enzymatic glycan residual liberation process described herein.
Figure 4:
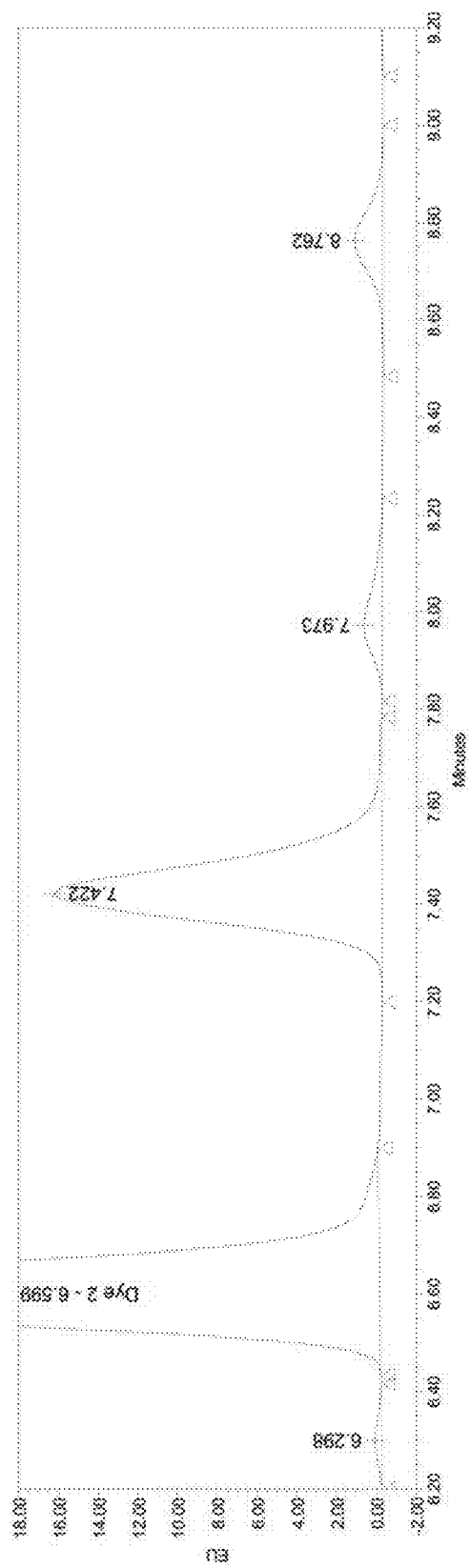
FIG. 4 illustrates compounds present in a biological sample of an individual suffering from a disorder associated with abnormal glycan accumulation subject to an enzymatic glycan residual liberation process described herein.
Figure 5:
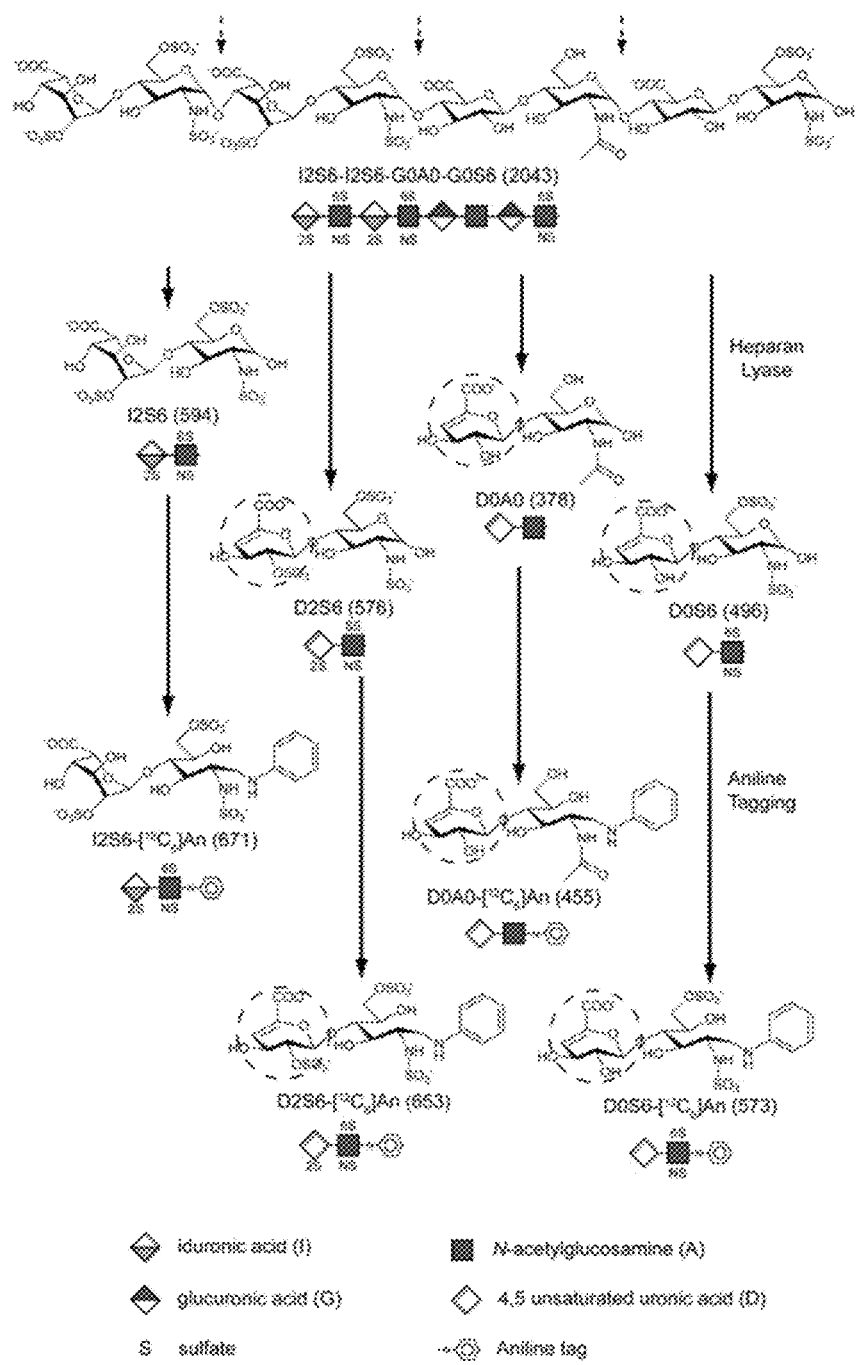
FIG. 5 illustrates a scheme for determining non-reducing ends and internal disaccharide. Eliminative depolymerization of a heparan sulfate oligosaccharide with heparan lyase results in the release of internal disaccharide residues (dashed arrows) that contain an unsaturated uronic acid moiety (dotted circles). Because of its terminal location, the non-reducing end liberated from the left end of the chain as drawn lacks the Δ4,5-double bond and is 18 amu larger than a corresponding internal disaccharide. Reductive amination with aniline ([12C$_6$]An) facilitates separation of the various disaccharides by LC/MS, yielding the m/z values for the molecular ions indicated within the parentheses. The glycan structures are graphically represented by geometric symbols, which are defined in the lower part of the FIG. 43. To simplify the representation of constituent oligosaccharides from glycosaminoglycans, we use a Disaccharide Structure Code (DSC) 15. In DSC, a uronic acid is designated as U, G, I, or D for an unspecified hexuronic acid, D-glucuronic acid, L-iduronic acid, or Δ4,5-unsaturated uronic acid, respectively. The hexosamines are designated in upper case for glucosamine and lower case for galactosamine, and the N-substituent is either H, A, S or R for hydrogen, acetate, sulfate, or some other substituent, respectively. The presence and location of ester linked sulfate groups are depicted by the number of the carbon atom on which the sulfate group is located or by 0 if absent. For example, I2S6 refers to a disaccharide composed of 2-sulfoiduronic acid-N-sulfoglucosamine-6-sulfate, whereas D2S6 refers to same disaccharide, but bearing a Δ4,5-double bond in the uronic acid.

FIG. 1 illustrates compounds present in a normal biological sample not subject to an enzymatic glycan residual liberation process described herein. FIG. 2 illustrates compounds present in a normal biological subject to an enzymatic glycan residual liberation process described herein. FIG. 3 illustrates compounds present in a biological sample of an individual suffering from a disorder associated with abnormal glycan accumulation not subject to an enzymatic glycan residual liberation process described herein. FIG. 4 illustrates compounds present in a biological sample of an individual suffering from a disorder associated with abnormal glycan accumulation subject to an enzymatic glycan residual liberation process described herein.

Detecting and Measuring:

Glycan residual compounds (including, e.g., oligosaccharides, monosaccharides, sulfate, phosphate, sialic acid, acetate, or the like) described herein are detected and/or measured in processes described herein in any suitable manner. In some embodiments, glycan residual compounds are detected and/or measured in unmodified form. In other embodiments, glycan residual compounds are tagged with a detectable label prior and the labeled glycan residual compound is detected.

In some embodiments, non-labeled compounds are optionally detected and/or measured in any suitable manner, e.g., by pH, by quantitative nuclear magnetic resonance (NMR), or the like.

In various embodiments, a method described herein comprises determining whether the amount of liberated glycan residue is abnormal and such a determination comprises labeling the glycan residue with a detectable label and measuring the amount of labeled glycan residue with an analytical instrument. In specific embodiments, the detectable label is a mass label, a radioisotope label, a fluorescent label, a chromophore label, or affinity label. In some embodiments, the amount of liberated glycan is measured using UV-Vis spectroscopy, IR spectroscopy, mass spectrometry, or a combination thereof.

In the various embodiments of any process or method described herein, any suitable detectable label is optionally utilized. In some embodiments, detectable labels useful in the processes or methods described herein include, by way of non-limiting example, mass labels, antibodies, affinity labels, radioisotope labels, chromophores, fluorescent labels, or the like.

Fluorescent labels suitable for use in various embodiments herein include, by way of non-limiting example, 2-aminopyridine (2-AP), 2-aminobenzoic acid (2-AA), 2-aminobenzamide (2-AB), 2-aminoacridone (AMAC), p-aminobenzoic acid ethyl ester (ABEE), p-aminobenzonitrile (ABN), 2-amino-6-cyanoethylpyridine (ACP), 7-amino-4-methylcoumarine (AMC), 8-aminonaphthalene-1,3,6-trisulfate (ANTS), 7-aminonaphthalene-1,3-disulfide (ANDS), and 8-aminopyrene-1,3,6-trisulfate (APTS), or the like. The fluorescent labels can be attached by reductive amination with the fluorescent label and sodium cyanoborohydride or the like.

Mass labels suitable for use in various embodiments herein include, by way of non-limiting example, D-2-anthranilic acid, D-2-aminopyridine, D-methyl iodide, $^{13}C$ methyl iodide, deuterated-pyridyl-amine, D-biotin or the like. The mass labels can be attached by permethylation or reductive amination by any method that is known to those of skill in the art.

Affinity labels suitable for use in various embodiments herein include, by way of non-limiting example, biotin and derivatives.

Radioisotope labels suitable for use in various embodiments herein include, by way of non-limiting example, sodium borotritide ($NaB^3H_4$), $^3H$, $^{14}C$, $^{32}P$, $^{35}S$, or the like.

Chromophores suitable for use in various embodiments herein include, by way of non-limiting example, 4-amino-1,1'-azobenzene, 4'-N,N-dimethylamino-4-aminoazobenzene, aminoazobenzene, diaminoazobenzene, Direct Red 16, CI Acid Red 57, CI Acid Blue 45, CI Acid Blue 22, CL Mordant Brown 13, CI Direct Orange 75, or the like. The chromophores may be labeled by any method that is known to those of skill in the art, such as reductive amination with the chromophore and sodium cyanoborohydride.

In some embodiments, the detectable label is an antibody. In specific embodiments, the antibody is attached to a detectable compound, such as mass labels, radioisotope labels, chromophores, fluorescent labels, or the like. In some embodiments, antibodies are themselves detected and/or are detectable in various manners, e.g., as a chromophore, a fluorophore, or the like; or with a probe (e.g., using dot blot techniques, immune-detection techniques, or the like).

In certain embodiments, detectable labels are detected and/or quantified according to any process described herein using any technique, particularly any technique suitable for the detectable label utilized. In some embodiments, suitable detection techniques include, by way of non-limiting example, one or more of a mass spectrometer, a nuclear magnetic resonance spectrometer, a UV-Vis spectrometer, an IR spectrometer, a fluorimeter, a phosphorimeter, a radiation spectrometer (e.g., a scintillation counter), a thin layer chromatographic technique, or the like. In certain embodiments, in any process described herein, glycan residual compounds are optionally directly detected using a suitable technique, such as quantitative nuclear magnetic resonance. Quantitative nuclear magnetic resonance is also optionally utilized to quantify and/or detect the presence of a detectable label. In certain embodiments, one or more glycan residual compounds are optionally detected using a suitable liquid chromatography mass spectrometer (LC-MS).

In some embodiments, glycan residual compounds are tagged with an antibody or probe, and are quantified using any suitable method (e.g., dot blot techniques, immune detection techniques (e.g., ELISA), or the like).

Various analytical methods useful for the processes described herein include, by way of non-limiting example, mass spectrometry, chromatography, HPLC, UPLC, TLC, GC, HPAEC-PAD, electrophoresis—capillary or gel, or the like. In certain embodiments, wherein a chromatographic technique is utilized, any suitable solvent system is optionally employed. In certain embodiments, a column (e.g., Cosmogel DEAE, Tsk Gel DEAE, Cosmogel QA, Cosmogel CM, Cosmogel SP, or the like) is optionally loaded with an equilibrating solvent (e.g., a buffer or salt solution, such as a potassium acetate solution, sodium chloride solution, sodium acetate solution, ammonium acetate solution, or the like), e.g., with a pH of about 6, 7, or 8. In some embodiments, the buffer or salt solution has a concentration of about 10 mM, 20 mM, 30 mM, 50 mM, 100 mM, 500 mM, 1 M, 2 M, or the like. Any suitable flow rate is used, e.g., 0.5 mL/min, 1 mL, min, 1.5 mL/min, 2 mL/min, or the like. Following equilibration, a linear gradient is optionally utilized. In some embodiments, the linear gradient is run over 1-20 min, 1-10 min, 10-20 min, 1-5 min, 5-10 min, or the like. In certain embodiments, the gradient is a buffer or salt solution, e.g., as described above (e.g., from 0 M to 0.5 M, from 0 M to 3 M, from 0.5 M to 2 M, from 0 M to 2 M, from 1M to 2M, from 0 M to 3 M, from 2 M to 0 M, from 3 M to 0 M, or the like). Once the gradient has reached a final concentration, the eluent is optionally held at the final concentration for a suitable period of time (e.g., 1-20 min, 5-10 min, 10-15 min, 1-5 min, 1-10 min, 15-20 min, or the like). After the optional holding of the final concentration, the eluent may be switched to a second solvent or solvent system (e.g., an alcohol, such as methanol, ethanol, or isopropanol, acetonitrile, water, or the like). The switch to the second solvent system may be over a period of time, e.g., 15 seconds, 30 seconds, 45 seconds, 60 seconds, 2 min, 3 min, or the like. The second solvent system is optionally held for a period of time, such as 1 min, 2 min, 3 min, 4 min, 5 min, 6 min, or the like. Following the second solvent system cycle, the column is optionally restored to initial solvent conditions.

Purification:

In certain embodiments, methods described herein comprise purifying a biological sample, e.g., to remove non-glycan compounds from the biological sample. In some embodiments, a biological sample is purified prior to transforming a glycan thereof.

In certain embodiments, a biological sample containing glycans (purified or not) can also be prepared so that all free glycan residual compounds (e.g., monosaccharides) that are naturally present in the biological sample (i.e., as taken from an individual and without being treated) are eliminated from the sample to reduce background signal (for example using dialysis, spin column, gel filtration, etc).

In some embodiments, any process described herein includes a step of purifying a biological sample comprising removing monosaccharides therefrom, removing sulfates therefrom, removing phosphates therefrom, removing acetate therefrom, removing sialic acid therefrom, or a combination thereof. For example, in some embodiments, a biological sample is optionally placed in to a defined MW cut off spin column (retains large molecules when spun), optionally washed (e.g., with 1 or more volumes of water or buffer), and/or the like.

In certain embodiments, purification of biological samples may further or alternatively comprise, e.g., fractionation, purification, enrichment, or the like of glycans contained therein. In some instances, such purification techniques are suitable to isolate and/or separate different glycan classes within the biological sample prior to transformation of one or more of such glycans. In more specific instances, such purification techniques are used to isolate and/or separate different subsets of a single glycan class (such as isolating complex N-linked glycans from hybrid N-linked structures) prior to transformation of one or more of such glycans. In certain embodiments, a biological sample is optionally prepared in such a way to enrich for specific glycan classes. For example, a PHA affinity column is optionally used to isolate a sub-fraction of complex N-linked glycans while a Con A column could be used to enrich in a different subset of N-linked glycans.

In some embodiments, any process described herein comprises purification of a glycan residual compound resulting from a process described herein (e.g., purification of the glycan residual compound prior to analysis thereof). For example, in some embodiments, the glycan residual compound is optionally isolated by any suitable process, such as by washing the free glycan residual compound (e.g., through a defined MW cut off membrane or by any other suitable method). Moreover, in certain embodiments, the resulting isolated glycan residual compound containing composition is optionally dried or otherwise treated to concentrate the sample and subsequently analyzed for glycan residual compound content by any suitable analytical technique.

In some embodiments, the processes described herein comprises further treatment steps of the test and/or control samples. For example, in some embodiments, the samples are homogenized and/or purified. In specific embodiments homogenization is achieved in any suitable manner including, by way of non-limiting example, with a basic solution, sonication, tissue grinding, or other chemical agents. In some embodiments, severity of a disorder is determined if a certain threshold amount is measured (e.g., as compared to a control or controls) or a threshold signal (e.g., on a fluorimeter or other analytical device utilized to detect and/or measure the generated biomarker). Similarly, a carrier of a disorder described herein is, in certain embodiments, determined if a certain threshold amount is measured (e.g., as compared to a control or controls) or a threshold signal (e.g., on a fluorimeter or other analytical device utilized to detect and/or measure the generated biomarker).

In certain embodiments, samples, including test samples and/or control samples, described herein are optionally purified prior to glycan processing (e.g., lyase treatment) and/or characterization. Test samples and/or control samples (i.e., one or more or all of the glycans found therein) are optionally purified using any suitable purification technique. Test samples and/or control samples are optionally purified at any suitable point in a process described herein, including before or after tagging of the glycans founds within the sample. In certain embodiments, purification techniques include centrifugation, electrophoresis, chromatography (e.g., silica gel or alumina column chromatography), gas chromatography, high performance liquid chromatography (HPLC) (e.g., reverse phase HPLC on chiral or achiral columns), thin layer chromatography, ion exchange chromatography, gel chromatography (e.g., gel filtration or permeation or size exclusion chromatography, gel electrophoresis), molecular sieve chromatography, affinity chromatography, size exclusion, filtration (e.g. through a florisil or activated charcoal plug), precipitation, osmosis, recrystallization, fluorous phase purification, distillation, extraction, chromatofocusing, supercritical fluid extraction, preparative flash chromatography (e.g., flash chromatography using a UV-Vis detector and/or a mass spectrometer (e.g., using the Biotage® suite of products) or the like.

In some embodiments, glycans, such as heparan sulfate, are naturally found attached to a core protein (together forming a proteoglycan) or a lipid. In some embodiments, provided herein are purification processes of separating glycan fragments (e.g., heparan sulfate fragments) from proteoglycans or glycolipids prior to processing the glycan for processing and analysis.

Monitoring Therapy

Provided in certain embodiments are methods of treating disorders associated with the abnormal degradation, biosynthesis and/or accumulation of glycans, the methods comprising:
 a. administering an agent for treating disorders associated with the abnormal degradation, biosynthesis and/or accumulation of glycans (e.g., an anti-LSD agent, an anti-cancer agent, or the like) to an individual in need thereof;
 b. monitoring the accumulation of glycans in the individual using any process described herein for detecting or quantifying the amount of glycan residual compounds (e.g., mono-saccharides, sulfate, or the like) present in a lyase digested biological sample (e.g., urine, serum, plasma, or CSF sample) according to any process described herein.

Provided in further or alternative embodiments are methods of monitoring the treatment of disorders associated with the abnormal degradation, biosynthesis and/or accumulation of glycans, the methods comprising the following steps:
 a. following administration of an agent for treating a disorder associated with the abnormal degradation, biosynthesis and/or accumulation of glycans (e.g., an anti-LSD agent, an anti-cancer agent, or the like) to an individual in need thereof, generating a biomarker comprising of one or more non-reducing end glycan residual compound (e.g., monosaccharide).

In some embodiments, the biomarker is a saturated monosaccharide and is generated by treating a population of glycans, in or isolated from a biological sample from the individual, with at least one digesting glycan enzymes, wherein prior to enzyme treatment, the biomarker is not present in abundance in samples from individuals with the disease or condition relative to individuals without the disease or condition. In certain embodiments, monitoring of the accumulation of glycans comprises using an analytical instrument to detect the presence of and/or measure the amount of the biomarker produced and displaying or recording the presence of or a measure of a population of the biomarker; wherein the presence of and/or measure the amount of the biomarker is utilized to monitor the treatment.

In some embodiments, the agent is administered one or more times. In certain embodiments, the agent is administered multiple times. In some embodiments, the agent is administered in a loading dose one or more times (e.g., in a loading dosing schedule) and subsequently administered in a maintenance dose (e.g., in a maintenance dosing schedule, such as three times a day, twice a day, once a day, once every two days, once every three days, once every four days, once a week, or the like). In some embodiments, when glycan (as measure by one or more glycan residual compound(s)) accumulation begins to increase or accelerate, the dose is optionally adjusted (e.g., the maintenance dose is increased, or an additional loading dose or dosing schedule is utilized).

In some embodiments, monitoring the accumulation of glycans comprises repeating the step of: using an analytical instrument to detect the presence of and/or measure the amount of a population of one or more glycan residual compounds present in a transformed biological sample that has been prepared by treating a population of glycans, in or isolated from a biological sample from the individual, with at least one digesting glycan lyase to transform the glycan into the population of the one or more glycan residual compounds. In specific embodiments, the step is repeated at periodic intervals (e.g., every day, every other day, every 2 days, every 3 days, every 4 days, every week, every month, every 3 months, quarterly, every 6 months, yearly, or the like), at regular times following a dose (e.g., 4 hours after a administration of the agent, 6 hours after administration of the agent, 8 hours after administration of the agent, 12 hours after administration of the agent, or the like), prior to administration of the dose (e.g., immediately prior to administration of the agent, 2 hours prior to administration of the agent, or the like), or any other monitoring schedule.

In some embodiments, the monitoring of the accumulation of glycan is conducted over a period of time, e.g., over a week, two weeks, a month, two months, three months, six months, a year, or the like. In some embodiments, the method for quantifying the amount of one or more glycan residual compounds in a lyase digested biological sample (e.g., urine, serum, plasma, or CSF) comprises detecting and/or measuring (e.g., with an analytical device), one or more glycan residual compounds within the lyase digested biological sample from the individual after the biological sample obtained from the individual has been treated with one or more glycan lyases. In certain embodiments, such glycan lyases are suitable for preparing glycan residual compounds from the glycan present in the biological sample obtained from the individual. In certain instances a representative portion of the one or more glycan residual compounds in the transformed biological sample is tagged with any suitable detectable label (e.g., a mass label, a radioisotope label, a fluorescent label, a chromophore label, affinity label, an antibody). In some embodiments, the process comprises displaying or recording such a characterization of the population of glycan residual compounds and/or tagged glycan residual compounds.

In some embodiments, the agent described in a therapy herein includes glycan accumulation inhibitors, agents that promote glycan degradation, agents that activate enzymes that degrade glycans, agents that inhibit biosynthesis of glycans, or the like. In some embodiments, the agent that modulates glycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof. Anti-LSD drugs include, by way of non-limiting example, Imiglucerase (Cerazyme), laronidase (Aldurazyme), idursulfase (Elaprase), galsulfase (Naglazyme), agalsidase beta (Fabrazyme), alglucosidase alfa (Myozyme), agalsidase alfa (Replagal), miglustat (Zavesca).

In some embodiments, one or more of the anti-cancer agents are proapoptotic agents. Examples of anti-cancer agents include, by way of non-limiting example: gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol™, also referred to as "paclitaxel", which is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer agents include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In some instances, the detection and/or the quantification of the identity and/or amount of glycan residual compounds present in a biological sample is used to identify and/or diagnose a disorder associated with abnormal degradation, biosynthesis and/or accumulation of glycan in an individual suspected of having such a disorder.

In some instances, the detection and/or the quantification of the identity and/or amount of glycan residual compounds present in the biological sample is used to monitor severity and course of the disease in an individual diagnosed with or suspected of having a disorder associated with the abnormal degradation, biosynthesis and/or accumulation of glycans. In some instances, the detection and/or the quantification of the identity and/or amount of glycan residual compounds present in the biological sample is used to calculate the administered dose of an agent that modulates (e.g., promotes and/or inhibits) glycan biosynthesis and/or degradation.

In certain instances, wherein following administration of a selected dose of a therapeutic agent utilized in a therapeutic method described herein, an individual's condition does not improve, the detection and/or the quantification of the identity and/or amount of glycan residual compounds present in a biological sample provides for a treatment regimen to be modified depending on the severity and course of the disease, disorder or condition, previous therapy, the individual's health status and response to the drugs, and the judgment of the treating physician.

In certain embodiments, monitoring the accumulation of glycans in the individual comprises detecting or quantifying the amount of an glycan residual compounds (or one or more glycan residual compounds) in a sample obtained from the individual (e.g., according to any method described herein) to obtain a first accumulation result (e.g., an initial reading before treatment has begun, or at any other time) and a second accumulation result that is subsequent to obtaining the first result. In some embodiments, the second result is compared to the first result to determine if the treatment is effectively reducing, maintaining, or reducing the rate of increasing the glycan residual compounds levels in a substantially identically obtained sample from the individual being treated. In certain embodiments, depending on the difference between the first and second results, the treatment can be altered, e.g., to increase or decrease the amount of agent administered; to substitute the therapeutic agent with an alternative therapeutic agent; or the like. In certain embodiments, the dose of the therapeutic agent is decreased to a maintenance level (e.g., if the glycan residual compound level has been reduced sufficiently); further monitoring of glycan residual compound levels is optional in such situation, e.g., to ensure that reduced or maintained levels of glycan residual compounds (e.g., monosaccharide(s)) are achieved.

Alternatively, provided herein is a method of detecting response to therapy in an individual or a method of predicting response to therapy in an individual comprising:
  a. administering an agent for treating a disorder associated with the abnormal degradation, biosynthesis and/or accumulation of glycans to a plurality of cells from an individual in need thereof (e.g., a plurality of fibroblasts, serum, plasma, or CSF cells from a human suffering from a disorder associated with the abnormal degradation, biosynthesis and/or accumulation of glycans, such as an LSD or cancer);
  b. monitoring the accumulation of glycans in the plurality of cells using any process described herein for detecting or quantifying the amount of glycan residual compounds (e.g., monosaccharides, sulfate, sialic acid, phosphate, acetate, or the like) present in a lyase digested biological sample from the plurality of cells according to any process described herein.

In specific embodiments, the glycan residual compound(s) detected or measured is one or more monosaccharide. It is to be understood that a plurality of cells from an individual includes cells that are directly taken from the individual, and/or cells that are taken from an individual followed by culturing to expand the population thereof.

EXAMPLES

Example 1

To illustrate the methods described herein, we have used human urine sample from normal patients and patients diagnosed with MPS IIIA. MPS IIIA patients have reduced function of the lysosomal enzyme that de-N-sulfates the nonreducing end glucosamine residues present in heparan sulfate. This unique nonreducing end glycan residual (N-sulfated GlcN) can be liberated by treating the glycans with heparin lyases and quantified by fluorescent detection on HPLC. As shown below, glycans prepared in this manner from normal individuals lack N-sulfate GlcN while MPS IIIA patients have a very high level.

Purification: The biological sample (cells, tissue, blood, serum, or the like) is homogenized and solubilized in 0.1-1.0 N NaOH (e.g., 0.1 N, 0.2 N, 0.3 N, 0.4 N, 0.5 N, 0.6 N, 0.7 N, 0.8 N, 0.9 N, or 1.0 N) or acetic acid and then neutralized with acetic acid or NaOH. Next a small sample is taken to measure protein content of the sample using standard methods. 0.01-0.5 mg/mL (0.01 mg/mL, 0.07 mg/mL, 0.12 mg/mL, 0.17 mg/mL, 0.22 mg/mL, 0.27 mg/mL, 0.32 mg/mL, 0.37 mg/mL, 0.42 mg/mL, or 0.5 mg/mL) protease (trypsin, chymotrypsin, pepsin, pronase, papain, or elastase) is treated in 0.1-0.5 M (e.g., 0.1 M, 0.16 M, 0.23 M, 0.32 M, 0.39 M, 0.44 M, or 0.5 M) NaCl, 0.01-0.1 M (e.g., 0.01 M, 0.02 M, 0.04 M, 0.06 M, 0.08 M, 0.1 M) NaOAc, at pH 5.5-7.5 (e.g., 5.5, 6.0, 6.5, 7.0, or 7.5) and 25-40 C (e.g., 25 C, 30 C, 35 C, or 40 C) for 1-24 hours (e.g., 1 h, 2 h, 4 h, 6 h, 8 h, 12 h, 18 h, 24 h). The sample is diluted to reduce the ionic strength and loaded onto an ion exchange column in 5-100 mM (e.g., 5 mM, 10 mM, 20 mM, 30 mM, 40 mM, 50 mM, 60 mM, 70 mM, 75 mM, 80 mM, 90 mM, 95 mM, 100 mM) NaOAc pH 5-7 with 0-300 mM NaCl. After washing, the bound glycosaminoglycans are eluted with 5-100 mM NaOAc pH 5-7 (e.g., 5, 5.5, 6, 6.5, 7) with 0.8-3 M (e.g., 0.8 M, 1 M, 1.2M, 1.4M, 1.6M, 1.8 M, 2 M, 2.5 M, or 3 M) NaCl. The eluted glycans are then concentrated and desalted by ethanol precipitation, size exclusion, or other methods. The purified glycans are dried for further analysis.

Liberation of non-reducing end residual: The purified glycans are resuspended in 10-300 mM sodium acetate, tris, phosphate, or other suitable buffer, 0.02-1 mM (e.g., 0.02, 0.04, 0.06, 0.08, 0.1, 0.2, 0.3, 0.4, 0.5, 0.6, 0.7, 0.8, 0.9, or 1) calcium acetate, pH 5-8 (e.g., 5, 5.5, 6, 6.5, 7, 7.5, or 8), were digested with heparin lyases I, II, III, I and II, I and III, II and III, or I, II, and III (0.0.15-1.5 milliunits of each in 100-ul reactions, IBEX, Montreal, Canada) at 25 to 37° C. for 1 to 24 hours.

Fluorescent tagging of glycan residual: Dried glycan sample is re-suspended in 2-100 μL 0.003-0.1 M (e.g., 0.003 M, 0.003 M, 0.03 M, 0.06 M, 0.1 M) AB, AA, AMAC, or Bodipy dye and incubated at room temperature for 1-120 minutes (e.g., 1-10 min, 10-15 min, 15-20 min, 20-25 min, 25-30 min, 30-40 min, 40-50 min, 50-60 min, 60-90 min, 90-120 min). Next, the reaction is initiated with 2-100 μL (2 μL, 5 μL, 10 μL, 15 μL, 20 μL, 25 μL, 30 μL, 40 μL, 50 μL, 60 μL, 70 μL, 80 μL, 90 μL, or 100 μL) 1 M NaCNBH$_4$ and the reaction is allowed to proceed at 25-100 C. (e.g., 25 C, 30 C, 35 C, 40 C, 50 C, 60 C, 70 C, 80 C, 90 C, 100 C).

Detection of glycan residual: HPLC separation of tagged saccharides was performed utilizing the following conditions: Column types: 130A BEH particle Phenyl (1.7, 2.5, 3.5, 5, or 10 uM particle size), 130A BEH particle C18 (1.7, 2.5, 3.5, 5, or 10 uM particle size), HSS particle C18 (1.8, 3.5, or 5 uM particle size), or 300A BEH particle C18 (1.7, 3.5, 5, 10 uM particle size) with suitable length and internal diameter.

Buffer Conditions:
A=Ammonium Acetate, Sodium Acetate, or Sodium Chloride (e.g., 0 M, 10 mM, 20 mM, 30 mM, 40 mM, 100 mM, 500 mM, 1 M, 2 M) with 0-20% methanol
B=100% Alcohol, such as methanol, ethanol, or isopropanol
Initial Conditions: 70-95% A, 0-30% B
Flow Rate is constant at 0.05-1 ml/min
Runs a gradient down to 70-90% A, 10-30% B over 5-65 min.
At 8.1 min runs a gradient to 0-20% A, 80-100% B over 5-20 min.
5-65 min returns to initial conditions FIG. 1 illustrates an HPLC trace of eluted compounds detected in normal patient urine not subject to enzymatic glycan residual liberation (i.e., providing background signals). FIG. 2 illustrates an HPLC trace of eluted compounds detected in normal patient urine subject to enzymatic glycan residual liberation as set forth in Example 1. FIG. 3 illustrates an HPLC trace of eluted compounds detected in MPS IIIA patient urine not subject to enzymatic glycan residual liberation (i.e., providing background signals). FIG. 4 illustrates an HPLC trace of eluted compounds detected in MPS IIIA patient urine subject to enzymatic glycan residual liberation.

Example 2

The processes described in Example 1 are repeated and/or modified for the diseases listed in Tables 1-4 utilizing the enzymes described there in and detecting the glycan residual compounds also described therein.

Example 3

NRE Analysis of MPS I, II, VI and VII Cells

Figure 6:
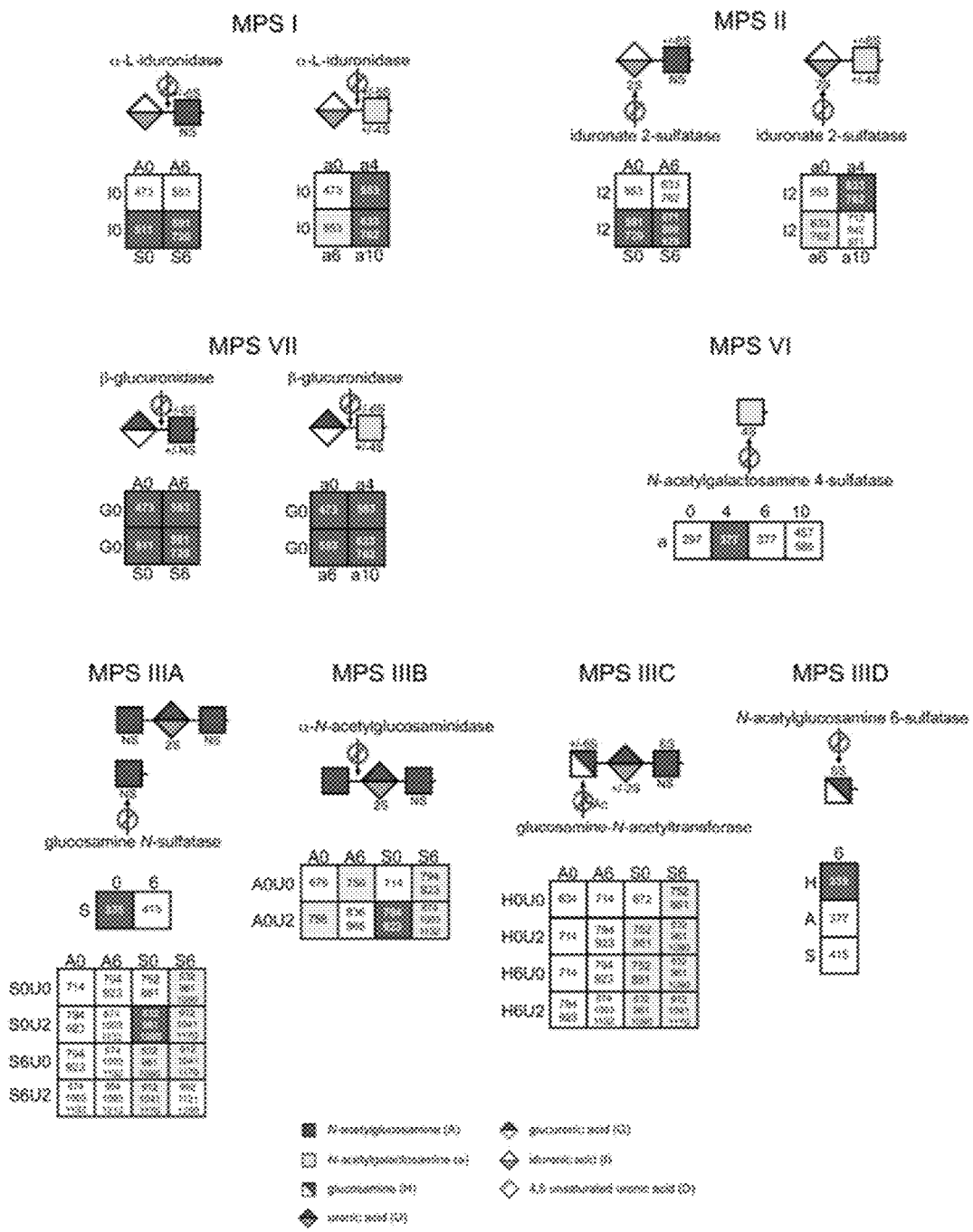
FIG. 6 illustrates MPS Non-reducing end carbohydrates. The defective enzyme for each MPS subclass is displayed along with the liberated NRE carbohydrates characteristic of MPS I, II, IIIA, IIIB, IIIC, IIID, VI and VII using geometric symbols. The matrices show all NRE carbohydrates that are theoretically possible for each MPS subclass using the DSC. The boxes with a black background and whiteface font depict structures that were detected and whose identities were confirmed by their co-chromatography and identical mass spectra as standards, as well as their sensitivity to exoglycosidases or propionic acid anhydride. Suspected structures shown in boxes with a gray background are implied from the liquid chromatography/mass spectra data, i.e. their size and content of sulfate and acetate groups are consistent with the proposed structures. The structures in boxes with a white background are theoretically possible, but have not been observed. The m/z values for both the free molecular ions and adduction ions formed with the ion pairing reagent dibutylamine (DBA) are listed. The single letter designations for the variously modified sugars are described in FIG. 5. The glycan structures are graphically represented by geometric symbols, which are defined in the lower part of the figure
Figure 7:
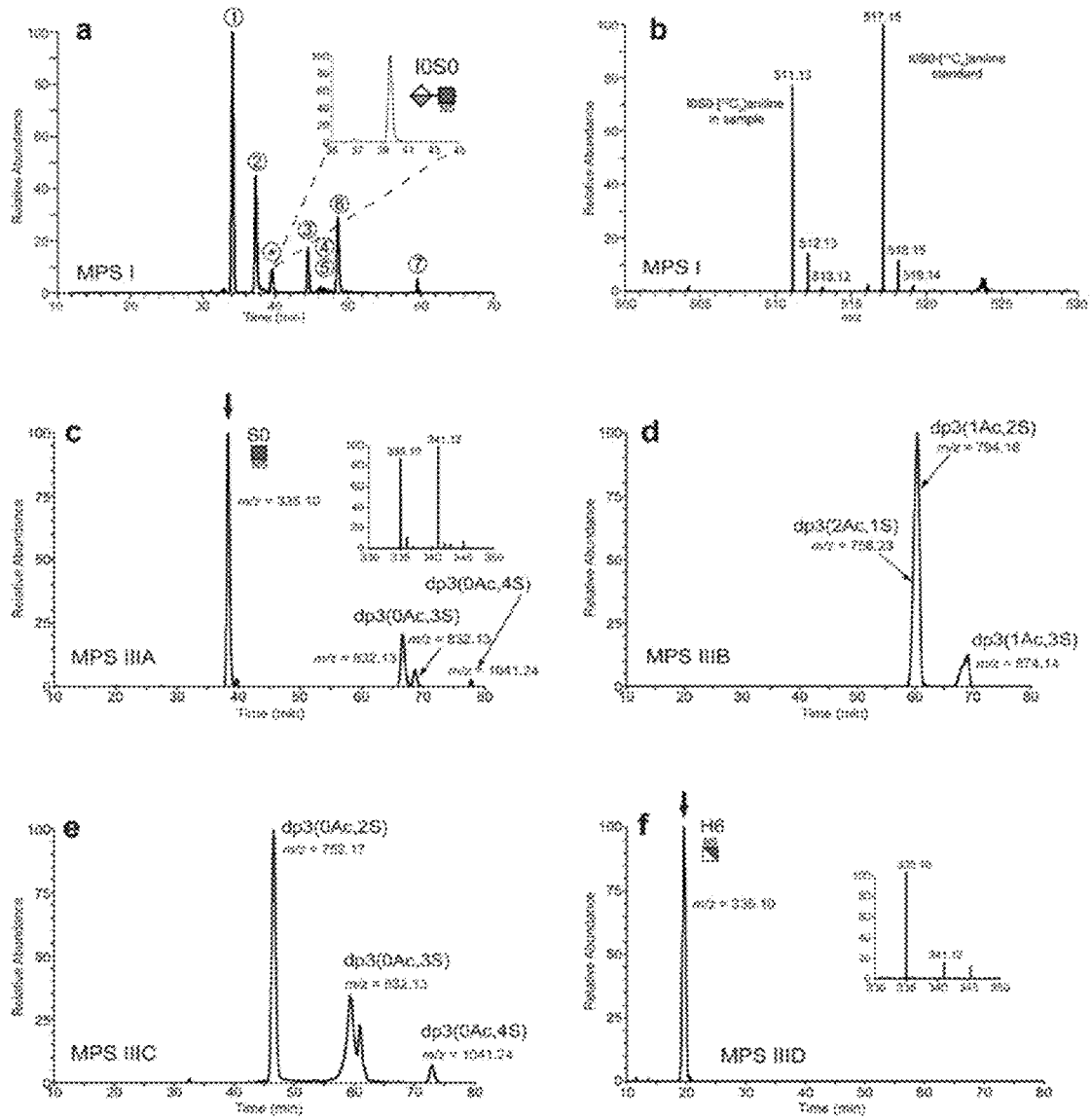
FIG. 7 illustrates analysis of non-reducing ends found in MPS I and Sanfilippo heparan sulfate. (a) Depolymerized heparan sulfate from MPS I fibroblasts (GM01391) was tagged with [12C6]aniline and mixed with standard [13C6] aniline-labeled unsaturated disaccharides and I0S0. The sample was analyzed by LC/MS and the extracted ion current for all known NRE and internal disaccharides was recorded: peak 1, D0A0; peak 2, D0S0; peak 3, D0A6; peak 4, D0S6; peak 5, D2A0; peak 6, D2S0; and peak 7, D2S6. The asterisk marks the [12C6]aniline tagged NRE, which comigrated with [13C6]aniline-labeled I0S0 standard (inset). (b) Mass spectrum for the I0S0 peak shown in panel A. GAGs purified from (c) MPS IIIA (GM00643), (d) MPS IIIB (GM01426), (e) MPS IIIC (GM05157) and (f) MPS IIID (GM17495) fibroblasts were subjected to NRE analysis. For simplicity, only the extracted ion current for m/z values corresponding to monosaccharide and trisaccharide (dp3) NREs are shown for each sample. When the NRE structure was identified by comparison with commercially available standards, the name is indicated in DSC and glycan symbols. The dp3(0Ac,4S) NRE residues in the MPS IIIA and the MPS IIIC samples were detected as adduction ions with the ion pairing reagent ([M−2H+DBA]−1); hence their m/z values were increased by 129 amu (see FIG. 6). The insets in panels c and f show the mass spectra for the monosaccharide biomarkers S0 and H6, respectively, and the corresponding [13C6]aniline tagged standards (arrows in panels c and f).
Figure 10:
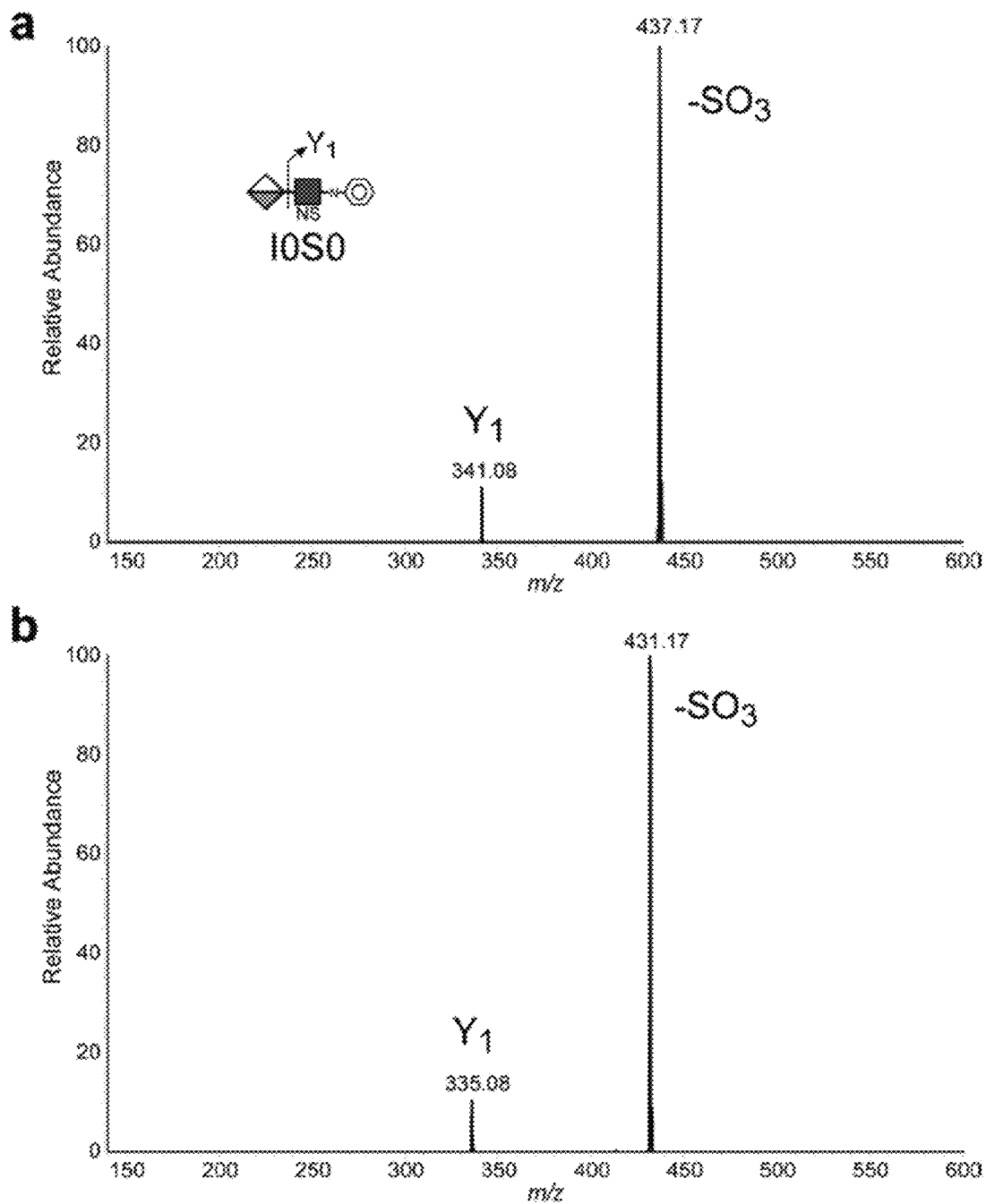
FIG. 10 illustrates a structural comparison of MPS I NRE biomarker with I0S0 standard. Tandem mass spectrometry was carried out on [$^{13}C_6$]aniline-tagged I0S0 standard. The predominant daughter ions and their assignments based on m/z values are indicated in the mass spectrum (a). A schematic representation of the primary inter-ring cleavage of I0S0 is also shown. The m/z values are shown next to each fragment ion. After labeling with [$^{12}C_6$]aniline, the putative I0S0 NRE found in heparan sulfate from cultured fibroblasts from a MPS I patient (GM01391) was also subjected to tandem mass spectrometry (b). The m/z values shown in each CID spectrum are consistent with the difference in mass between [$^{13}C_6$]aniline and [$^{12}C_6$]aniline. Identity between the standard and the MPS I NRE is indicated by the similar CID spectra.
Figure 11:
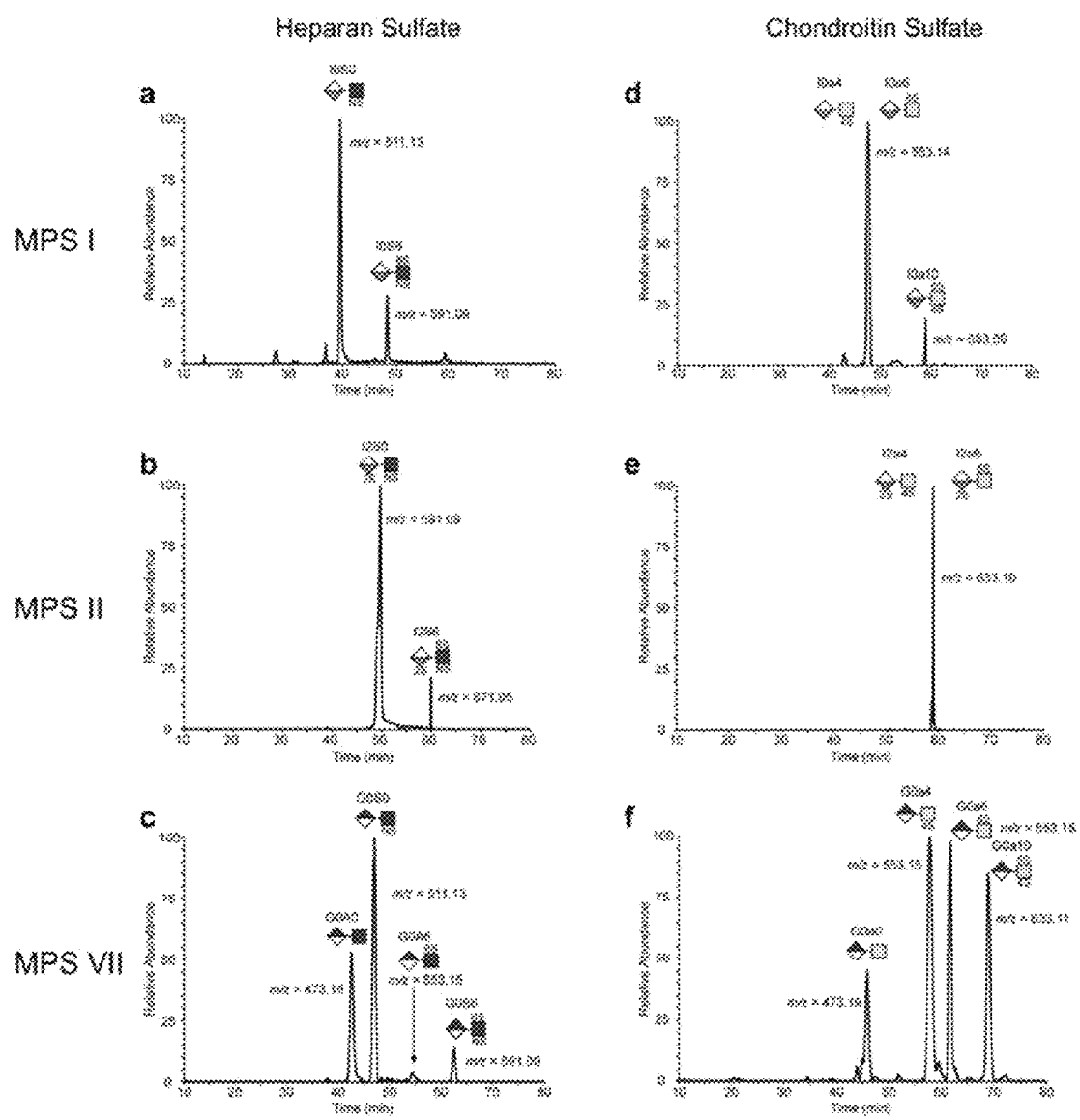
FIG. 11 illustrates analysis of non-reducing end structures found in MPS I, MPS II and MPS VII. GAG samples purified from (a,d) MPS I (GM01391), (b,e) MPS II (GM00615) and (c,f) MPS VII (GM02784) fibroblasts were subjected to enzymatic depolymerization with heparan lyase (a,b,c) or chondroitinase ABC (d,e,f) followed by GRIL-LC/MS analysis. The accumulative extracted ion current for m/z values corresponding to heparan sulfate and chondroitin/dermatan sulfate NRE structures detected in each sample is shown. In the absence of authentic standards, the relative abundance of the individual biomarkers cannot be derived from these spectra due to differences in ionization efficiencies. The identification of the uronic acids is based on chromatographic separation of isobaric species (e.g. G0S0 and G0S6 resolve from I0S0 and I0S6, respectively), differential sensitivity to α-L-iduronidase, and inference based on the nature of the enzyme deficiency in the cells. Putative structures are indicated by both DSC and glycan symbols as well as their m/z values. In cases where two isobaric species could not be discriminated by CID analysis (I0a4/I0a6 in panel d and I2a4/I2a6 in panel e), both species are shown.
Figure 12:
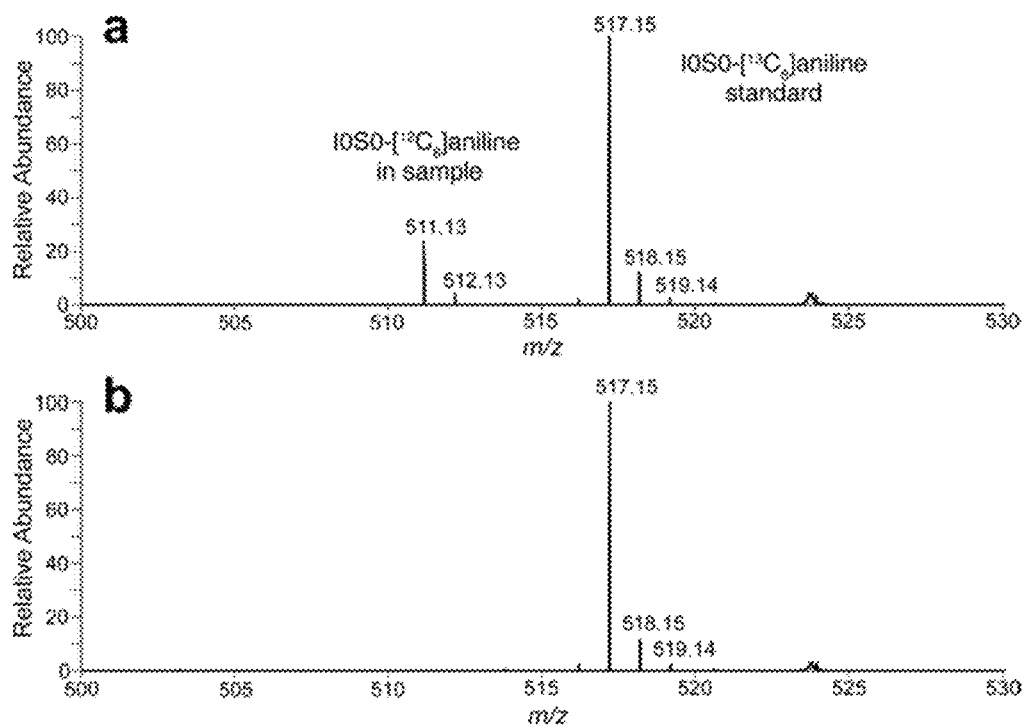
FIG. 12 illustrates removal of the non-reducing end biomarker in MPS I by α-iduronidase treatment. An equal amount of heparan sulfate isolated from fibroblasts of a patient with MPS I (GM01391) was treated with recombinant α-iduronidase or with BSA. The samples were then tagged with [$^{12}C_6$]aniline, mixed with 10 pmole of [$^{13}C_6$] aniline-labeled I0S0 standard, and analyzed by GRIL-LC/MS. The mass spectrum for the BSA-treated samples shows the MPS I NRE and the I0S0 standard (a). The mass spectrum of the iduronidase-treated sample shows the loss of the MPS I biomarker (b). The m/z values for all species detected are indicated above the major peaks.

To demonstrate the potential utility of this approach, dermal fibroblasts from human MPS I patients (α-iduronidase [IDUA] deficiency) and from normal human donors were grown. Cells were expanded and kept in culture up to 8 weeks to allow for significant lysosomal accumulation. GAGs remaining in the cell layer were extracted and subjected to enzymatic depolymerization followed by reductive amination with [$^{12}$C$_6$]aniline. Samples were mixed with 10 pmoles of each [$^{13}$C$_6$]aniline unsaturated disaccharide standard and [$^{13}$C$_6$]aniline-tagged I0S0 that was synthesized. All possible candidate structures were searched for (FIG. 6) and the extracted ion chromatogram shown in FIG. 7a. Peaks 1-7 comigrated with known unsaturated disaccharides and had the expected m/z values. The MPS I sample had an additional peak marked by an asterisk that was not present in the normal fibroblast sample. This peak had the same elution position as the aniline-tagged I0S0 standard (expanded inset in FIG. 7a). The mass spectrum for this peak gave an m/z=511.1 and isotopic cluster consistent with the proposed structure I0S0, and a corresponding m/z=517.1 and isotopic cluster expected for the [$^{13}$C$_6$]aniline tagged standard (FIG. 7b). Further verification was carried out by collision-induced dissociation (CID), which demonstrated structural identity with the I0S0 standard (FIG. 10). Digestion of heparan sulfate from cells derived from MPS I patients also yielded a disaccharide of m/z=591.1 (FIG. 11a), consistent with the structure I0S6. This material comigrated with the internal disaccharide D250 and thus was contained within peak 6 in the chromatogram shown in FIG. 7a. However, it was easily discriminated from D250 by the mass detector given the 18 amu difference. Pretreatment of an MPS I sample with α-L-iduronidase led to the loss of the native NRE structures confirming their identity (FIG. 12). Fibroblasts from three different MPS I patients exhibited NRE species identified as I0S0 and I0S6. These entities were not observed in samples prepared from normal human fibroblasts.

Figure 13:
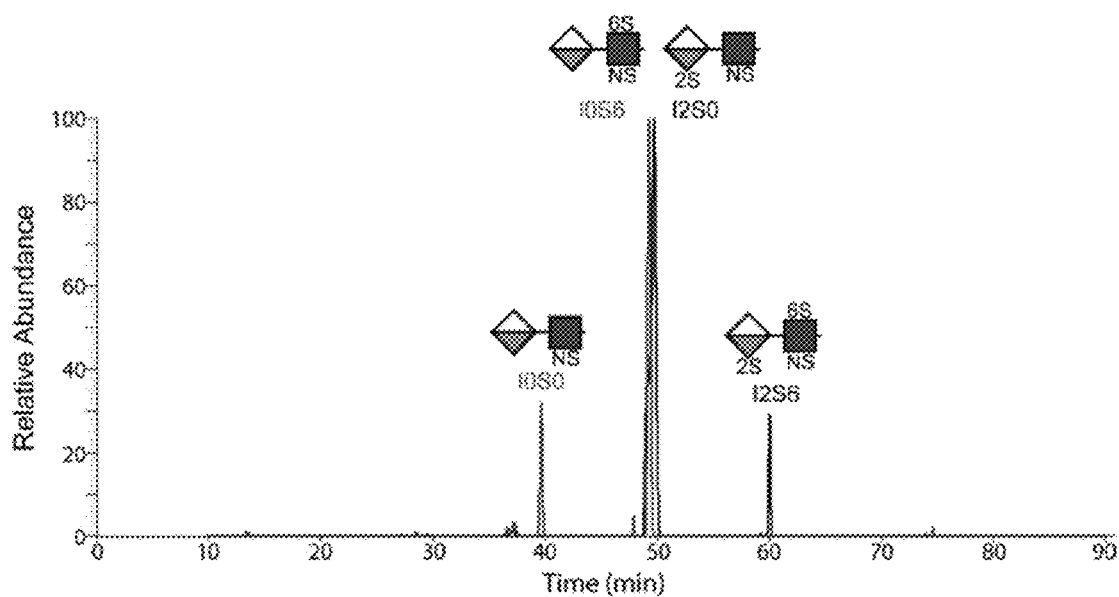
FIG. 13 illustrates removal of the non-reducing end biomarker found in MPS II by Iduronate-2-sulfatase. Equal amounts of heparan sulfate isolated from fibroblasts from an MPS II patient (GM00615) were treated with either BSA or recombinant iduronate-2-sulfatase prior to NRE analysis. The accumulative extracted ion current for m/z values corresponding to 2-O-sulfated and non-2-O-sulfated NRE species for the BSA-treated sample (black trace) and the iduronate-2-sulfatase-treated sample (red trace) are shown in the chromatogram. The NRE structures consistent with the m/z values for the species detected after each treatment are shown.

MPS II (idurono-2-sulfatase [IDS] deficiency) and MPS VII (β-D-glucuronidase [GLCA] deficiency) also affect heparan sulfate degradation due to defects in processing the non-reducing terminal uronic acid (desulfation of iduronate-2-sulfate and removal of glucuronic acid, respectively). Saturated NRE disaccharides were detected after digestion of GAGs derived from fibroblasts of MPS II and MPS VII patients (FIG. 6 and FIGS. 11b and 11c). The mass spectra for the MPS II NREs and their elution positions were consistent with the expected disaccharide biomarkers I2S0 and I2S6. Analysis of MPS VII heparan sulfate was more complex, yielding four disaccharides tentatively identified as G0A0, G0A6, G0S0 and G0S6. Treatment of the MPS II samples with recombinant IDS converted the NRE to those found in MPS I (I0S0 and I0S6, respectively; FIG. 13).

MPS I, MPS II, and MPS VII also affect the degradation of chondroitin sulfate and dermatan sulfate. Analysis of these GAGs using chondroitinase ABC yielded a set of NRE disaccharides diagnostic for each disorder (FIG. 6). MPS I yielded the monosulfated NRE disaccharides I0a4 and I0a6 in addition to the disulfated disaccharide I0a10 (FIG. 11d). MPS II yielded I2a4 and I2a6 (FIG. 11e) and MPS VII yielded G0a0, G0a4, G0a6 and G0a10 (FIG. 11f).

Figure 14:
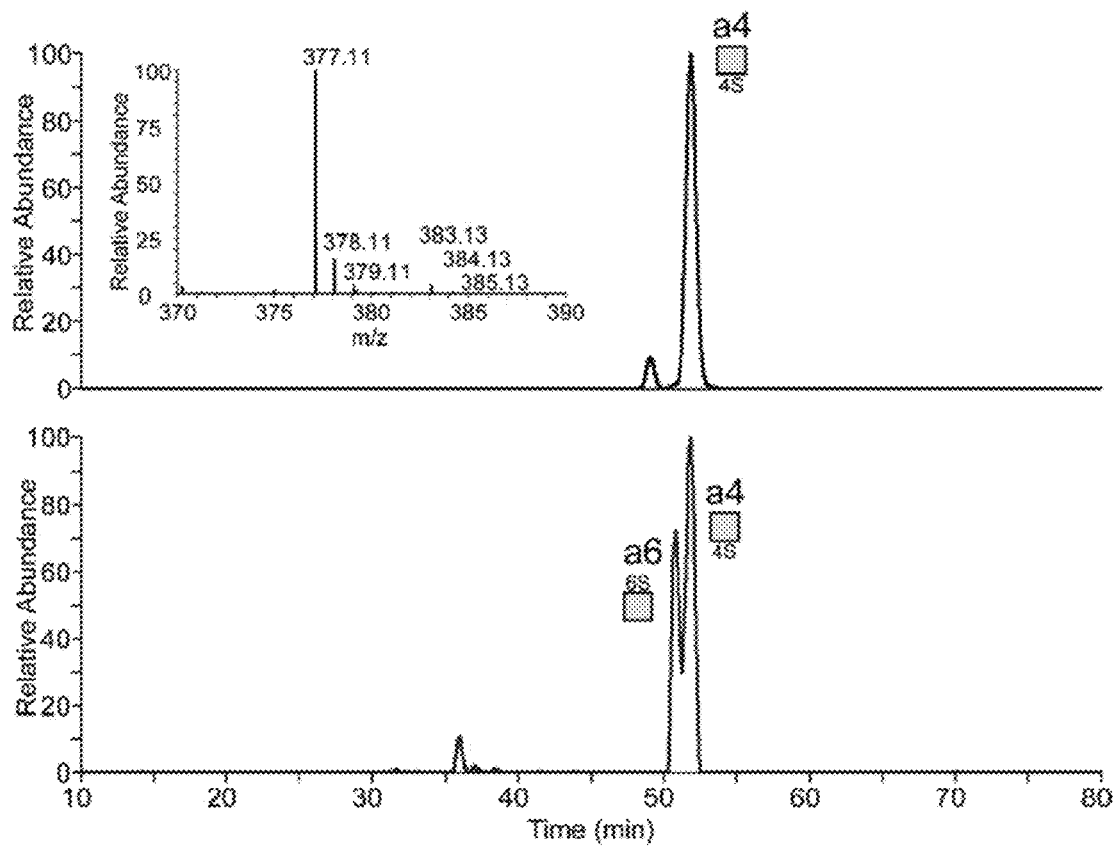
FIG. 14 illustrates GRIL-LC/MS analysis of MPS VI chondroitin sulfate NRE. GAG purified from MPS VI (GM00519) fibroblasts was enzymatically depolymerized with chondroitinase ABC followed by GRIL-LC/MS analysis. The accumulative extracted ion current for m/z values corresponding to NRE monosaccharide structures GalNAc6S (a6) and GalNAc4S (a4) standards labeled with [$^{13}C_6$] aniline are shown (bottom red trace) and the endogenous a4 labeled with [$^{12}C_6$] aniline detected in the MPS VI sample is shown (top black trace). The mass spectrum are indicated for the a4 peak in the top trace is shown in the inset with the m/z values for the isotopic clusters for the endogenous [$^{12}C_6$]aniline-tagged a4 (m/z=377.11) and the [$^{13}C_6$] aniline-labeled a4 standard (m/z=383.13).

Analysis of chondroitin sulfate and dermatan sulfate from MPS VI (N-acetylgalactosamine 4-sulfatase [G4S] deficiency) demonstrated accumulation of N-acetylgalactosamine-4-sulfate (a4, FIG. 6), which co-migrated with an aniline tagged a4 standard (FIG. 14). Note that a4 resolves partially by liquid chromatographically from 6-sulfo-N-acetylgalactosamine (a6) (lower panel). However, the biological sample yielded predominantly a4, consistent with the deficiency in the N-acetylgalactosamine 4-sulfatase in these cells. No trisaccharides species were detected.

Example 4

NRE Analysis of MPS III Cells

The Sanfilippo family of MPS disorders was analyzed using the same approach as above: MPS IIIA (sulfamidase

[SGSH] deficiency), MPS IIIB (α-N-acetylglucosaminidase [NAGLU] deficiency), MPS IIIC (N-acetyltransferase [HGSNAT] deficiency) and MPS IIID (glucosamine-6-sulfatase [GNS] deficiency). These disorders only affect lysosomal degradation of heparan sulfate and have in common deficiencies in the enzymes that process the NRE glucosamine residue. Because heparin lyases cleave linkages between a glucosamine unit and a uronic acid, it was expected that analysis of Sanfilippo heparan sulfate should yield diagnostic monosaccharides (glucosamine derivatives) or trisaccharides (glucosamine–uronic acid–glucosamine derivatives) from the NRE as opposed to the disaccharides observed in MPS I, II and VII.

Figure 15:
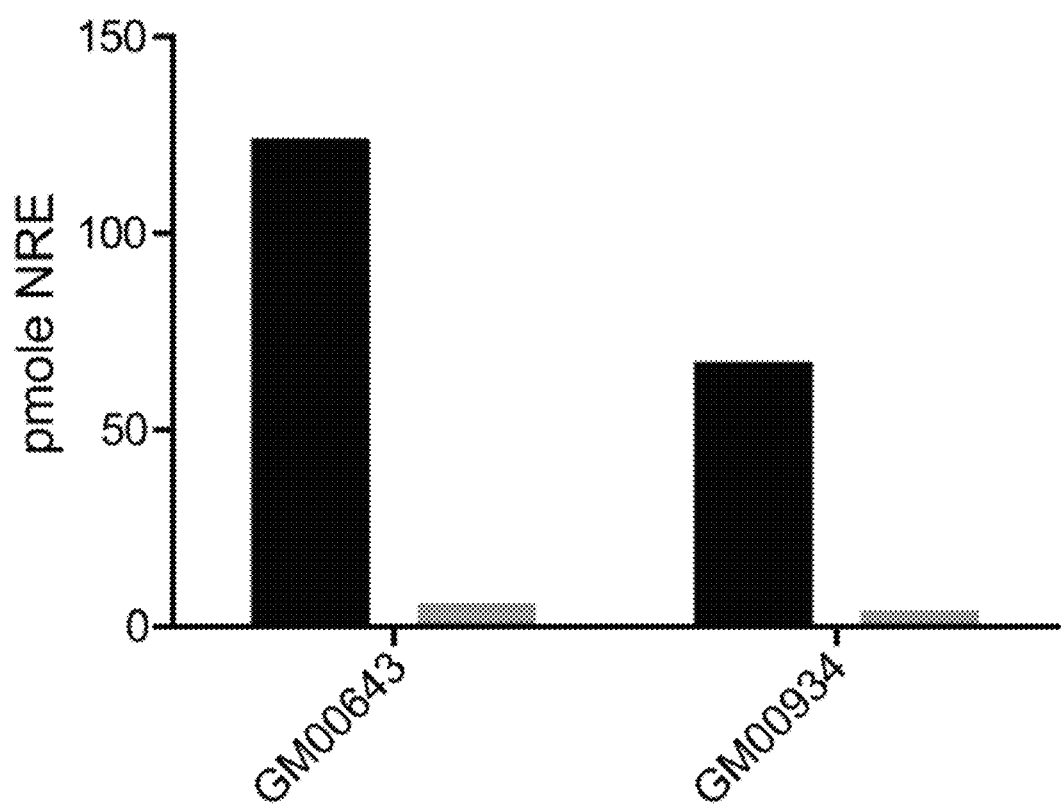
FIG. 15 illustrates removal of the non-reducing end biomarker in MPS IIIA by sulfamidase. Heparan sulfate purified from fibroblasts from two MPS IIIA patients (GM00643 and GM00934) was treated with either BSA (black bars) or sulfamidase (light grey bars) prior to GRIL-LC/MS analysis. [$^{13}C_6$]aniline-labeled S0 standard (10 pmol) was added to each sample and used to calculate the recovery of S0.
Figure 16:
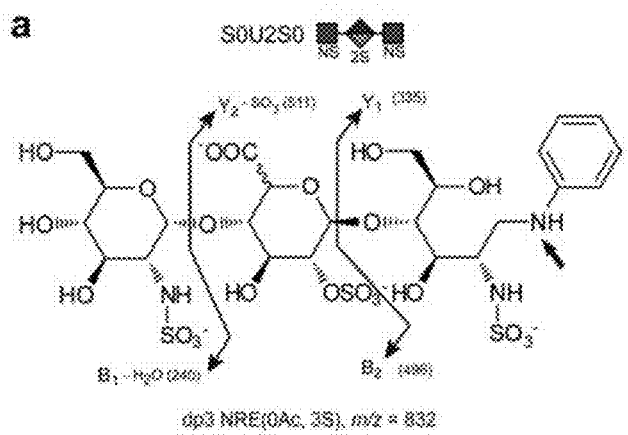
FIG. 16 illustrates CID analysis of NRE trisaccharides found in Sanfilippo sub-classes. Representative trisaccharide NRE structures detected in heparan sulfate from fibroblasts of MPS IIIA, MPS IIIB and MPS IIIC patients were subjected to collision induced dissociation. The most likely structures are indicated along with the product ions detected. The structural parameters for each parent ion are displayed below each structure. To confirm the presence of an unsubstituted glucosamine residue in the MPS IIIC trisaccharides, aniline-labeled samples were acylated with propionic anhydride (PA), which reacts with both primary and secondary amines. The solid arrows point out primary and secondary amines susceptible to acylation by propionic anhydride. All of the MPS IIIC trisaccharides gained mass consistent with the addition of two propionyl groups. In contrast, the MPS IIIA and IIB trisaccharides picked up a single propionyl group due to proprionylation at the bridging secondary amine derived from reductive amination with aniline. Thus, the addition of a second proprionate group to MPS IIIC trisaccharides is consistent with their containing an unsubstituted glucosamine unit. Due to the detection of only two product ions for the MPS IIIC NRE trisaccharide, two potential structures are possible.
Figure 16:
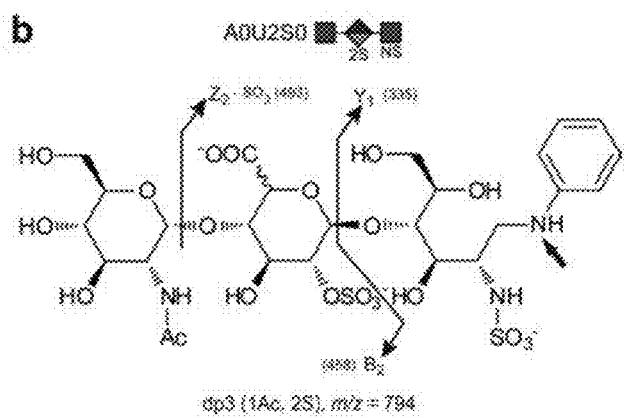
Figure 16:
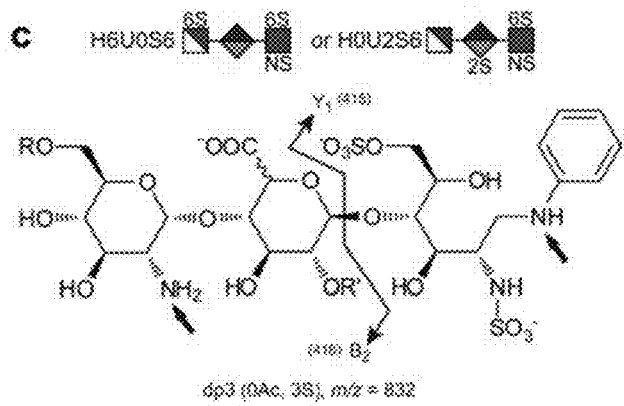

Analysis of MPS IIIA samples showed the typical unsaturated disaccharides generated from internal segments of the chains and a unique peak at 38.5 minutes not present in control or other MPS samples. This material had the characteristic mass spectrum expected for [$^{12}C_6$]aniline-tagged N-sulfoglucosamine (S0, m/z=335.1) and comigrated with an authentic [$^{13}C_6$]aniline-tagged standard (m/z=341.1; FIG. 7c, inset). Treatment of two different MPS IIIA samples with sulfamidase prior to heparinase depolymerization destroyed the S0 biomarker, consistent with its proposed identity (FIG. 15). Digestion of MPS IIIA heparan sulfate also yielded trisaccharides that varied in the number of acetate and sulfate groups (FIG. 7c, dp3). The most prominent species dp3(0Ac,3S) was analyzed by CID and gave a fragmentation pattern consistent with S0U2S0 (FIG. 16a). Although the uronic acid could be glucuronic acid, iduronic acid predominates in segments of the chain containing repeating N-sulfoglucosamine units.

Analysis of MPS IIIB samples yielded three NRE trisaccharides, with m/z values consistent with the presence of 1-2 acetate groups and 1-3 sulfates (FIG. 7d). Since MPS IIIB is characterized by the lack of α-N-acetylglucosaminidase, the terminal sugar should be N-acetylglucosamine, which was confirmed by CID analysis of the predominant trisaccharide (m/z=794) identified as A0U2S0 (FIG. 16b). Similarly, the NREs from MPS IIIC were predicted to contain a free unsubstituted amine due to the deficiency of glucosamine N-acetyltransferase. Four trisaccharides were detected, all lacking acetate groups (FIG. 7e). CID analysis of dp3(0Ac, 3S) and derivatization with propionyl anhydride suggested structures consistent with H6U0S6 or H0U2S6 (FIG. 16c).

MPS IIID cells lack the 6-sulfatase that can remove the 6-O-sulfate group from terminal N-acetylglucosamine units. NRE analysis of MPS IIID heparan sulfate detected a single monosaccharide species with m/z value of 335 corresponding to N-unsubstituted GlcNH$_2$6S (H6) (FIG. 7f). While H6 is isobaric with S0 found in MPS IIIA, its retention time was significantly less due to the presence of the unsubstituted amine and consequently these markers were easily discriminated. Furthermore, H6 in MPS IIID co-eluted with [$^{13}C_6$] aniline-labeled standard H6 verifying its identity (FIG. 7f, inset). No N-acetylglucosamine-6-sulfate was detected, nor were any trisaccharide NRE species bearing a non-reducing terminal 6-O-sulfated N-acetylglucosamine unit (FIG. 7f).

Example 5

Use of NRE Biomarkers

Figure 8:
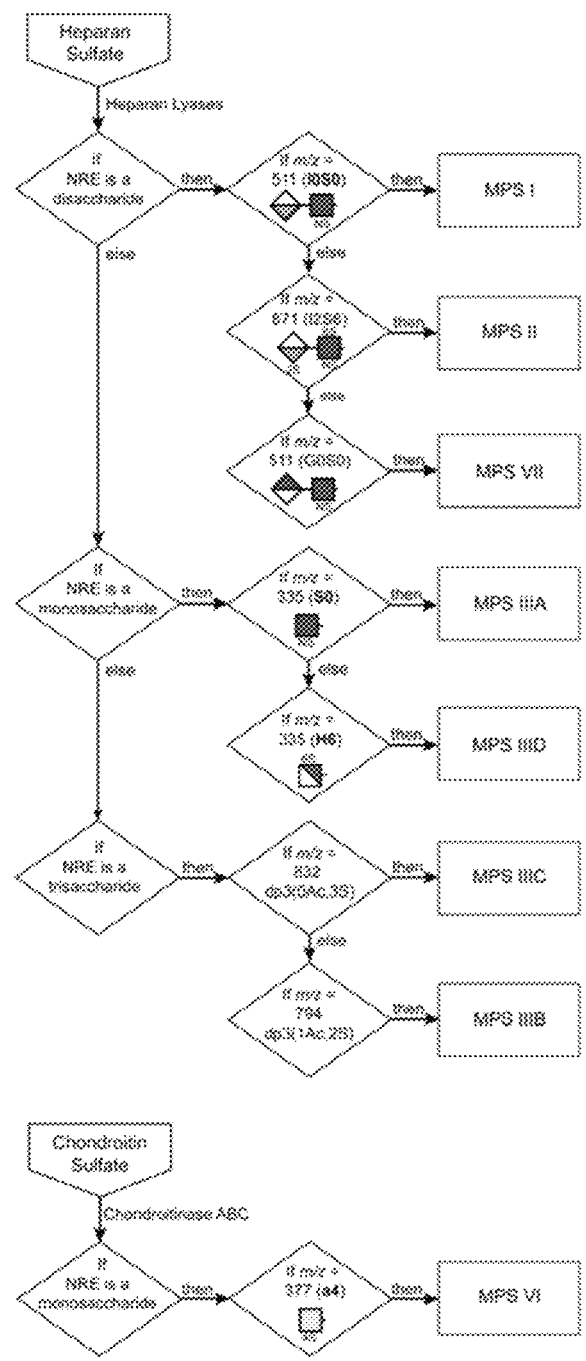
FIG. 8 illustrates systematic diagnostic screening of GAG samples for various MPS disorders. Shown is a flow chart for MPS discovery based on the detection of diagnostic non-reducing end glycans present in GAG samples extracted from patient or animal model sources. The detection criteria are based on NRE size (monosaccharide, disaccharide and trisaccharide), m/z value, and structural features (number of acetates (Ac) or sulfates (S)). For a complete unknown, portions of the sample are analyzed in parallel for heparan sulfate and chondroitin/dermatan sulfate NREs.

Although most MPS GAG samples yielded multiple NRE carbohydrates (FIG. 6), it was possible to select single unique NREs as biomarkers for each MPS disorder and then combine them into a decision tree based on size of NRE structures (mono-, di- and trisaccharides), degree of sulfation, and retention time during liquid chromatography (FIG. 8). The diagnostic decision tree becomes even more robust by inclusion of other carbohydrate biomarkers (FIG. 6), but the specific NREs indicated in FIG. 8 are sufficient to diagnose the eight MPS disorders. To determine the potential utility of these markers for diagnosis, nine different human urine samples from normal control subjects and patients suffering from various Sanfilippo disorders were screened as well as two canine urine samples (one normal and one with MPS I) and liver, brain and kidney GAGs from MPS IIIB mice. Using the scheme outlined in FIG. 8 all samples were correctly diagnosed (Table 16).

Table 16. Analysis of GAG samples purified from mouse tissues and human and canine urine. GAG was extracted and analyzed for MPS diagnostic biomarkers using the scheme shown in FIG. 8. Diagnostic markers: MPS I, I0S0; MPS II, I2S6; MPS IIIA, S0 and S0U2S0; MPS IIIB, A0U2S0; MPS IIIC dp3(0Ac,3SO$_4$), a trisaccharide containing no acetate groups and three sulfate groups; MPS IIID, H6; MPS VI, a4; MPS VII, G0S0.

TABLE 16

| Sample | Sample Identity | NRE Biomarkers Detected | Sensi-Pro Analysis |
|---|---|---|---|
| Liver, Mouse-1 | Unaffected, MPS IIIB Carrier (Het) | Trace | Normal |
| Liver, Mouse-2 | MPS IIIB | A0U2S0 | MPSIIIB |
| Brain, Mouse-1 | Unaffected, MPS IIIB Carrier (Het) | Trace | Normal |
| Brain, Mouse-2 | MPS IIIB | A0U2S0 | MPSIIIB |
| Kidney, Mouse-1 | MPS IIIB | A0U2S0 | MPSIIIB |
| Urine, Human-1 | Normal | Trace | Normal |
| Urine, Human-2 | Normal | Trace | Normal |
| Urine, Human-3 | Normal | Trace | Normal |
| Urine, Human-4 | Normal | Trace | Normal |
| Urine, Human-5 | MPS IIIC | dp3(0Ac, 3S0$_4$) | MPSIIIC |
| Urine, Human-6 | MPS IIIC | dp3(0Ac, 3S0$_4$) | MPSIIIC |
| Urine, Human-7 | MPS IIIC | dp3(0Ac, 3S0$_4$) | MPSIIIC |
| Urine, Human-8 | MPS IIIA | S0, S0U2S0 | MPSIIIA |
| Urine, Human-9 | MPS IIIB | A0U2S0 | MPSIIIB |
| Urine, Canine-1 | Unaffected, MPS I Carrier (Het) | Trace | Normal |
| Urine, Canine-2 | MPS I | I0S0 | MPS I |

Analysis of multiple MPS IIIA cell lines showed striking accumulation of the S0 biomarker, which corresponded well with the level of heparan sulfate storage (Table 17). Normal fibroblasts yielded minute amounts of S0. In general, samples from normal cells, tissues and urine exhibited less than 1% of the amount of NRE biomarkers observed in samples from affected patients or animals.

TABLE 17

Quantitation of markers in MPS IIIA cells and normal fibroblasts

| Cell line | Enzyme activity (Units/mg) | Heparan Sulfate (nmol/mg cell protein) | MPS IIIA marker: S0 (pmol/mg cell protein) |
|---|---|---|---|
| Normal | 9 ± 0.7 | 0.59 ± 0.22 | 2 ± 2 |
| GM00629 | 0.49 ± 0.12 | 33.6 | 670 |
| GM00643 | 0.45 ± 0.08 | 28.4 | 720 |
| GM00879 | 0.62 ± 0.02 | 17.3 | 490 |
| GM00934 | 0.46 ± 0.07 | 16.6 | 470 |
| GM06110 | 0.55 ± 0.36 | 6.8 | 220 |

Five normal fibroblasts were analyzed (CRL-1634 (human foreskin fibroblasts), GM00200 (clinically unaffected sibling of metachromatic leukodystrophy patient), GM05659, GM08398, and GM15871 (clinically unaffected sibling of an Ehlers-Danlos patient). The average values±standard deviation are provided. The values for the various MPS IIIA lines represent duplicate analyses for enzyme activity and single determinations for heparan sulfate storage and the S0 biomarker.

Figure 9:
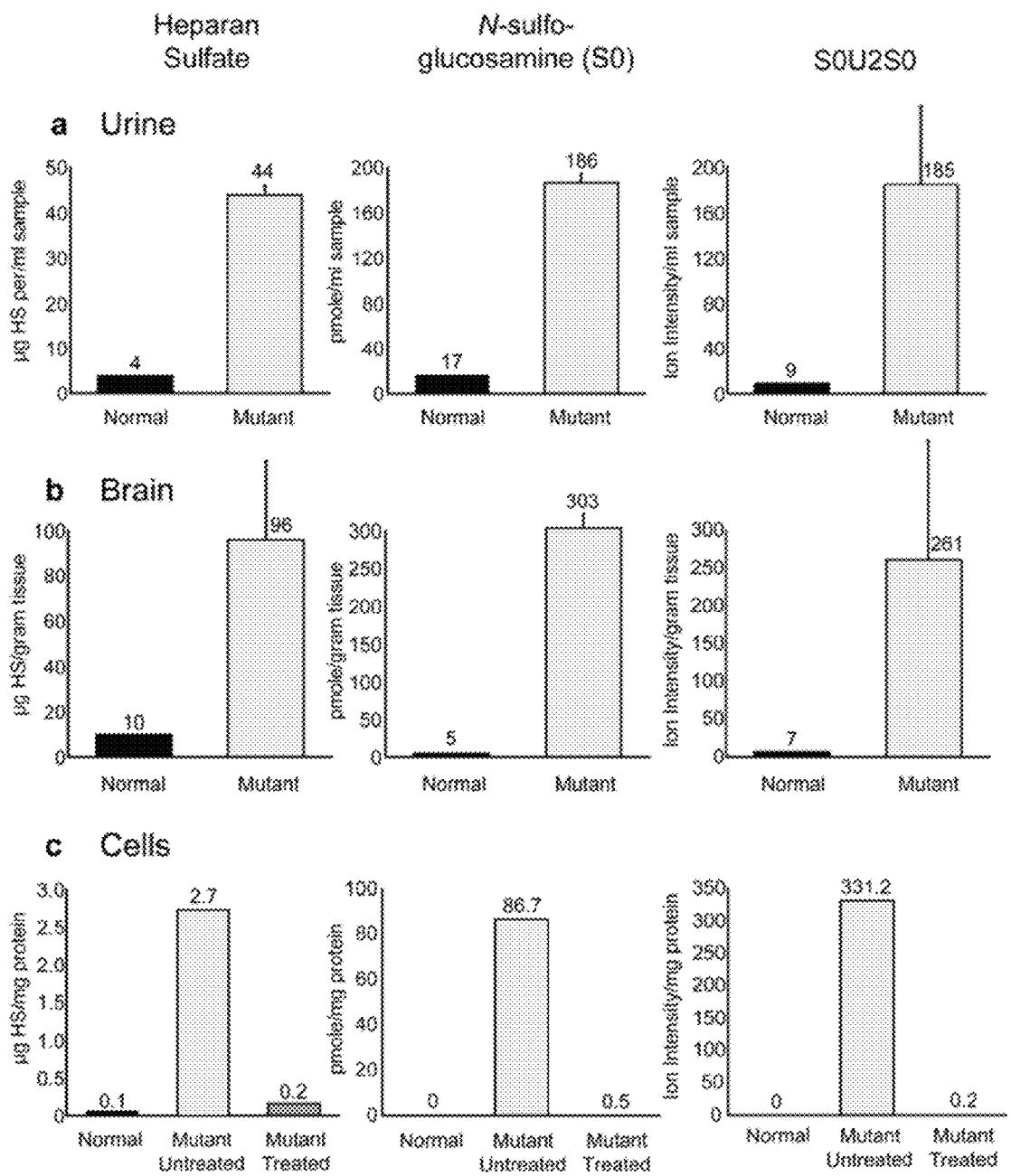
FIG. 9 illustrates a comparison of total heparan sulfate to N-sulfoglucosamine (S0) in MPS IIIA samples. (a) Heparan sulfate from normal (black bars) and MPS IIIA (light grey bars) urine was analyzed. The individual disaccharides and NRE N-sulfoglucosamine (S0) was quantitated relative to standards. Since trisaccharide standards are not available, the values of the extracted ion current for S0U2S0 are shown. (b) Analysis of normal (black bars) and MPS IIIA (light grey bars) brain heparan sulfate as in panel A. (c) MPS IIIA cells underwent enzyme replacement by incubation with 0.06 mU/ml of sulfamidase for 48 hours prior to GAG extraction and subsequent analysis. The amount of heparan sulfate (black bars), the monosaccharide biomarker S0 (light grey bars), and the trisaccharide biomarker S0U2S0 (dark grey bars) were measured and compared to samples from cells without enzyme supplementation. The bars represent the average±standard deviation, n=3.

The detection of lysosomal storage based on GAG content in the brain and urine has been challenging due to various methods used for detection and quantitation, in particular indirect techniques based on dye binding or displacement. Urine and brain samples from MPS IIIA (Sgsh$^{-/-}$) and wildtype mice and MPS IIIA human fibroblasts were analyzed using the scheme described in FIG. 8. Using this method, total heparan sulfate and the biomarker S0 showed a 12-fold accumulation in MPS IIIA urine samples compared to the wildtype (FIG. 9a). The trisaccharide biomarker S0U2S0 was readily detectable in the Sgsh$^{-/-}$ urine, but virtually undetectable in wildtype urine. In brain samples the heparan sulfate level was elevated 12-fold, whereas the biomarker S0 increased 60-fold compared to the wildtype (FIG. 9b). The trisaccharide marker was essentially present only in the Sgsh$^{-/-}$ sample.

In order to test whether the NRE structures afford a more precise and sensitive assay to monitor therapeutic enzyme replacement, cultures of MPS IIIA human fibroblasts were supplemented with recombinant sulfamidase for 48 hours prior to GAG extraction and analysis. Enzyme replacement led to a significant drop in heparan sulfate and both the biomarkers, S0 and S0U2S0 (FIG. 9c). Thus, the NRE biomarkers, in particular the trisaccharides, are useful for monitoring the therapeutic efficacy of intervention strategies.

Example 6

Synthesis of I0S0

All moisture sensitive reactions were performed under an argon atmosphere by using vacuum dried glassware. All commercial materials were used without purification, unless otherwise noted. CH$_2$Cl$_2$ was freshly distilled from calcium hydride under nitrogen prior to use. Toluene, DMF, diethylether, methanol and THF were purchased anhydrous and used without further purification. Molecular sieves (4 Å) were flame activated in vacuo prior to use. All reactions were performed at room temperature unless specified otherwise. TLC analysis was conducted on Silica gel 60 F254 (EMD Chemicals Inc.) with detection by UV-absorption (254 nm) when applicable, and by spraying with 20% sulfuric acid in ethanol followed by charring at ~150° C. or by spraying with a solution of (NH$_4$)$_6$Mo$_7$O$_{24}$ H$_2$O (25 g/L) in 10% sulfuric acid in ethanol followed by charring at ~150° C. Column chromatography was performed on silica gel G60 (Silicycle, 60-200 μm, 60 Å) or on Bondapak C-18 (Waters). $^1$H and $^{13}$C NMR spectra were recorded on Varian inova-300 (300/75 MHz), inova-500 (500/125 MHz) and inova-600 (600/150 MHz) spectrometers equipped with sun workstations. Chemical shifts are reported in parts per million (ppm) relative to tetramethylsilane (TMS) as the internal standard. NMR data is presented as follows: Chemical shift, multiplicity (s=singlet, d=doublet, t=triplet, dd=doublet of doublet, m=multiplet and/or multiple resonances), coupling constant in Hertz (Hz), integration. All NMR signals were assigned on the basis of $^1$H NMR, $^{13}$C NMR, COSY and HSQC experiments. Mass spectra were recorded on an Applied Biosystems 5800 MALDI-TOF proteomics analyzer. The matrix used was 2,5-dihydroxybenzoic acid (DHB) and Ultramark 1621 as the internal standard.

The synthesis of β-D-idopyranosyluronate)-(1→4)-(2-N-sulfoamino-2-deoxy-α/β-D-glucopyranoside) (7) (I0S0) is described below:

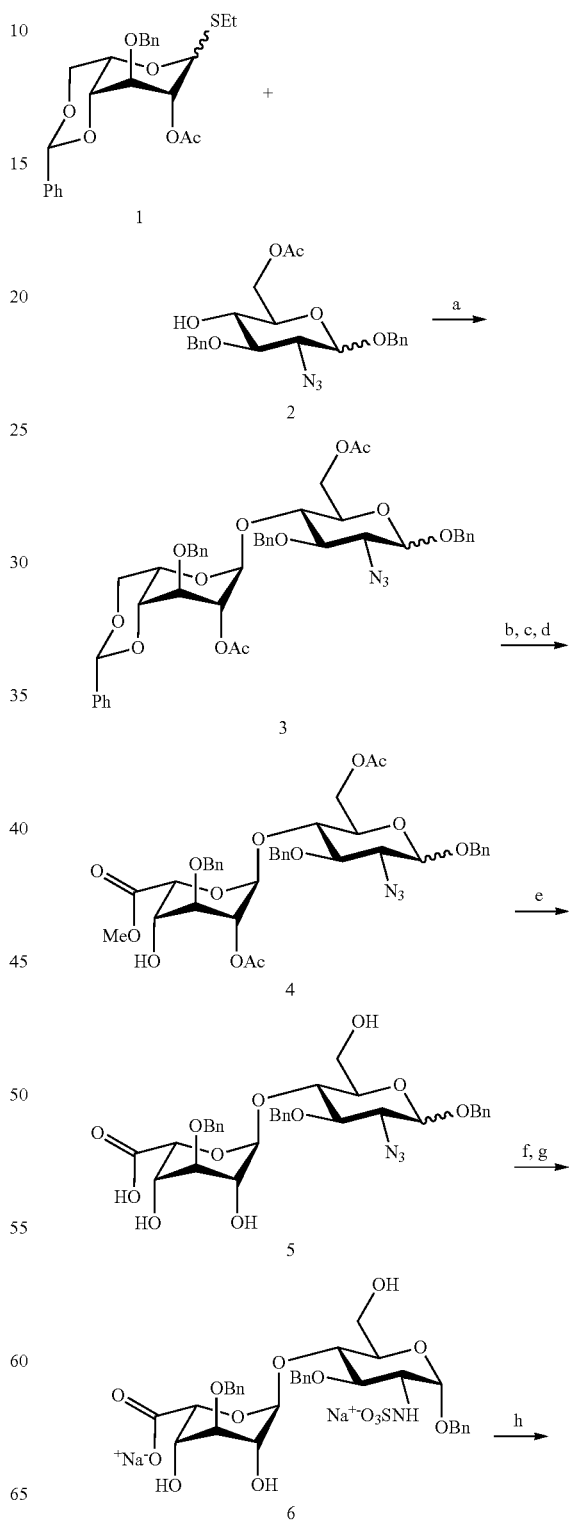

-continued

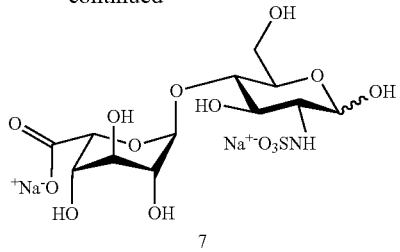

7 a) NIS, TMSOTf, 0° C., DCM, 73%; b) EtSH, p-TsOH, 96%; c) TEMPO, BAIB, DCM, $H_2O$, 1 h; d) $CH_2N_2$, THF (2 steps, 83%); e) LiOH 0.22 M, THF, 99%; f) $PMe_3$, NaOH, THF; g) $Et_3N$, $SO_3Py$, NaOH, (2 steps, 66%); h) $Pd(OH)_2/C$, $H_2$, 83%.

Benzyl (2-O-acetyl-3-O-benzyl-4,6-O-benzylidene-β-D-glucopyranosyl)-(1→4)-6-O-acetyl-2-azido-3-O-benzyl-2-deoxy-α/β-D-glucopyranoside (3): Glycosyl donor 1 (467 mg, 1.05 mmol) and glycosyl acceptor 2 (877 mg, 0.375 mmol) were combined in a flask, co-evaporated with toluene (3×3 mL), and dissolved in DCM (8.7 mL). Powdered freshly activated 4 Å molecular sieves were added, and the mixture was stirred for 30 min at ambient temperature. The reaction mixture was cooled (0° C.) and NIS (0.236 g, 1.052 mmol) and TMSOTf (19.08 μL, 0.105 mmol) were added and the stirring was continued until TLC indicated the consumption of donor (~10 min). The mixture was then quenched with aqueous $Na_2S_2O_3$ and extracted with DCM (2×10 mL). The combined organic layers were dried ($MgSO_4$) and filtered and the filtrate was concentrated in vacuo. The residue was purified by silica gel chromatography using stepwise gradient of toluene and EtOAc (100-80%) to give disaccharide 3 (658 mg, 73%). $^1$H NMR (500 MHz, $CDCl_3$): δ 7.44-7.25 (m, 30H, CH Aromatic), 5.28 (s, 2H, CH benzylidene×2), 5.00-4.96 (m, 4H, H2, H'1, H1α, H'2 CHH Bn), 4.92 (d, 1H, J=11.5 Hz, CHH Bn), 4.84 (d, 1H, J=11.0 Hz, CHH Bn), 4.80 (d, 1H, J=11.0 Hz, CHH Bn), 4.76-4.55 (m, 10H, CHH Bn×4, CHH Bn×2, CHH Bn×2, H6bα,β), 4.45 (dd, 1H, J=2.0 Hz, J=12.5 Hz, H6aα), 4.35 (d, 1H, J=8.0 Hz, H1β), 4.14 (t, 1H, J=3.5 Hz, H5α), 4.11 (t, 1H, J=4.0 Hz, H6β), 3.91-3.75 (m, 3H, H'5, H'4, H4β), 3.71 (bs, 1H, H'3), 3.51 (m, 1H, H2β), 3.44-3.42 (m, 2H, H5β, H2α), 3.25 (t, 1H, J=9.5 Hz, H3β), 3.19 (d, 1H, J=11.0 Hz, H'6b), 3.10 (d. 1H, J=11.5 Hz, H'6a). $^{13}$C NMR (75.5 MHz, $CDCl_3$): δ 170.4, 170.2, 138.1, 137.9, 137.6, 128.9, 128.4, 128.3, 128.0, 127.9, 127.9, 127.6, 127.4, 127.1, 126.1, 100.4, 98.0, 97.0, 81.2, 77.4, 77.0, 76.5, 75.0, 74.9, 73.8, 73.7, 73.5, 72.1, 69.0, 69.0, 67.1, 62.3, 60.3, 33.9, 24.8, 20.9, 20.8, 19.9, 19.8, 18.4, 18.3, −2.1, −3.3. HRMS-MALDI: (M+Na$^+$) calcd for $C_{44}H_{47}N_3O_{12}$, 809.3159. found 809.3155.

Benzyl (methyl 2-O-acetyl-3-O-benzyl-β-D-idopyranosyluronate)-(1→4)-(6-O-acetyl-2-azido-3-O-benzyl-2-deoxy-α/β-D-glucopyranoside) (4): To a solution of disaccharide 3 (0.633 g, 0.781 mmol) in DCM was added ethanethiol (0.345 mL, 4.68 mmol) and p-TsOH (29.6 mg, 0.156 mmol). The resulting reaction mixture was stirred at ambient temperature for 1 h. The reaction mixture was quenched with $Et_3N$ and concentrated in vacuo. The residue was purified by silica gel column chromatography using a stepwise gradient of toluene and EtOAc (100-80%) to give pure diol (0.543 g, 96%). To a vigorously stirred solution of the diol (0.533 g, 0.738 mmol) in a mixture of DCM:$H_2O$ (0.15 M, 2/1, v/v) was added TEMPO (22.96 mg, 0.147 mmol) and BAIB (0.594 g, 1.845 mmol). Stirring was continued until TLC indicated complete conversion of the starting material to a spot of lower $R_f$ (~45 min). The reaction mixture was quenched with aqueous $Na_2S_2O_3$ and the resulting mixture was extracted with EtOAc (2×10 mL), and the combined organic layers were dried ($MgSO_4$) and filtered, and the filtrate was concentrated in vacuo. The oily residue was dissolved in THF (0.1 M) and treated with excess of freshly prepared ethereal solution of diazomethane until the reaction mixture stayed yellow. The excess diazomethane was quenched by the addition of AcOH until the mixture became colorless. The mixture was concentrated in vacuo and the residue co-evaporated with toluene. The residue was purified by silica gel column chromatography using stepwise gradient of toluene EtOAc (100-50%) to give compound 4 (0.34 g, 83%, 2 steps). $^1$H NMR (500 MHz, $CDCl_3$): δ 7.39-7.15 (m, 30H, CH Aromatic), 5.06 (bs, 2H, H'1), 4.98 (d, 1H, J=3.5 Hz, H1α), 4.92-4.88 (m, 3H, H'2, H'S, CHH Bn), 4.74-4.58 (m, 7H, CHH Bn×4, CHH Bn×3), 4.50 (dd, 2H, J=1.5 Hz, 12.0 Hz, H6bα, H6bβ), 4.36 (d, 1H, J=12.5 Hz, H6aα), 4.31 (d, 1H, J=8.0 Hz, H1β), 4.22-4.18 (m, 2H, H5α, H6aβ), 3.96 (bt, 1H, J=10.0 Hz, H'4), 3.88-3.85 (m, 3H, H3α, H4α, H4β), 3.71 (d, 2H, J=2.5 Hz, H'3), 3.49-3.47 (m, 1H, H2β), 3.45 (s, 3H, $CO_2CH_3$), 3.41-3.36 (m, 2H, H2α, H5β), 3.25 (t, 1H, J=9.5 Hz, H3β), 2.10 (s, 3H, $CH_3$ Ac), 2.06 (s, 3H, $CH_3$ Ac). $^{13}$C NMR (75.5 MHz, $CDCl_3$): δ 70.5, 170.5, 169.4, 169.3, 169.1, 137.8, 137.7, 137.1, 136.4, 128.9, 128.5, 128.4, 128.1, 128.1, 128.0, 127.8, 127.4, 127.3, 127.3, 125.2, 100.2, 97.9, 96.6, 81.1, 78.4, 77.4, 77.0, 76.6, 75.0, 74.6, 74.4, 74.3, 74.3, 73.1, 72.2, 70.8, 69.8, 69.3, 68.4, 67.6, 67.1, 67.0, 66.2, 63.4, 62.0, 51.9, 20.8. HRMS-MALDI: (M+Na$^+$) calcd for $C_{38}H_{43}N_3O_{13}$, 749.2795. found 749.2790.

Benzyl (3-O-benzyl-β-D-idopyranosyluronate)-(1→4)-(2-azido-3-O-benzyl-2-deoxy-α/β-D-glucopyranoside) (5): To a solution of compound 4 (70 mg, 0.09 mmol) in THF (1.4 mL) was added LiOH (0.4 mL, 0.1 M) at room temperature. Stirring was continued for 40 min, after which the reaction mixture was brought to pH 9.0 by the addition of aqueous HCl (1.0 M), the resulting mixture was concentrated in vacuo and the residue was purified by column chromatography over Iatrobeads using a stepwise gradient of toluene and methanol (100-70%). Appropriate fractions were concentrated in vacuo, to provide compound 5 (60 mg, 99%). $^1$H NMR (500 MHz, $CD_3OD$): δ 7.44-7.23 (m, 30H, Aromatic), 5.04-4.98 (m, 4H, H'1, H1α, CHH Bn, CHH Bn), 4.94 (d, 2H, J=12.0 Hz, CHH Bn), 4.92-4.75 (m, 3H, CHH Bn, CHH Bn, CHH Bn), 4.70 (d, 1H, J=12.0 Hz, CHH Bn), 4.63 (t, 2H, J=10.5 Hz, CHH Bn, CHH Bn), 4.58 (d, 1H, J=12.0 Hz, CHH Bn), 4.44 (d, 1H, J=8.0 Hz, H1β), 4.41 (dd, 2H, J=4.5 Hz, J=19.0 Hz, H6bα, H'5), 4.12 (t, 1H, J=9.5 Hz, H4α), 4.04 (t, 1H, J=9.5 Hz, H4β), 3.98-3.79 (m, 5H, H6a,bβ, H6aα, H5α, H3α), 3.57-3.52 (m, 4H, H'2×2, H'3× 2), 3.46-3.43 (m, 2H, H3β, H5β), 3.39-3.35 (m, 2H, H2α, H2β). $^{13}$C NMR (75.5 MHz, $CD_3OD$): δ 176.7, 140.2, 140.0, 138.7, 129.3, 129.2, 129.0, 128.3, 101.9, 101.3, 101.2, 98.2, 82.5, 82.2, 82.0, 79.4, 77.5, 77.0, 76.6, 76.0, 75.7, 75.0, 74.9, 73.8, 73.3, 73.0, 72.8, 72.4, 72.2, 71.9, 70.5, 67.9, 64.3, 62.2, 62.1, 49.9, 49.7, 49.4, 49.1, 48.8, 48.5, 48.2; HRMS-MALDI: (M+Na$^+$) calcd for $C_{33}H_{37}N_3O_{11}$, 651.2428. found 651.2422.

Benzyl (3-O-benzyl-β-D-idopyranosyluronate)-(1→4)-(2-N-sulfoamino-3-O-benzyl-2-deoxy-α-D-glucopyranoside) (6): To a solution of compound 5 (20 mg, 0.03 mmol) in THF (2 mL) was added 1.0 M solution of $PM_3$ in THF (0.24 mL, 0.24 mmol) and NaOH (0.1 M, 3.0 mL, 0.3 mmol). The reaction mixture was stirred at room temperature for 1 h and the progress of the reaction was followed by TLC ($H_2O$/acetonitrile, 10/90, v/v). The presence of the amino group was indicated using ninhydrin as visualizing agent. After the completion of the reaction, pH was adjusted to 9.0 by careful addition of aqueous HCl (0.1 M). The mixture was concentrated in vacuo and the residue co-evaporated with toluene. To a solution of the crude residue in anhydrous methanol (5.0 mL) was added pyridinium sulfur trioxide (23.8 mg, 0.15 mmol), and triethylamine (1.5 mL, 0.30 mmol) and sodium hydroxide (0.6 mL, 0.06 mmol). Stirring was continued at room temperature for 1 h until RP-018 TLC ($H_2O$/methanol, 60/40, v/v) indicated the disappearance of the starting material. The mixture was co-evaporated with toluene in vacuo and dissolved in $H_2O$ and passed through a short column of Bio-Rad 50×8 $Na^+$ resin (0.6×2.5 cm). The residue was applied to a small RP-018 column, which was eluted with a stepwise gradient of water and methanol (90/10 to 60/40, v/v). The appropriate fractions were lyophilized to give compound 6 (15 mg, 66%). $^1$H NMR (500 MHz, $CD_3OD$): δ 7.53-7.23 (m, 15H, CH Aromatic), 5.38 (d, 1H, J=3.5 Hz, H1α), 4.96 (d, 1H, J=4.5 Hz, H'1), 4.92 (d, 1H, J=10.5 Hz, CHH Bn), 4.87-4.73 (m, 5H, CHH Bn, CHH Bn, CHH Bn, CHH Bn, CHH Bn), 4.59 (d, 1H, J=11.0 Hz, CHH Bn), 4.46 (bs, 1H, H'5), 4.01-3.99 (M, 2H, H'4, H4α), 3.85-3.83 (m, 2H, H6a,b), 3.74 (bd, 1H, J=9.5 Hz, H5α), 3.68 (t, 1H, J=10 Hz, H3α), 3.56 (m, 3H, H2α, H'2, H'3). $^{13}$C NMR (75.5 MHz, $D_2O$): δ 176.8, 140.1, 139.53, 129.4, 129.4, 129.2, 129.1, 129.0, 128.5, 128.3, 102.5, 100.5, 80.1, 79.9, 78.1, 74.6, 73.9, 73.5, 72.2, 71.7, 71.6, 71.1, 63.4, 58.2, 49.8, 49.5, 49.3, 49.0, 48.7, 48.4, 48.1.

β-D-idopyranosyluronate)-(1→4)-(2-N-sulfoamino-2-de-oxy-α/β-D-glucopyranoside) (7): Pd/(OH)$_2$ on carbon (Degussa type, 20%, 1.5 times the weight of starting material) was added to the solution of compound 6 (4 mg, 6 μmol) in tBuOH and $H_2O$ (1/1, v/v, 2 mL) and then placed under an atmosphere of hydrogen. The reaction was completed after 16 h indicated by C18 TLC ($H_2O$/acetonitrile, 10/90, v/v). The mixture was filtered through Celite and the filtrate was concentrated in vacuo. The residue was re-dissolved in water and then passed through a short column of Bio-Rad 50×8 $Na^+$ resin (0.6×2.5 cm) using $H_2O$ as eluent. Appropriate fractions were lyophilized to provide compound 7 (2 mg, 83%). $^1$H NMR (500 MHz, $D_2O$), α-anomer: δ 5.45 (d, 1H, J=3.5 Hz, H1α), 4.81 (t, 2H, J=6.0 Hz, H'1), 4.52 (t, 2H, J=4.5 Hz, H'5), 3.94-3.85 (m, 1H, H5α), 3.84-3.80 (m, 3H, H'4, H6a,b), 3.74-3.61 (m, 3H, H3α, H4α, H'3), 3.47-3.44 (m, 1H, H'2), 3.26 (dd, 1H, J=3.5 Hz, J=10.0 Hz, H2α); $^{13}$C NMR (150 MHz, $D_2O$): δ 176.6, 101.2, 91.2, 78.2, 72.7, 71.7, 71.3, 70.5, 69.6, 60.2, 58.2.

What is claimed is:

1. A method of determining in an individual the presence, identity, and/or severity of mucopolysaccharidosis (MPS) VI, the method comprising:
   (a) generating a first biomarker comprising a glycan residual compound, wherein the first biomarker is generated by treating a population of glycans, in or isolated from a biological sample from the individual, with at least one digesting glycan enzyme,
   wherein prior to enzyme treatment, the first biomarker is not present in abundance in samples from individuals with MPS VI relative to individuals without MPS VI, and wherein the first biomarker is a non-reducing end (NRE) biomarker;
   (b) generating a second biomarker comprising a glycan residual compound, wherein the second biomarker is generated by treating a population of glycans, in or isolated from a biological sample from the individual, with at least one digesting glycan enzyme,
   wherein prior to enzyme treatment, the second biomarker is not present in abundance in samples from individuals with the MPS VI relative to individuals without the MPS VI, and wherein:
   1) the second biomarker is an NRE biomarker different from the first biomarker,
   2) the second biomarker is a reducing end biomarker,
   3) the second biomarker is an internal glycan biomarker, or
   4) when the MPS VI is caused by an abnormal function of a glycan degradation enzyme in the individual, the second biomarker is generated by treating the first biomarker with the glycan degradation enzyme that is functioning abnormally in the individual;
   (c) detecting the presence of and/or measuring the amount of the first and second biomarker produced and displaying or recording the presence of or a measure of a population of the first and second biomarkers by using an analytical instrument; and
   (d) monitoring and/or comparing the amounts of the first and second biomarkers in a biological sample;
   wherein the presence of and/or measure of the amounts of the first and second biomarkers are utilized to determine the presence, identity, and/or severity of MPS VI; and
   wherein the population of glycans comprises a glycan selected from the group consisting of keratan sulfate, chondroitin sulfate, dermatan sulfate, and heparan sulfate.

2. The method of claim 1, wherein the first biomarker is selected from the group consisting of GalNAc4S, GalNAc4S-UA-GalNAc, GalNAc4S-UA-GalNAc4S, GalNAc4S-UA-GalNAc6S, GalNAc4S-UA-GalNAc4S6S, GalNAc4S-UA2S-GalNAc, GalNAc4S-UA2S-GalNAc4S, GalNAc4S-UA2S-GalNAc6S, and GalNAc4S-UA2S-GalNAc4S6S.

3. The method of claim 2, wherein the first biomarker is GalNAc4S.

4. The method of claim 2, wherein the second biomarker is selected from the group consisting of a sulfated NRE biomarker, an internal glycan biomarker, and a non-sulfated NRE biomarker.

5. The method of claim 2, wherein the second biomarker is selected from the group consisting of GalNAc6S, GalNAc6S4S, GalNAc6S-UA-GalNAc, GalNAc6S-UA-GalNAc4S, GalNAc6S-UA-GalNAc6S, GalNAc6S-UA-GalNAc4S6S, GalNAc6S-UA2S-GalNAc, GalNAc6S-UA2S-GalNAc4S, GalNAc6S-UA2S-GalNAc6S, GalNAc6S-UA2S-GalNAc4S6S, GalNAc6S4S-UA-GalNAc, GalNAc6S4S-UA-GalNAc4S, GalNAc6S4S-UA-GalNAc6S, GalNAc6S4S-UA-GalNAc4S6S, GalNAc6S4S-UA2S-GalNAc, GalNAc6S4S-UA2S-GalNAc4S, GalNAc6S4S-UA2S-GalNAc6S, GalNAc6S4S-UA2S-GalNAc4S6S, Gal6S, Gal6S-GlcNAc, Gal6S-GlcNAc6S, Gal6S-GlcNAc-Gal, Gal6S-GlcNAc-Gal6S, Gal6S-GlcNAc6S-Gal, and Gal6S-GlcNAc6S-Gal6S.

6. The method of claim 5, wherein the first biomarker is GalNAc4S.

7. The method of claim 2, wherein the second biomarker is selected from the group consisting of ΔUA-GalNAc, ΔUA-GalNAc4S, ΔUA-GalNAc6S, ΔUA2S-GalNAc, ΔUA2S-GalNAc4S, ΔUA2S-GalNAc6S, ΔUA-GalNAc4S6S, ΔUA2S-GalNAc4S6S, ΔUA-GlcN, ΔUA-GlcN6S, ΔUA2S-GlcN, ΔUAS-GlcN6S, ΔUA-GlcNAc, ΔUA-GlcNAc6S, ΔUA2S-GlcNAc, ΔUA2S-GlcNAc6S, ΔUA-GlcNS, ΔUA-GlcNS6S, ΔUA-GlcNS3S, ΔUA2S-GlcNS, ΔUA2S-GlcNS6S, ΔUA2S-GlcNS3S, ΔUA-GlcNS6S3S, and ΔUA2S-GlcNS6S3S.

8. The method of claim 7, wherein the first biomarker is GalNAc4S.

9. The method of claim 2, wherein the second biomarker is selected from the group consisting of GalNAc, GalNAc-UA-GalNAc, GalNAc-UA-GalNAc4S, GalNAc-UA-GalNAc6S, GalNAc-UA-GalNAc4S6S, GalNAc-UA2S-GalNAc, GalNAc-UA2S-GalNAc4S, GalNAc-UA2S-GalNAc6S, GalNAc-UA2S-GalNAc4S6S, Gal, Gal-GlcNAc, Gal-GlcNAc6S, Gal-GlcNAc-Gal, Gal-GlcNAc-Gal6S, Gal-GlcNAc6S-Gal, and Gal-GlcNAc6S-Gal6S.

10. The method of claim 9, wherein the first biomarker is GalNAc4S.

11. The method of claim 2, wherein the first biomarker is GalNAc4S and the second biomarker is GalNAc6S.

12. A method of determining in an individual the presence, identity, and/or severity of MPS IVA, the method comprising:
(a) generating a first biomarker comprising a glycan residual compound, wherein the first biomarker is generated by treating a population of glycans, in or isolated from a biological sample from the individual, with at least one digesting glycan enzyme,
wherein prior to enzyme treatment, the first biomarker is not present in abundance in samples from individuals with MPS IVA relative to individuals without MPS IVA, and wherein the first biomarker is an NRE biomarker;
(b) generating a second biomarker comprising a glycan residual compound, wherein the second biomarker is generated by treating a population of glycans, in or isolated from a biological sample from the individual, with at least one digesting glycan enzyme,
wherein prior to enzyme treatment, the second biomarker is not present in abundance in samples from individuals with the MPS IVA relative to individuals without the MPS IVA, and wherein:
1) the second biomarker is an NRE biomarker different from the first biomarker,
2) the second biomarker is a reducing end biomarker,
3) the second biomarker is an internal glycan biomarker, or
4) when the MPS IVA is caused by an abnormal function of a glycan degradation enzyme in the individual, the second biomarker is generated by treating the first biomarker with the glycan degradation enzyme that is functioning abnormally in the individual;
(c) detecting the presence of and/or measuring the amount of the first and second biomarker produced and displaying or recording the presence of or a measure of a population of the first and second biomarkers by using an analytical instrument; and
(d) monitoring and/or comparing the amounts of the first and second biomarkers in a biological sample;
wherein the presence of and/or measure of the amounts of the first and second biomarkers are utilized to determine the presence, identity, and/or severity of MPS IVA; and
wherein the population of glycans comprises a glycan selected from the group consisting of keratan sulfate, chondroitin sulfate, dermatan sulfate, and heparan sulfate.

13. The method of claim 12, wherein the first biomarker is selected from the group consisting of GalNAc6S, GalNAc6S4S, GalNAc6S-UA-GalNAc, GalNAc6S-UA-GalNAc4S, GalNAc6S-UA-GalNAc6S, GalNAc6S-UA-GalNAc4S6S, GalNAc6S-UA2S-GalNAc, GalNAc6S-UA2S-GalNAc4S, GalNAc6S-UA2S-GalNAc6S, GalNAc6S-UA2S-GalNAc4S6S, GalNAc6S4S-UA-GalNAc, GalNAc6S4S-UA-GalNAc4S, GalNAc6S4S-UA-GalNAc6S, GalNAc6S4S-UA-GalNAc4S6S, GalNAc6S4S-UA2S-GalNAc, GalNAc6S4S-UA2S-GalNAc4S, GalNAc6S4S-UA2S-GalNAc6S, GalNAc6S4S-UA2S-GalNAc4S6S, Gal6S, Gal6S-GlcNAc, Gal6S-GlcNAc6S, Gal6S-GlcNAc-Gal, Gal6S-GlcNAc-Gal6S, Gal6S-GlcNAc6S-Gal, and Gal6S-GlcNAc6S-Gal6S.

14. The method of claim 13, wherein the first biomarker is GalNAc6S.

15. The method of claim 13, wherein the second biomarker is selected from the group consisting of a sulfated NRE biomarker, an internal glycan biomarker, and a non-sulfated NRE biomarker.

16. The method of claim 13, wherein the second biomarker is selected from the group consisting of GalNAc4S, GalNAc4S-UA-GalNAc, GalNAc4S-UA-GalNAc4S, GalNAc4S-UA-GalNAc6S, GalNAc4S-UA-GalNAc4S6S, GalNAc4S-UA2S-GalNAc, GalNAc4S-UA2S-GalNAc4S, GalNAc4S-UA2S-GalNAc6S, and GalNAc4S-UA2S-GalNAc4S6S.

17. The method of claim 16, wherein the first biomarker is GalNAc6S.

18. The method of claim 13, wherein the second biomarker is selected from the group consisting of ΔUA-GalNAc, ΔUA-GalNAc4S, ΔUA-GalNAc6S, ΔUA2S-GalNAc, ΔUA2S-GalNAc4S, ΔUA2S-GalNAc6S, ΔUA-GalNAc4S6S, ΔUA2S-GalNAc4S6S, ΔUA-GlcN, ΔUA-GlcN6S, ΔUA2S-GlcN, ΔUAS-GlcN6S, ΔUA-GlcNAc, ΔUA-GlcNAc6S, ΔUA2S-GlcNAc, ΔUA2S-GlcNAc6S, ΔUA-GlcNS, ΔUA-GlcNS6S, ΔUA-GlcNS3S, ΔUA2S-GlcNS, ΔUA2S-GlcNS6S, ΔUA2S-GlcNS3S, ΔUA-GlcNS6S3S, and ΔUA2S-GlcNS6S3S.

19. The method of claim 18, wherein the first biomarker is GalNAc6S.

20. The method of claim 13, wherein the second biomarker is selected from the group consisting of GalNAc, GalNAc-UA-GalNAc, GalNAc-UA-GalNAc4S, GalNAc-UA-GalNAc6S, GalNAc-UA-GalNAc4S6S, GalNAc-UA2S-GalNAc, GalNAc-UA2S-GalNAc4S, GalNAc-UA2S-GalNAc6S, GalNAc-UA2S-GalNAc4S6S, Gal, Gal-GlcNAc, Gal-GlcNAc6S, Gal-GlcNAc-Gal, Gal-GlcNAc-Gal6S, Gal-GlcNAc6S-Gal, and Gal-GlcNAc6S-Gal6S.

21. The method of claim 20, wherein the first biomarker is GalNAc6S.

22. The method of claim 13, wherein the first biomarker is GalNAc6S and the second biomarker is GalNAc4S.

23. The method of claim 1, wherein the at least one digesting glycan enzyme is a glycosaminoglycan lyase.

24. The method of claim 1, wherein the at least one digesting glycan enzyme is a glycosidase.

25. The method of claim 24, wherein the glycosidase is a hexosaminidase.

26. The method of claim 25, wherein the hexosaminidase is an N-acetyl-galactosidase.

27. The method of claim 26, wherein the N-acetyl-galactosidase is chondroitinase ABC.

28. The method of claim 12, wherein the at least one digesting glycan enzyme is a glycosaminoglycan lyase.

29. The method of claim 12, wherein the at least one digesting glycan enzyme is a glycosidase.

30. The method of claim 29, wherein the glycosidase is a hexosaminidase.

31. The method of claim 30, wherein the hexosaminidase is an N-acetyl-galactosidase.

32. The method of claim 31, wherein the N-acetyl-galactosidase is chondroitinase ABC.

33. The method of claim 1, wherein the population of glycans comprises a glycan selected from the group consisting of keratan sulfate and chondroitin sulfate.

34. The method of claim 12, wherein the population of glycans comprises a glycan selected from the group consisting of keratan sulfate and chondroitin sulfate.

* * * * *